US011325955B2

(12) United States Patent
Walensky et al.

(10) Patent No.: US 11,325,955 B2
(45) Date of Patent: May 10, 2022

(54) STABILIZED ANTI-MICROBIAL PEPTIDES FOR THE TREATMENT OF ANTIBIOTIC-RESISTANT BACTERIAL INFECTIONS

(71) Applicant: Dana-Farber Cancer Institute, Inc., Boston, MA (US)

(72) Inventors: Loren D. Walensky, Newton, MA (US); Rida Mourtada, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/631,315

(22) PCT Filed: Jul. 18, 2018

(86) PCT No.: PCT/US2018/042640
§ 371 (c)(1),
(2) Date: Jan. 15, 2020

(87) PCT Pub. No.: WO2019/018499
PCT Pub. Date: Jan. 24, 2019

(65) Prior Publication Data
US 2020/0207821 A1   Jul. 2, 2020

Related U.S. Application Data

(60) Provisional application No. 62/644,114, filed on Mar. 16, 2018, provisional application No. 62/534,464, filed on Jul. 19, 2017.

(51) Int. Cl.
| | | |
|---|---|---|
| *C07K 14/46* | (2006.01) | |
| *A61P 31/04* | (2006.01) | |
| *A61L 27/22* | (2006.01) | |
| *C07K 1/113* | (2006.01) | |
| *C12Q 1/18* | (2006.01) | |
| *A61K 38/00* | (2006.01) | |

(52) U.S. Cl.
CPC .......... *C07K 14/463* (2013.01); *A61L 27/227* (2013.01); *A61P 31/04* (2018.01); *C07K 1/113* (2013.01); *C07K 14/461* (2013.01); *C12Q 1/18* (2013.01); *A61K 38/00* (2013.01)

(58) Field of Classification Search
CPC .......... A61L 27/18; A61L 31/06; A61L 15/26; A61L 2300/406; A61L 17/005; A01N 25/10; A61K 47/34; A61K 38/00; A61K 38/12; A61K 31/065; A61K 38/1729; A61P 31/04
See application file for complete search history.

(56) References Cited

U.S. PATENT DOCUMENTS

| | | |
|---|---|---|
| 5,446,090 A | 8/1995 | Harris |
| 5,607,914 A | 3/1997 | Roa et al. |
| 5,861,478 A | 1/1999 | Jaynes |
| 5,885,829 A | 3/1999 | Mooney et al. |
| 5,912,231 A | 6/1999 | Houghten et al. |
| 6,001,805 A | 12/1999 | Jaynes et al. |
| 6,348,558 B1 | 2/2002 | Harris et al. |
| 6,620,954 B1 | 9/2003 | Boaz |
| 7,723,468 B2 | 5/2010 | Daffre et al. |
| 8,198,405 B2 | 6/2012 | Walensky et al. |
| 8,889,632 B2 | 11/2014 | Bernal et al. |
| 9,079,970 B2 | 7/2015 | Walensky et al. |
| 9,296,805 B2 | 3/2016 | Walensky et al. |
| 9,464,115 B2 | 10/2016 | Walensky et al. |
| 9,527,896 B2 | 12/2016 | Bernal et al. |
| 10,464,975 B2 | 11/2019 | Walensky et al. |
| 2001/0025048 A1 | 9/2001 | Crabb et al. |
| 2003/0096949 A1 | 5/2003 | Hancock et al. |
| 2003/0104581 A1 | 6/2003 | Hoess et al. |
| 2004/0197864 A1* | 10/2004 | Sun .......................... A61P 31/00 435/69.1 |
| 2005/0250680 A1 | 11/2005 | Walensky et al. |
| 2006/0287232 A1 | 12/2006 | Clayberger et al. |
| 2010/0093086 A1 | 4/2010 | Lin et al. |
| 2010/0069308 A1 | 5/2010 | Chorny et al. |
| 2010/0168388 A1 | 7/2010 | Bernal et al. |

(Continued)

FOREIGN PATENT DOCUMENTS

| | | |
|---|---|---|
| CA | 2367149 | 9/2011 |
| CN | 1906209 | 1/2007 |

(Continued)

OTHER PUBLICATIONS

Bird et al. Hydrocarbon double-stapling remedies the proteolytic instability of a lengthy peptide therapeutic. PNAS. 2010; 107(32): 14093-14098. (Year: 2010).*

(Continued)

*Primary Examiner* — Aradhana Sasan
*Assistant Examiner* — Jia-Hai Lee
(74) *Attorney, Agent, or Firm* — Fish & Richardson P.C.

(57) ABSTRACT

Methods of generating and optimizing stabilized (e.g., stapled and/or stitched) anti-microbial peptides (StAMPs) for the prophylaxis and treatment of antibiotic-resistant (e.g., colistin-resistant, methicillin resistant, meropenem-resistant) bacterial infections (e.g., Gram-negative, Gram-positive), and methods for using such peptides for experimental investigation, livestock management, management of crops/trees/plants, and/or therapeutic benefit. Also featured are methods for reducing renal toxicity of a StAMP.

31 Claims, 4 Drawing Sheets
Specification includes a Sequence Listing.

(56) References Cited

U.S. PATENT DOCUMENTS

| | | |
|---|---|---|
| 2010/0286057 A1 | 11/2010 | Walensky et al. |
| 2011/0159091 A1 | 6/2011 | Stone et al. |
| 2011/0288007 A1 | 11/2011 | Fox et al. |
| 2012/0172285 A1 | 7/2012 | Walensky et al. |
| 2014/0113857 A1 | 4/2014 | Walensky et al. |
| 2014/0155319 A1 | 6/2014 | Bond et al. |
| 2014/0296232 A1 | 10/2014 | Hung et al. |
| 2014/0370042 A1 | 12/2014 | Walensky et al. |
| 2015/0087512 A1 | 3/2015 | Wang et al. |
| 2015/0087579 A1 | 3/2015 | Stange et al. |
| 2015/0290278 A1 | 10/2015 | Deber |
| 2016/0046671 A1 | 2/2016 | Leshchiner et al. |
| 2016/0068834 A1 | 3/2016 | Walensky |
| 2016/0110706 A1 | 4/2016 | Li et al. |
| 2016/0319436 A1 | 11/2016 | Wagh et al. |
| 2017/0015716 A1 | 1/2017 | Walensky et al. |
| 2017/0081379 A1 | 3/2017 | Bernal et al. |
| 2017/0247423 A1 | 8/2017 | Walensky et al. |
| 2017/0260248 A1 | 9/2017 | Walensky et al. |
| 2020/0231638 A1 | 7/2020 | Walensky et al. |
| 2020/0308236 A1 | 10/2020 | Walensky et al. |

FOREIGN PATENT DOCUMENTS

| | | | |
|---|---|---|---|
| CN | 103467588 | 12/2013 | |
| DE | 1991/4817 | 10/2000 | |
| JP | 2002-501079 | 1/2002 | |
| JP | 2003-531101 A | 10/2003 | |
| JP | 2010-528052 A | 8/2010 | |
| KR | 2010/0065639 | 6/2010 | |
| WO | WO 1991/000869 | 1/1991 | |
| WO | WO1991000869 | * 1/1991 | ............... C07K 7/08 |
| WO | WO 1999/014259 | 3/1999 | |
| WO | WO 1999/034833 | 7/1999 | |
| WO | WO 1999/037644 | 7/1999 | |
| WO | WO 2000/004915 | 2/2000 | |
| WO | WO 2001/00209 | 1/2001 | |
| WO | WO 2002/079408 | 10/2002 | |
| WO | WO 2003/007989 | 1/2003 | |
| WO | WO 2003/083441 | 10/2003 | |
| WO | WO 2007/122482 | 11/2007 | |
| WO | WO 2008/086042 | 7/2008 | |
| WO | WO 2008/095063 | 8/2008 | |
| WO | WO 2008/058575 | 10/2008 | |
| WO | WO 2008/121767 | 10/2008 | |
| WO | WO 2009/108261 | 9/2009 | |
| WO | WO 2010/042534 | 4/2010 | |
| WO | WO 2010/060112 | 5/2010 | |
| WO | WO 2010/068684 | 6/2010 | |
| WO | WO 2010/148335 | 12/2010 | |
| WO | WO 2010/149792 | 12/2010 | |
| WO | WO 2013/039857 | 3/2013 | |
| WO | WO 2013/102211 | 7/2013 | |
| WO | WO 2014/100777 | 6/2014 | |
| WO | WO 2014/159969 | 10/2014 | |
| WO | WO 2015/070912 | 5/2015 | |
| WO | WO 2015/138494 | 9/2015 | |
| WO | WO 2015/112980 | 10/2015 | |
| WO | WO 2017/004591 | 1/2017 | |
| WO | WO 2017/147283 | 8/2017 | |
| WO | WO 2017/151617 | 9/2017 | |
| WO | WO 2019/018499 | 1/2019 | |

OTHER PUBLICATIONS

Hayouka et al. Evidence for Phenylalanine Zipper-Mediated Dimerization in the X-ray Crystal Structure of a Magainin 2 Analogue. J. Am. Chem. Soc. 2013, 135, 15738-15741. (Year: 2013).*
Sun et al. Membrane Permeability of Hydrocarbon-Cross-Linked Peptides. Biophysical Journal vol. 104 May 2013 1923-1932. (Year: 2013).*
Baker et al., "Anticancer Efficacy of Magainin2 and Analogue Peptides," Cancer Research, Jul. 1993, 53(13):3052-3057.
Balaram, "Non-standard amino acids in peptide design and protein engineering," Cur Opin Struct Biol, 1992, 2(6):845-851.
Chin et al., "Design and Evolution of a Miniature Bcl-2 Binding Protein," Angew Chem Int. Ed., 2001, 40(20):3806-3809.
Corsello et al., "Discovering the anti-cancer potential of non-oncology drugs by systematic viability profiling," Nat Cancer, 2020, 1(2):235-248.
Gunnoo et al., "Bioconjugation—using selective chemistry to enhance the properties of proteins and peptides as therapeutics and carriers," Org. Biomol. Chem., 2016, 14(34):8002-8013.
Hayouka et al., "Evidence for phenylalanine zipper-mediated dimerization in the X-ray crystal structure of a magainin 2 analogue," J. Am. Chem. Soc., 2013, 135(42):15738-15741.
Horne et al., "Sequence-based design of alpha/beta-peptide foldamers that mimic BH3 domains," Angew Chem Int Ed Engl., 2008, 47(15):2853-6.
Invenio.nusl.cz, [online], "Design of stable antimicrobial peptides through hydrocarbon stapling." 2011, retrieved on Feb. 4, 2021, retrieved from URL<http://invenio.nusl.cz/record/80987>, 1 page.
Kemp et al., "The Structure and Energetics of Helix Formation by Short Templated Peptides in Aqueous Solution. 2. Characterization of the Helical Structure of Ac—Hel1—Ala6—OH," J. Am. Chem. Soc., 1996, 118(18):4240-4248.
Lee et al., "Helical antimicrobial peptides assemble into protofibril scaffolds that present ordered dsDNA to TLR9," Nature Communications, 2019, 10:1012, 10 pages.
Lehmann et al., "Antitumor activity of the antimicrobial peptide magainin II against bladder cancer cell lines," Eur Urol., Jul. 2006, 50(1):141-7.
Li et al., "The landscape of cancer cell line metabolism," Nature Medicine, 2019, 25(5):850-860.
Ling et al., "More than fishing for a cure: The promises and pitfalls of high throughput cancer cell line screens," Pharmacology & Therapeutics, 2018, 191:178-189.
Madden et al., "Facile synthesis of stapled, structurally reinforced peptide helices via a photoinduced intramolecular 1,3-dipolar cycloaddition reaction," Chem Commun (Camb), 2009, 37:5588-5590.
McFarland et al., "Multiplexed single-cell transcriptional response profiling to define cancer vulnerabilities and therapeutic mechanism of action." Nature Communications, 2020, 11(1):4296, 15 pages.
Mourtada et al., "Design of stapled antimicrobial peptides that are stable, nontoxic and kill antibiotic-resistant bacteria in mice," Nature Biotechnology, 2019, 37(10):1186-1197.
Oberlick et al., "Small-Molecule and CRISPR Screening Converge to Reveal Receptor Tyrosine Kinase Dependencies in Pediatric Rhabdoid Tumors," Cell Reports, 2019, 28(9):2331-2344.
Orner et al., "Toward proteomimetics: terphenyl derivatives as structural and functional mimics of extended regions of an alpha-helix," J. Am. Chem. Soc, 2001, 123(22):5382-3.
Park et al., "A Novel Antimicrobial Peptide from Bufo bufo gargarizans," BBRC. 1996, 218:408-413.
PCT International Search Report and Written Opinion in International Appln. No. PCT/US2020/065078, dated Mar. 2, 2021, 17 pages.
Sancar-Bas et al., "Esculentin-2PLa, a frog skin antimicrobial peptide, causes necrotic cell death in breast cancer cell lines," EACR24 Poster Sessions, European Journal of Cancer, 2016, 61(Suppl. 1):S132-S133.
Schauer et al., "Selective USP7 inhibition elicits cancer cell killing through a p53-dependent mechanism," Scientific Reports, 2020, 10:5324, 15 pages.
Tsvetkov et al., "Mitochondrial metabolism promotes adaptation to proteotoxic stress," Nat Chem Biol., 2019, 15(7):681-689.
Yu et al., "High-throughput identification of genotype-specific cancer vulnerabilities in mixtures of barcoded tumor cell lines," Nat. Biotechnol., 2016, 34(4):419-423.
U.S. Appl. No. 15/201,235, U.S. Pat. No. 10,464,975, 2017/0015716, filed Jul. 1, 2016, Loren D. Walensky.
U.S. Appl. No. 16/551,102, 2020/0231638, filed Aug. 26, 2019, Loren D. Walensky.
U.S. Appl. No. 17/091,541, filed Nov. 6, 2020, Loren D. Walensky.
U.S. Appl. No. 15/445,502, 2017/0247423, filed Feb. 28, 2017, Loren D. Walensky.

(56) References Cited

OTHER PUBLICATIONS

U.S. Appl. No. 16/813,528, 2020/0308236, filed Mar. 3, 2020, Loren D. Walensky.
Hocquellet et al., "Structure-Activity relationship of human liver-expressed antimicrobial peptide 2," Peptides, 2010, 31:58-66.
U.S. Appl. No. 16/813,528, filed Mar. 3, 2020, Walensky.
Acharya, "Extracellular And Intracellular Bacteria And Their Preferred Growth Phase Within The Host," *Bacteriology*, May 30, 2013, 5 pages.
Alberts et al., "Bacterial shapes and cell-surface structures: Figure 25-4," *Molecular Biology of the Cell*—NCBI Bookshelf, 2002, 4th Edition, 1 page.
Alberts et al., "Visualizing Cells," *Molecular Biology of the Cell*, Chapter 9, 5th Edition, 2007, p. 579-615.
Altschul et al. (1997) *Gapped BLAST and PSI-BLAST: a new generation of protein database search programs*. Nucleic Acids Res. 25:3389-3402.
Amsel et al. "Nonspecific vaginitis. Diagnostic criteria and microbial and epidemiologic associations," *Am. J. Med.* 74:14-22 (1983).
Arnusch et al., "Enhanced membrane pore formation through high-affinity targeted antimicrobial peptides," *PLoSOne*, 2012, 7(6):e39768, 5 pages.
Atashili, et al., "Bacterial Vaginosis And HIV Acquisition: A Meta-Analysis Of Published Studies," *AIDS*, 22(12):1493-1501 (Jul. 2008).
Bajaj et al, "Stereochemical criteria for prediction of the effects of proline mutations on protein stability." *PLoS Connput. Biol.* (2007) 3(12) e241.
Bang, et al., (2004) "Total chemical synthesis of crambin," *J. Am. Chem. Soc.* 126:1377-83.
Barker et al., "The fate of norleucine as a replacement for methionine in protein synthesis," *J. Mol. Biol.*, Sep. 1979, 133(2):217-231.
Bechinger, "Structure and functions of channel-forming peptides: magainins, cecropins, melittin and alamethicin," *Journal of Membrane Biology*, 1997, 156:197-211.
Bernal et al., "A Stapled p53 Helix Overcomes HDMX-Mediated Suppression of p53," *Cancer Cell*, Nov. 2010, 18(5):411-422.
Bird et al., "Biophysical determinants for cellular uptake of hydrocarbon-stapled peptide helices," *Nature Chemical Biology*, Aug. 2016, 12:845-853.
Bird et al., "Chemical synthesis of hydrocarbon-stapled peptides for protein interaction research and therapeutic targeting," *Curr Protoc Chem Biol.*, Sep. 2011, 3(3):99-117.
Bird et al., "Hydrocarbon double-stapling remedies the proteolytic instability of a lengthy peptide therapeutic," *Proc Natl Acad Sci USA*, Aug. 2010, 107(32):14093-8.
Bird et al., "Mucosal delivery of a double-stapled RSV peptide prevents nasopulmonary infection," *J Clin Invest.*, May 2014, 124(5):2113-2124.
Bird et al., "Synthesis and biophysical characterization of stabilized alpha-helices of BCL-2 domains," *Meth Enzymol.*, 2008, 446:369-386.
Blackwell et al., "Highly Efficient Synthesis of Covalently Cross-Linked Peptide Helices by Ring-Closing Metathesis," *Angewandte Chemie*, Dec. 1998, 37(23):3281-3284.
Blackwell et al., "Ring-closing metathesis of olefinic peptides: design, synthesis, and structural characterization of macrocyclic helical peptides." *J Org Chem.*, Aug. 2001, 66(16): 5291-5302.
Blondelle et al., "Design of model amphipathic peptides having potent antimicrobial activities," *Biochemistry*, 1992, 31:12688-12694.
Bray, "Large-scale manufacture of peptide therapeutics by chemical synthesis," *Nature Reviews Drug Discovery*, 2003, 2:587-593.
Brogden, "Antimicrobial peptides: pore formers or metabolic inhibitors in bacteria?," *Nat. Rev. Microbiol.*, Mar. 2005, 3(3):238-250.
Brunel et al., "Synthesis of constrained helical peptides by thioether ligation: application to analogs of gp41," *Chemical Communications*, 2005, 2552-2554.
Bustillo et al., "Modular analysis of hipposin, a histone-derived antimicrobial peptide consisting of membrane translocating and membrane permeabilizing fragments," *Biochimica Et Biophysica Acta (BBA)—Biomembranes*, 2014, 1838(9):2228-2233.
Chang et al.. "Stapled α-helical peptide drug development: A potent dual inhibitor of MDM2 and MDMX for p53-dependent cancer therapy," *PNAS U.S.A.*, Sep. 2013, 110(36):E3445-3454.
Chapman et al., "A highly stable short alpha-helix constrained by a main-chain hydrogen bond surrogate," *J. Am. Chem. Soc.*, 2004, 126:12252-12253.
Chapman et al.. "Optimized synthesis of hydrogen-bond surrogate helicies: surprising effects of microwave heating on the activity of grubbs catalysts," *Org. Lett.*, 2006, 8(25) p. 5825-5828.
Chapuis et al., "Effect of hydrocarbon stapling on the properties of α-helical antimicrobial peptides isolated from the venom of hymenoptera," *Amino Acids*, Nov. 2012, 43(5):2047-58.
Chekmenev et al., "Investigating molecular recognition and biological function at interfaces using piscidins, antimicrobial peptides from fish." *Biochimica et Biophysica Acta*, 2006. 1758(9):1359-72.
Cho et al., "Buforins: histone H2A-derived antimicrobial peptides from toad stomach," *Biochimica et Biophysica Acta*, 2009, 1788:1564-1569.
Dathe et al., "Hydrophobicity, hydrophobic moment and angle subtended by charged residues modulate antibacterial and haemolytic activity of amphipathic helical peptides," *FEBS Letters*, 1997, 403:208-212.
Del Rio et al., "APAP, a sequence-pattern recognition approach identifies substance P as a potential apoptotic peptide," *FEBS Letters*, Apr. 2001, 494(3): 213-219.
Devi et al., "Antibodies to poly[(2—8)-alpha-N-acetylneuraminic acid] and poly[(2—9)-alpha-N-acetylneuraminic acid] are elicited by immunization of mice with *Escherichia coli* K92 conjugates: potential vaccines for groups B and C meningococci and *E. coli* K1," *Proc. Natl. Acad. Sci. USA*, Aug. 1991, 88(16):7175-7179.
Dinh et al., "Antimicrobial Activity of Doubly-Stapled Alanine/Lysine-Based Peptides," *Bioorg & Med Chem Lett.*, Sep. 2015, 25(18):4016-9.
Epand et al., "Molecular mechanisms of membrane targeting antibiotics," *Biochimica et Biophysica Acta*, Oct. 2016, 1858:980-987.
European Extended Search Report in European Patent Application No. 16818936.3, dated Jun. 17, 2019, 17 pages.
ext.impmc.upmc.fr [online], "Guidlines to Hydrophobic Cluster Analysis (HCA)," 2013, retrieved Apr. 15, 2020, retrieved from URL<http://www.ext.impmc.upmc.fr/~callebau/HCA.html>, 4 pages.
Fattom et al., "Serum antibody response in adult volunteers elicited by injection of *Streptococcus* pneumoniae type 12F polysaccharide alone or conjugated to diphtheria toxoid," *Infect. Immun.*, Jul. 1990, 58(7):2309-2312.
Feder et al., "Structure-Activity Relationship Study of Antimicrobial Dermaseptin S4 Showing the Consequences of Peptide Oligomerization on Selective Cytotoxicity," *Journal of Biological Chemistry*, 2000, 275(6):4230-4238.
Fields et al., Chapter 3 in Synthetic Peptides: A User's Guide, ed. Grant, W. H. Freeman & Co., New York, N.Y., 1992, p. 77-183.
Fjell et al., "Designing antimicrobial peptides: form follows function," *Nat Rev Drug Discov.*, Dec. 2011, 11(1):37-51.
Forsum et al. "Bacterial vaginosis—a microbiological and immunological enigma." *APMIS* 113(2):81-90 (Feb. 2005).
Fuerst et al., "Protein uptake by bacteria: an endocytosis-like process in the planctomycete Gemmata obscuriglobus," *Communicative & Integrative Biology*, 2010, 3(6):572-575.
Gordon et al., "A Review of Antimicrobial Peptides and Their Therapeutic Potential as Anti-Infective Drugs." *Curr Eye Res.*, Jul. 2005, 30(7):505-515.
Gupta et al., "Valacyclovir and Acyclovir for Suppression of Shedding of Herpes Simplex Virus in the Genital Tract," *J. Infect. Dis.*, 190:1374-1381 (Oct. 2004).
Haney et al., "Promoting peptide α-helix formation with dynamic covalent oxime side-chain cross-links," *Chemical Communications*, 2011, 47:10915-10917.
Hao et al., "The intracellular mechanism of action on *Escherichia coli* of BF2-A/C, two analogues of the antimicrobial peptide Buforin 2," *Journal of Microbiology*, 2013, 51(2):200-206.
Hawes et al. "Hydrogen Peroxide-Producing Lactobacilli and Acquisition of Vaginal Infections," *J. Infect. Dis.*, 1996, 174:1058-1063.

(56) References Cited

OTHER PUBLICATIONS

Hilinski et al., "Stitched α-helical peptides via bis ring-closing metathesis," *Journal of the American Chemical Society*, 2014, 136:12314-12322.
Hillier et al., "Association between bacterial vaginosis and preterm delivery of a low-birth-weight infant," The Vaginal Infections and Prematurity Study Group, *N. Engl. J. Med.*, Dec. 1995, 333(26):1737-1742.
Hilpert et al., "Peptide arrays on cellulose support: SPOT synthesis, a time and cost efficient method for synthesis of large numbers of peptides in a parallel and addressable fashion," *Nature Protocols*, 2007, 2(6):1333-1349.
Ho et al., "The flexibility in the proline ring couples to the protein backbone," *Protein Science*, 2005,14:1011-1018.
Hoskin et al., "Studies on anticancer activities of antimicrobial peptides," *Biochim. Biophys. Acta*, 2008, 1778(2):357-375.
Huber et al., "Robust production of a peptide library using methodological synchronization," *Protein Expression and Purification*, 2009, 67:139-147.
Imura et al., "Magainin 2 in action: distinct modes of membrane permeabilization in living bacterial and mammalian cells," *Biophys. J*, 2008, 95:5757-5765.
Jackson et al., "General Approach to the Synthesis of Short .apha.-helical Peptides," *Journal of the American Chemical Society*. Nov. 1991, 113:9391-9392.
Jenner et al., "Hydrocarbon-stapled lipopeptides exhibit selective antimicrobial activity," *Biopolymers*., May 2017, 108(3):12 pages.
Jermy, "Evolution: Bacterial endocytosis uncovered," *Nature Reviews Microbiology*, 2010, 8:534, 1 page.
Kang et al., "Antimicrobial peptides: therapeutic potentials," Expert review of anti-infective therapy, 2014, 12(12):1477-1486.
Kawamoto et al., "Design of triazole-stapled BCL9 α-helical peptides to target the β-catenin/B-cell CLL/lymphoma 9 (BCL9) protein-protein interaction," *J Med Chem.*, Feb. 2012, 55(3):1137-46.
Kim et al., "Synthesis of all-hydrocarbon stapled α-helical peptides by ring-closing olefin metathesis," *Nature Protocols*, 2011, 6(6):761-771.
Klevens et al., "Estimating Health Care-Associated Infections and Deaths in U.S. Hospitals," *Public Health Reports*, Mar. 2007, 122(2):160-166.
Kovacs et al., "Determination of Intrinsic Hydrophilicity/Hydrophobicity of Amino Acid Side Chains in Peptides in the Absence of Nearest-Neighbor or Conformational Effects," *Biopolymers*, 2006, 84(3):283-97.
Kumita et al., "Photo-control of helix content in a short peptide," *Proc. Natl. Acad. Sci. U.S.A.*, Apr. 2000, 97:3803-3808.
Lau et al., "Functionalised staple linkages for modulating the cellular activity of stapled peptides." *Chemical Science*, 2014, 5:1804-1809.
Lau et al., "Peptide stapling techniques based on different macrocyclisation chemistries," *Chemical Society Reviews*, 2015, 44(1):91-102.
Lee et al., "Solution structure and cell selectivity of piscidin 1 and its analogues," *Biochemistry*, Mar. 2007, 46(12):3653-63.
Li et al., "A versatile platform to analyze low-affinity and transient protein-protein interactions in living cells in real time," *Cell Reports*, 2014, 9:1946-1958.
Li et al. "Comparative immunogenicities of Vi polysaccharide-protein conjugates composed of cholera toxin or its B subunit as a carrier bound to high- or lower-molecular-weight Vi," *Infect. Immun.*, Dec. 1989, 57(12):3823-3827.
Liu et al., "Comparative antimicrobial activity and mechanism of action of bovine lactoferricin-derived synthetic peptides," *Biometals*, 2011, 24:1069-1078.
Liu et al., "Intramolecular cyclization of the antimicrobial peptide Polybia-MPI with triazole stapling: influence on stability and bioactivity," *J Pept Sci.*, Nov. 2017, 23(11):824-832.
Liu et al., "Use of LC/MS peptide mapping for characterization of isoforms in 15N-labeled recombinant human leptin," *Techniques in Protein Chemistry*, 1997, 8:155-63.

Lodish et al., "Schematic diagram of typical membrane proteins in a biological membrane," *Molecular Cell Biology*, 2000, 4th Edition, 1 page.
Lonhienne et al., "Endocytosis-like protein uptake in the bacterium Gemmata obscuriglobus," *Proceedings of the National Academy of Sciences*, 2010, 107(29):12883-12888.
Luong et al., "Mono-substitution effects on antimicrobial activity of stapled heptapeptides," *Arch Pharm Res*, Jun. 2017, 40(6):713-719.
Madden et al., "Synthesis of Cell-Permeable Stapled Peptide Dual Inhibitors of the p53-Mdm2/Mdmx Interactions via Photoinduced Cycloaddition," *Bioorg. Med. Chem. Lett.*, Mar. 2011, 21:1472-1475.
Mansour, et al., "Host defense peptides: front-line immunomodulators," *Trends Immunol.* 35(9):443-450 (Sep. 2014).
Maraj et al., "Evaluation of Hemolysis in Patients with Prosthetic Heart Valves," *Clin. Cardiol.*, 1998, 21:387-392.
Messer, Posterior pituitary hormones, http://163.178.103.176/casosberne/8hendocrino/caso44-2/htm1c/casosb2/v2/ vasopressin. htm, available 2000.
Migon et al., "Hydrocarbon Stapled Antimicrobial Peptides," *The Protein Journal*, 2018, 37:2-12.
Munoz et al., "Elucidating die folding problem of helical peptides using empirical parameters," *Nature Structural Biology*, 1994, 1(6): 399-409.
Nicolas et al., "Multifunctional host defense peptides: intracellular-targeting antimicrobial peptides," *FEBS Journal*, Nov. 2009, 276(22):6483-6496.
Park et al., "Mechanism of action of the antimicrobial peptide buforin II: buforin ii kills microorganisms by penetrating the cell membrane and inhibiting cellular functions," *Biochem. Biophys. Res.*, 1998, 244:253-257.
Park et al., "Structure-activity analysis of buforin II, a histone H2A-derived antimicrobial peptide: The proline hinge is responsible for the cell-penetrating ability of buforin II," *Proceedings of the National Academy of Sciences*, Jul. 2000, 97(15):8245-8250.
Patch et al., "Helical peptoid mimics of magainin-2 amide," *Journal of the American Chemical Society*, 2003, 125(40):12092-12093.
Patgiri et al., "Solid-phase synthesis of short α-helices stabilized by the hydrogen bond surrogate approach," *Nat Protoc.*, Nov. 2010, 5(11):1857-1865.
PCT International Preliminary Report on Patentability for Intl. App. No. PCT/US2016/040849, dated Jan. 2, 2018, 14 pages.
PCT International Preliminary Report on Patentability in International Application No. PCT/US2017/019953, dated Sep. 4, 2018, 10 pages.
PCT International Preliminary Report on Patentability in International Appln. No. PCT/US2018/042640, dated Jan. 21, 2020, 12 pages.
PCT International Search Report and Written Opinion for Int. App. No. PCT/US2016/040849, dated Jan. 10, 2017 21 pages.
PCT International Search Report and Written Opinion for Int. App. No. PCT/US2017/019953, dated Aug. 4, 2017 21 pages.
PCT International Search Report and Written Opinion in International Appln. No. PCT/US2018/042640, dated Jan. 18, 2019, 19 pages.
Pereira et al., "Maximizing the Therapeutic Window of an Antimicrobial Drug by Imparting Mitochondrial Sequestration in Human Cells," *J. Am. Chem. Soc.*, Mar. 2011, 133(10):3260-3263.
Pham et al., "Truncated and constrained helical analogs of antimicrobial esculentin-2EM," *Bioorg & Med Chem Lett.*, 23(24):6717-20 (Dec. 2013).
Phelan et al., "A General Method for Constraining Short Peptides to an α-Helical Conformation," *J Am. Chem. Soc.*, Jan. 1997, 119:455-460.
Rose et al., "Potential Role of Epithelial Cell-Derived Histone H1 Proteins in Innate Antimicrobial Defense in the Human Gastrointestinal Tract," *Infect Immun.*, Jul. 1998, 66(7):3255-63.
Schafmeister et al., An All-Hydrocarbon Cross-Linking System for Enhancing the Helicity and Metabolic Stability of Peptides, *J Am Chem Soc.*, 2000, 122:5891-5892.
Shah et al., "The proteome targets of intracellular targeting antimicrobial peptides," *Proteomics*, Apr. 2016, 16(8):1225-37.

(56) References Cited

OTHER PUBLICATIONS

Shepard et al., "Single Turn Peptide Alpha Helices with Exceptional Stability in Water," *Journal of the American Chemical Society*, Feb. 2005, 127:2974-2983.

Spokoyny et al., "A Perfluoroaryl-Cysteine SNAr Chemistry Approach to Unprotected Peptide Stapling Bis-arylation stapling," *J. Am. Chem. Soc.*, 2013, 135(16):5946-5949.

Steinauer et al., "HOPS-dependent endosomal fusion required for efficient cytosolic delivery of therapeutic peptides and small proteins," *Proceedings of the National Academy of Sciences*, 2019, 116(2):512-521.

Stone et al., "Influence of hydrocarbon-stapling on membrane interactions of synthetic antimicrobial peptides," *Bioorg Med Chem.*, Mar. 2018, 26(6):1189-1196.

Strahl et al., "Bacterial membranes: structure, domains, and function," *Annual Review of Microbiology*, 2017, 71:519-538.

Sun et al., "Membrane permeability of hydrocarbon-cross-linked peptides," *Biophysical Journal*, 2013, 104(9):1923-1932.

Szu et al., "Laboratory and preliminary clinical characterization of Vi capsular polysaccharide-protein conjugate vaccines,"*Infect. Immun.*, Oct. 1994, 62(10):4440-4444.

Szu et al., "Relation between structure and immunologic properties of the Vi capsular polysaccharide," *Infect. Immun.*, Dec. 1991, 59(12):4555-4561.

Szu et al.. "Vi capsular polysaccharide-protein conjugates for prevention of typhoid fever. Preparation, characterization, and immunogenicity in laboratory animals," *J. Exp. Med.*, Nov. 1987, 166(5):1510-1524.

Thaker et al., "Synthetic Mimics of Antimicrobial Peptides with Immunomodulatory," *Responses, J. Am. Chem. Soc.*, Jul. 2012, 134(27):11088-11091.

The teaching material from the CUNY biology program https://web.archive.org/web/20000530152547/http://acadennic.brooklyn.cuny.edu/biology/bio4fv/page/sinnple.htnn, available May 2000.

Tjoeng et al., "Multiple peptide synthesis using a single support (MPS3)," *International Journal of Peptide and Protein Research*, 1990, 35(2):141-146.

Verstraelen et al., "Culture-independent analysis of vaginal microflora: the unrecognized association of Atopobium vaginae with bacterial vaginosis," *Am J. Obstet. and Gynecol.*, Oct. 2004, 191(14):1130-1132.

Walensky et al., "Activation of apoptosis in vivo by a hydrocarbon-stapled BH3 helix," *Science*, Sep. 2004, 305(5689):1466-1470.

Walensky et al., "Hydrocarbon-Stapled Peptides: Principles, Practice, and Progress," *J. Med. Chem.*, 2014, 57(15):6275-6288.

Wiegand et al., "Agar and broth dilution methods to determine the minimal inhibitory concentration (MIC) of antimicrobial substances," *Nat Protoc.*, 2008, 3(2):163-175.

Wilen et al., "Strategies in Optical Resolutions," *Tetrahedron*, 1977, 33:2725-2736.

Williams et al., "Asymmetric Synthesis of Monosubstituted and a,a-Disubstituted a-Amino Acids via Diastereoselective Glycine Enolate Alkylations," *J. Chem. Soc.*, 1991, 113:9276-9286.

Williams et al., "Efficient Asymmetric Synthesis Of N-tert-Butoxycarbonyl □-Aminoacids Using 4-tert-Butoxycarbonyl- 5,6-Diphenylmorpholin-2-One: (R)-(Ntert-butoxycarbonyl)allylglycine [(4-Pentenoic acid, 2-[[(1,1-dimethylethoxy)carbonyl]amino]-, (2R)-)]," *Org. Synth.*, 2003, 80:31-37.

Wimley, Describing the mechanism of antimicrobial peptide action with the interfacial activity model, *ACS Chem. Biol.* 5(10):905-917 (2010).

Xie et al., "Effect of proline position on the antimicrobial mechanism of buforin II," *Peptides*, 2011, 32:677-682.

Yampolsky et al., "The exchangeability of amino acids in proteins," *Genetics*, 2005, 170:1459-1472.

Yang et al., "Calculation of Protein Conformation from Circular Dichroism," *Methods Enzymol.*, 1986, 130:208-269.

Yi et al., "Solution structure of an antimicrobial peptide buforin II," *FEBS Letters*, Nov. 1996, 398(1):87-90.

Yin et al., "Alpha helix mimetics in drug delivery," Drug Discovery Research: New Frontiers in the Post-Genomic Era, Huang ed., 2007, Chapter 11: pp. 280-298.

Zasloff, "Antimicrobial peptides of multicellular organisms," *Nature*, Jan. 2002, 415(6870):389-395.

Zboinska et al., "Antibacterial activity of phosphono dipeptldes based on 1-amino-1-meihylethanephosphonic acid," *FEMS Microbiology Letters*, 1990, (70):23-28.

U.S. Appl. No. 16/551,102, filed Aug. 26, 2019, Walensky.
U.S. Appl. No. 15/201,235, 2017/0015716, U.S. Pat. No. 10,464,975, filed Jul. 1, 2016, Walensky.
U.S. Appl. No. 16/551,102, 2020/0231638, filed Aug. 26, 2019, Walensky.
U.S. Appl. No. 17/091,541, filed Nov. 6, 2020, Walensky.
U.S. Appl. No. 17/349,335, filed Jun. 16, 2021, Walensky.
U.S. Appl. No. 15/445,502, 2017/0247423, filed Feb. 28, 2017, Walensky.
U.S. Appl. No. 16/813,528, 2020/0308236, filed Mar. 3, 2020, Walensky.

* cited by examiner

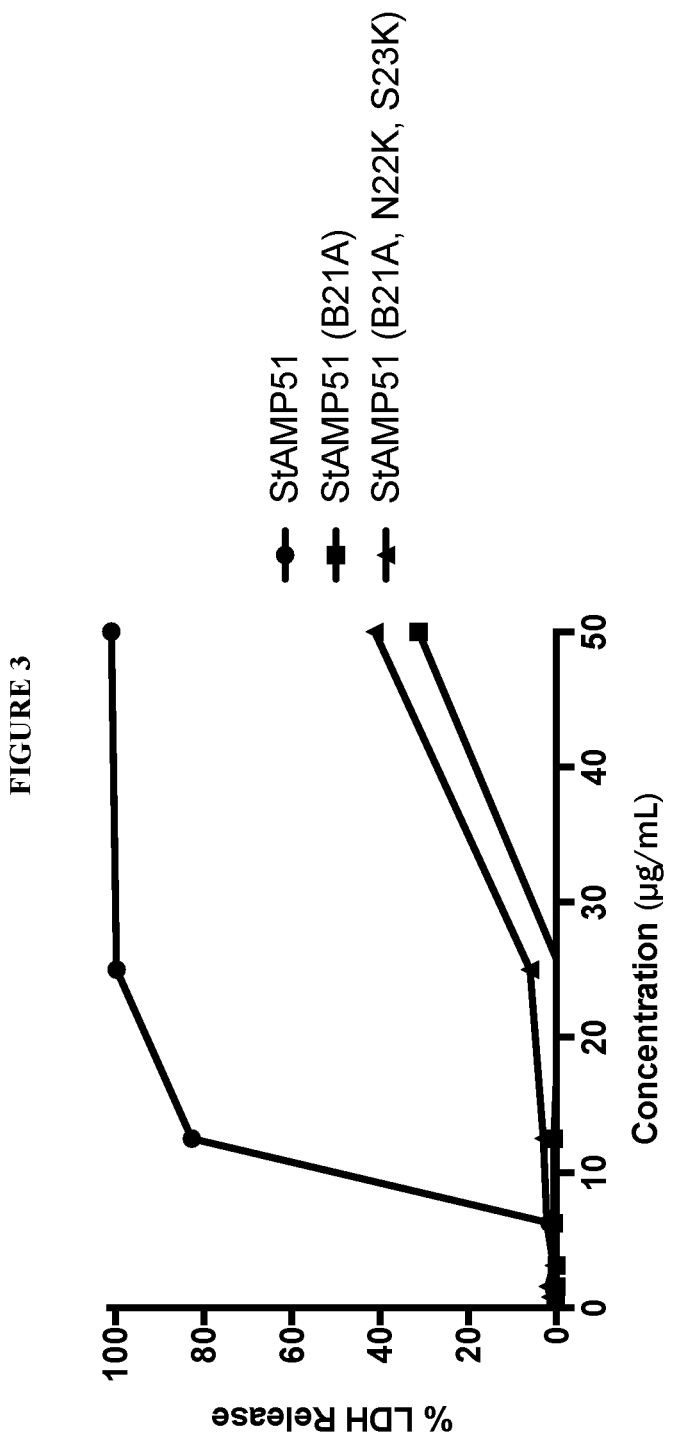

FIGURE 4

Drug Sensitivity      MIC (μg/ml)

| Strain | Microorganism | Amp | Ceftaz | CTX | Cipro | Gent | Mero | Tob | StAMP51* | StAMP51 2.0** | Pleu(i+4)1,15(A9K) |
|---|---|---|---|---|---|---|---|---|---|---|---|
| 0001 | Escherichia coli | R | R | R | R | S | R | R | 1.56 | 1.56 | 3.12 |
| 0002 | Enterobacter cloacae | R | R | R | R | I | R | R | 1.56 | 1.56 | 3.12 |
| 0003 | Klebsiella pneumoniae | R | R | R | R | S | R | R | 3.12 | 3.12 | 3.12 |
| 0004 | Klebsiella pneumoniae | R | R | R | R | S | R | R | 6.25 | 12.5 | 3.12 |
| 0005 | Klebsiella pneumoniae | R | R | R | R | S | R | R | 3.12 | 6.25 | 3.12 |
| 0006 | Escherichia coli | R | R | R | R | R | R | R | 3.12 | 3.12 | 3.12 |
| 0010 | Klebsiella pneumoniae | R | R | R | S | S | S | S | 2.23 | 3.12 | 3.12 |
| 0030 | Shighella sonnei | R | S | S | S | S | S | S | 1.56 | 0.78 | 3.12 |
| 0031 | S. typhimurium | S | S | S | S | S | S | S | 6.25 | 12.5 | 3.12 |
| 0112 | Klebsiella pneumoniae | R | R | R | R | R | R | R | 4.38 | 12.5 | 3.12 |
| 0113 | Klebsiella pneumoniae | R | R | R | R | R | R | R | 3.12 | 12.5 | 3.12 |
| 0114 | Escherichia coli | R | R | R | R | S | R | I | 1.56 | 1.56 | 3.12 |
| 0127 | Salmonella senftenberg | R | R | R | R | R | R | R | 3.12 | 1.56 | 3.12 |

Amp=Ampicillin, Ceftaz=Ceftazidime, CTX=Ceftriaxone, Cipro=Ciprofloxacin, Gent=Gentamicin, Mero=Meropenem, Tob=Tobramycin; S=Susceptible, I=Intermediate, R=Resistant;
StAMP51*=Mag(i+4)1,15(A9K);
StAMP51 2.0**=Mag(i+4)1,15(A9K,B21A,N22K,S23K).

STABILIZED ANTI-MICROBIAL PEPTIDES FOR THE TREATMENT OF ANTIBIOTIC-RESISTANT BACTERIAL INFECTIONS

CROSS-REFERENCE TO RELATED APPLICATIONS

This application is a U.S. National Stage application, and claims priority of International Application No. PCT/US2018/042640, filed Jul. 18, 2018, which claims the benefit of priority of U.S. Provisional Application Nos. 62/644,114 and 62/534,464 filed on Mar. 16, 2018, and Jul. 19, 2017, respectively. The contents of each of these applications are incorporated by reference herein in their entireties.

TECHNICAL FIELD

This disclosure relates to methods of treating antibiotic-resistant bacterial infections (e.g., Gram-negative or Gram-positive) in a human, animal, or plant in need thereof using stabilized (e.g., stapled and/or stitched) antimicrobial peptides (StAMP) (e.g., hydrocarbon-stapled and/or stitched antimicrobial peptides), methods for generating such peptides, and solutions, products, reagents, devices, and materials coated or comprising such peptides.

BACKGROUND

Anti-microbial peptides (AMPs) are an evolutionarily conserved class of proteins that form an essential line of defense against microbial invasion. These peptides are produced by many disparate organisms and have been found to exhibit a wide spectrum of activity against bacteria, fungi (including yeasts), protozoa (including parasites), and viruses. The rise in antibiotic-resistance across the globe has become a major threat to modern healthcare. As the number of newly approved antibiotics has dwindled over the past decade, the need for novel agents to combat drug-resistant microbes has greatly increased. Never has the need for new treatment options been more evident that at the present time, when the evolution of resistance in bacteria has outpaced modern drug development efforts. In light of these dangerous developments, there is a great need for new agents that overcome antibiotic-resistance in Gram-negative or Gram-positive bacteria.

SUMMARY

The present disclosure provides structurally stabilized peptides related to (e.g., sharing sequence homology with) anti-microbial peptides (AMPs), and methods for using such stabilized peptides as therapeutic and/or prophylactic agents. Methods are also provided for designing stabilized (e.g., stapled and/or stitched) anti-microbial peptides (StAMPs) (e.g., hydrocarbon-stapled and/or stitched anti-microbial peptides) that are selectively lytic/cytotoxic to gram-negative or gram-positive bacteria, allowing for prophylactic or therapeutic use of StAMPs (e.g., hydrocarbon-stapled and/or stitched anti-microbial peptides) without mammalian membrane disruption and/or cytotoxicity. Also featured are methods of using the StAMPS disclosed herein treatment of bacterial infections (e.g., colistin-resistant) in plants (e.g., crops, trees, flowering plants) as well as livestock (e.g., pigs, chickens, cows). Further, methods of reducing renal toxicity of a StAMP are disclosed.

In one aspect, this disclosure features a method of treating an antibiotic-resistant bacterial infection in a human subject, an animal (e.g., livestock), or a plant (e.g., a crop, a tree) in need thereof. The methods involve administering an effective amount of a stabilized (e.g., stapled and/or stitched) antimicrobial peptide (StAMP) (e.g., hydrocarbon-stapled and/or stitched anti-microbial peptide) described herein to the human, animal, or plant that has, or is at risk of developing, the antibiotic-resistant bacterial infection. In some embodiments, the antibiotic-resistant bacterial infection is an antibiotic-resistant Gram-negative bacterial infection. In some embodiments, the antibiotic that the bacteria is resistant to is an antibiotic selected from the group consisting of: colistin, carbapenem, an aminoglycoside, vancomycin, methicillin, clarithromycin, cephalosporin, penicillin, ampicillin, fluoroquinolone, tetracycline, ceftazidime, ceftriaxone, ciprofloxacin, gentamicin, meropenem, tobramycin, and a β-lactam. In other embodiments, the antibiotic-resistant bacterial infection is an antibiotic-resistant Gram-positive bacterial infection. In some embodiments, the antibiotic that the bacteria is resistant to is an antibiotic selected from the group consisting of: methicillin, penicillin, vancomycin, and an aminoglycoside. In one embodiment, when the method relates to treating a plant bacterial infection, the antibiotic that the bacteria are resistant to is streptomycin or oxytetracycline.

In another aspect, this disclosure relates to methods for treating antibiotic-resistant gram-negative bacterial infections in a human subject, an animal (e.g., livestock), or a plant (e.g., a crop, a tree, a flowering plant) in need thereof. The methods involve administering an effective amount of a StAMP (e.g., hydrocarbon-stapled and/or stitched anti-microbial peptide) described herein to the human, animal, or plant that has, or is at risk of developing, the antibiotic-resistant bacterial infection. In some embodiments, the antibiotic that the bacteria are resistant to is selected from the group consisting of: colistin, carbapenem, an aminoglycoside, vancomycin, methicillin, clarithromycin, cephalosporin, penicillin, ampicillin, fluoroquinolone, tetracycline, ceftazidime, ceftriaxone, ciprofloxacin, gentamicin, meropenem, tobramycin, and a β-lactam.

In one specific aspect, this disclosure provides methods of treating a Gram-negative colistin-resistant bacterial infection in a human subject, an animal (e.g., livestock), or a plant (e.g., a crop, a tree) in need thereof that include administering a therapeutically effective amount of a stabilized (e.g., stapled and/or stitched) antimicrobial peptide (StAMP) (e.g., hydrocarbon-stapled and/or stitched anti-microbial peptide) to the subject that has, or is at risk of developing, the Gram-negative colistin-resistant bacterial infection.

In one specific aspect, this disclosure provides methods of treating a Gram-negative carbapenem-resistant bacterial infection in a human subject, an animal (e.g., livestock), or a plant (e.g., a crop, a tree) in need thereof that include administering a therapeutically effective amount of a stabilized (e.g., stapled and/or stitched) antimicrobial peptide (StAMP) (e.g., hydrocarbon-stapled and/or stitched anti-microbial peptide) to the subject that has, or is at risk of developing, the Gram-negative carbapenem-resistant bacterial infection.

In one specific aspect, this disclosure provides methods of treating a Gram-positive carbapenem-resistant bacterial infection in a human subject, an animal (e.g., livestock), or a plant (e.g., a crop, a tree) in need thereof that include administering a therapeutically effective amount of a stabilized (e.g., stapled and/or stitched) antimicrobial peptide (StAMP) (e.g., hydrocarbon-stapled and/or stitched antimicrobial peptide) to the subject that has, or is at risk of developing, the Gram-positive carbapenem-resistant bacterial infection. In some embodiments, the method further involves administering to the subject daptomycin and/or vancomycin.

In another aspect, this disclosure relates to methods for treating antibiotic-resistant gram-positive bacterial infections in a human subject, an animal (e.g., livestock), or a plant (e.g., a crop, a tree, a flowering plant) in need thereof. The methods involve administering an effective amount of a StAMP (e.g., hydrocarbon-stapled and/or stitched anti-microbial peptide) described herein to the human, animal, or plant that has, or is at risk of developing, the antibiotic-resistant bacterial infection. In some embodiments, the antibiotic that the bacteria are resistant to is selected from the group consisting of: methicillin, penicillin, vancomycin, and an aminoglycoside.

In one specific aspect, this disclosure provides methods of treating a Gram-positive methicillin-resistant bacterial infection in a human subject, an animal (e.g., livestock), or a plant (e.g., a crop, a tree) in need thereof that include administering a therapeutically effective amount of a stabilized (e.g., stapled and/or stitched) antimicrobial peptide (StAMP) (e.g., hydrocarbon-stapled and/or stitched antimicrobial peptide) to the subject that has, or is at risk of developing, the Gram-positive methicillin-resistant bacterial infection.

In certain embodiments of the above aspects, the StAMP is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin. To be "based on or derived from the scaffold of a peptide" means that at least two (e.g., 2, 3, 4, 5, 6) amino acids of these peptides (e.g., any one of SEQ ID NOs.:4, 5, 6, 8, 10, 12, 14, 16, 18, 20, 22, 24, 26, 28, 30, and 32) that are spaced at least 2, 3, or 6 amino acids apart are replaced with non-natural amino acids with olefinic side chains that can form a staple or a stitch (e.g., a hydrocarbon-staple or stitch). Examples of such peptides are provided in SEQ ID NOs.: 1-3, 34, and 36-43. In certain embodiments, the StAMP (e.g., hydrocarbon-stapled and/or stitched antimicrobial peptide) is derived from the magainin scaffold (i.e., SEQ ID NO:4). In certain embodiments, the StAMP (e.g., hydrocarbon-stapled and/or stitched antimicrobial peptide) is derived from the pleurocidin scaffold (i.e., SEQ ID NO:6).

In certain embodiments of the above aspects, the StAMP comprises or consists of the amino acid sequence set forth in any one of SEQ ID Nos.: 1-3, 34, 35 or 36-43 except for 1 to 5 (i.e., 1, 2, 3, 4, or 5) amino acid substitutions, insertions, and/or deletions within SEQ ID Nos.: 1-3, 34, 35 or 36-43. In certain embodiments one or more of these amino substitutions are conservative amino acid substitutions. In certain embodiments, the StAMP comprises or consists of a StAMP based on or derived from the scaffold of a peptide having the amino acid sequence set forth in any one of SEQ ID Nos.:4-33 except for 1 to 5 (i.e., 1, 2, 3, 4, or 5) amino acid substitutions, insertions, and/or deletions within SEQ ID Nos.: 4-33. In some embodiments, the StAMP comprises or consists of the sequence of any one of SEQ ID Nos.: 7, 9, 11, 13, 15, 17, 19, 21, 23, 25, 27, 29, 31, 33, 34, or 35 except for 1 to 5 (i.e., 1, 2, 3, 4, or 5) amino acid substitutions, insertions, and/or deletions within SEQ ID Nos.: 7, 9, 11, 13, 15, 17, 19, 21, 23, 25, 27, 29, 31, 33, 34, or 35. In certain embodiments, one or more of these amino substitutions are conservative amino acid substitutions.

It is important to note that significant variability is permitted in the sequences disclosed in this application (e.g., SEQ ID Nos.: 1-43) as long as the sequences have the desired hydrophobicity and positive charge at specific interfaces rather than specific amino acid sequence compositions. That is, this application relates, in part, to membrane disruptive peptides—so, as long as the peptides are able to engage a membrane, albeit specific to some (bacterial), but not others (mammalian-especially human) membranes, significant sequence variability is permitted and envisioned.

In certain embodiments of the above aspects, the StAMP comprises or consists of an amino acid sequence that is at least 45%, 50%, 55%, 60%, 65%, 70%, 75%, 80%, 85%, 90%, 91%, 92%, 93%, 94%, 95%, 96%, 97%, 98%, or 99% identical to the amino acid sequence set forth in any one SEQ ID NO: 1, 2, 3 or 36-43. In certain embodiments, the conservative amino acid substitution(s) made to any of these sequences (i.e., SEQ ID Nos.: 1-3 or 36-43) are not considered as being different/non-identical when determining the above-referenced % identity between the sequences. In some embodiments, the StAMP comprises or consists of an amino acid sequence that is at least 45%, 50%, 55%, 60%, 65%, 70%, 75%, 80%, 85%, 90%, 91%, 92%, 93%, 94%, 95%, 96%, 97%, 98%, or 99% identical to the amino acid sequence of any one of SEQ ID Nos.: 7, 9, 11, 13, 15, 17, 19, 21, 23, 25, 27, 29, 31, 33, 34, or 35. In certain embodiments, the conservative amino acid substitution(s) made to any of these sequences (i.e., SEQ ID Nos.: 7, 9, 11, 13, 15, 17, 19, 21, 23, 25, 27, 29, 31, 33, 34, or 35) are not considered as being different/non-identical when determining the above-referenced % identity between the sequences. In certain embodiments, the StAMP comprises or consists of a StAMP based on or derived from the scaffold of a peptide having an amino acid sequence that is at least 45%, 50%, 55%, 60%, 65%, 70%, 75%, 80%, 85%, 90%, 91%, 92%, 93%, 94%, 95%, 96%, 97%, 98%, or 99% identical to the amino acid sequence set forth in any one SEQ ID NO: 4-33. In certain embodiments, the conservative amino acid substitution(s) made to any of these sequences (i.e., SEQ ID Nos.: 4-33) are not considered as being different/non-identical when determining the above-referenced % identity between the sequences.

In certain embodiments of the above aspects, the StAMP comprises or consists of the amino acid sequence set forth in any one SEQ ID NO: 1, 2, 3, 34, 35, 36, 37, 38, 39, 40, 41, 42, or 43. In some embodiments, the StAMP comprises or consists of the sequence of any one of SEQ ID Nos.: 7, 9, 11, 13, 15, 17, 19, 21, 23, 25, 27, 29, 31, or 33. In certain instances, these sequences may be modified to include additional, e.g., 2 or more (e.g., 3, 4, 5, 6) non-natural olefinic side chain-containing amino acids that can form a hydrocarbon staple or stitch. In some embodiments, the StAMP comprises or consists of the sequence of any one of SEQ ID Nos.: 4-6, 8, 10, 12, 14, 16, 18, 20, 22, 24, 26, 28, 30, or 32 which are modified to have one to six (e.g., 1, 2, 3, 4, 5, or 6) "X's". The position of the "X" (i.e., the non-natural amino acid with olefinic side chains) in these sequences can be varied as long as the X's that are involved in forming a staple/stitch are separated by 2, 3, or 6 amino acids. In one embodiment, the X's that are involved in forming a staple/stitch are separated by 3 amino acids. In another embodiment, the X's that are involved in forming a staple/stitch are separated by 6 amino acids. In yet another embodiment, two of X's that are involved in forming a staple are separated by 3 amino acids; and a second two X's that are involved in forming a staple are separated by 3 amino acids. In certain embodiments, the "X's" in these sequences that are involved in forming a staple/stitch can be the same non-natural amino acid. In other embodiments, the "X's" in these sequences that are involved in forming a staple/stitch are different non-natural amino acids. In certain instances, "X" is one of (S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, or (S)-2-(2-propenyl)Ala-OH. In certain embodiments, if a sequence has two "X's" both X's are (S)-2-(4-pentenyl)Ala-OH. In certain embodiments, if a sequence has two "X's" both X's are (R)-2-(4-pentenyl)Ala-OH. In certain embodiments, if a sequence has two "X's" both X's are (R)-2-(7-octenyl)Ala-OH. In certain embodiments, if a sequence has two "X's" both X's are (S)-2-(7-octenyl)Ala-OH. In certain embodiments, if a sequence has two "X's" both X's are 2-amino-2-(pent-4-enyl)hept-6-enoic acid. In certain embodiments, if a sequence has two "X's" both X's are (R)-2-(2-propenyl)Ala-OH. In certain embodiments, if a sequence has two "X's" both X's are (R)-2-(2-propenyl)Ala-OH. In certain embodiments, if a sequence has two "X's" both X's are (S)-2-(2-propenyl)Ala-OH. In certain embodiments, if a sequence has two "X's" both X's are different non-natural amino acids and can, e.g., be selected from the group consisting of S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, and (S)-2-(2-propenyl)Ala-OH. In certain instances, if the two X's are separated by 3 amino acids, the two X's can be different non-natural residues, e.g., the first X is (R)-2-(2-propenyl)Ala-OH or (S)-2-(2-propenyl)Ala-OH and the second X is (S)-2-(2-propenyl)Ala-OH or (R)-2-(2-propenyl)Ala-OH. In certain instances, the "X's" that are in SEQ ID Nos.: 1-3, 7, 9, 11, 13, 15, 17, 19, 21, 23, 25, 27, 29, 31, 33, 36, 37, 38, 39, 40, 41, 42, or 43, or inserted into SEQ ID Nos.: 4-6, 8, 10, 12, 14, 16, 18, 20, 22, 24, 26, 28, 30, or 32 can be any residue/substance that permits formation of a staple and/or stitch. In other words, the staple and/or stitch does not need to be a hydrocarbon-staple and/or stitch. Methods of performing different types of stapling are well known in the art (see, e.g., *Lactam stapling*: Shepherd et al., *J. Am. Chem. Soc.*, 127:2974-2983 (2005); *Triazole stapling*: Kawamoto et al., *J. Med. Chem.*, 55:1137-1146 (2011); *UV-cycloaddition stapling*: Madden et al., *Bioorg. Med. Chem. Lett.*, 21:1472-1475 (2011); *Disulfide stapling*: Jackson et al., *Am. Chem. Soc.*, 113:9391-9392 (1991); *Oxime stapling*: Haney et al., *Chem. Commun.*, 47:10915-10917 (2011); *Thioether stapling*: Brunel and Dawson, *Chem. Commun.*, 552-2554 (2005); *Photoswitchable stapling*: J. R. Kumita et al., *Proc. Natl. Acad. Sci. U.S.A*, 97:3803-3808 (2000); *Double-click stapling*: Lau et al., *Chem. Sci.*, 5:1804-1809 (2014); *Bis-lactam stapling*: J. C. Phelan et al., *J. Am. Chem. Soc.*, 119:455-460 (1997); and *Bis-arylation stapling*: A. M. Spokoyny et al., *J. Am. Chem. Soc.*, 135:5946-5949 (2013)). In certain instances, the "X's" that are in SEQ ID Nos.: 1-3, 34, 35, 7, 9, 11, 13, 15, 17, 19, 21, 23, 25, 27, 29, 31, 33 or 36-43, or inserted into SEQ ID Nos.: 4-6, 8, 10, 12, 14, 16, 18, 20, 22, 24, 26, 28, 30, or 32 can be any residue that permits formation of a hydrocarbon staple and/or stitch. In certain instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are lactam stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, 32 or 36-43 are triazole stapled. In other instances, the peptides with the sequences recited in SEQ ID NOs.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are stapled using a UV-cycloaddition staple. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are disulfide stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are oxime stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are thioether stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 comprise a photoswitchable staple. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are double-click stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are bis-lactam stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 comprise a bis-arylation staple. In certain embodiments, the StAMP comprises or consists of the amino acid sequence set forth in, or a modified version (i.e., a sequence comprising 2 or more (e.g., 3, 4, 5, 6) non-natural olefinic side chain-containing amino acids that can form a hydrocarbon staple) of, an amino sequence set forth in any one SEQ ID NO: 4-33.

In some embodiments of any of the methods described herein, the StAMP is 6 to 100 amino acids in length (e.g., between 6 and 40 amino acids in length (e.g., between 6 and 10 amino acids in length, between 6 and 15 amino acids in length, between 6 and 20 amino acids in length, between 6 and 25 amino acids in length, between 6 and 30 amino acids in length, between 6 and 35 amino acids in length; between 10 and 15 amino acids in length, between 10 and 20 amino acids in length, between 10 and 25 amino acids in length, between 10 and 30 amino acids in length, between 10 and 35 amino acids in length; between 15 and 20 amino acids in length, between 15 and 25 amino acids in length, between 15 and 30 amino acids in length, between 15 and 35 amino acids in length; between 15 and 40 amino acids in length; between 20 and 25 amino acids in length, between 20 and 30 amino acids in length, between 20 and 35 amino acids in length; between 20 and 40 amino acids in length; between 30 and 35 amino acids in length; between 30 and 40 amino acids in length; or between 35 and 40 amino acids in length).

In certain embodiments, the subject is a human. In certain embodiments, the subject has developed an infection with antibiotic-resistance to at least one (e.g., 1, 2, 3, 4, 5, 6, 7, 8, 9, or 10) other class of antibiotic. In some embodiments, the at least one (e.g., 1, 2, 3, 4, 5, 6, 7, 8, 9, or 10) other class of antibiotic is selected from the group consisting of: carbapenem, an aminoglycoside, vancomycin, methicillin, clarithromycin, cephalosporin, penicillin, ampicillin, fluoroquinolone, tetracycline, ceftazidime, ceftriaxone, ciprofloxacin, gentamicin, meropenem, tobramycin, and a β-lactam. In certain embodiments, the at least one other class of antibiotic is carbapenem. In certain embodiments, the at least one other class of antibiotic is clarithromycin. In certain embodiments, the at least one other class of antibiotic is cephalosporin. In certain embodiments, the at least one other class of antibiotic is fluoroquinolone. In certain embodiments, the at least one other class of antibiotic is methicillin. In certain embodiments, the at least one other class of antibiotic is vancomycin. In certain embodiments, the at least one other class of antibiotic is ceftriaxone. In certain embodiments, the at least one other class of antibiotic is ciprofloxacin. In certain embodiments, the at least one other class of antibiotic is gentamicin. In certain embodiments, the at least one other class of antibiotic is meropenem. In certain embodiments, the at least one other class of antibiotic is tobramycin. In certain embodiments, the at least one other class of antibiotic is methicillin and vancomycin. In certain embodiments, the at least one other class of antibiotic is cephalosporin and fluoroquinolone.

In some embodiments, the subject has a Gram-negative antibiotic-resistant bacterial infection (e.g., a chronic infection). In certain cases, the antibiotic the bacteria is resistant to is selected from the group consisting of: colistin, carbapenem, an aminoglycoside, vancomycin, methicillin, clarithromycin, cephalosporin, penicillin, ampicillin, fluoroquinolone, tetracycline, and a β-lactam. In some embodiments, the subject has a chronic Gram-negative colistin-resistant bacterial infection. In some embodiments, the Gram-negative colistin-resistant bacterial infection is an *A. baumannii* infection. In some embodiments, the Gram-negative colistin-resistant bacterial infection is an *E. coli* infection. In some embodiments, the Gram-negative colistin-resistant bacterial infection is a *Klebsiella pneumoniae* infection. In some embodiments, the Gram-negative colistin-resistant bacterial infection is an infection selected from the group consisting of a *Pseudomonas* infection, a *Neisseria* infection, a *Chlamydia* infection, a *Yersinia* infection, a *Proteus* infection, an *Enterobacter* infection, a *Serratia* infection, a *Helicobacter* infection, a *Salmonella* infection, a *Salmonella* infection, a *Shigella*, a *Moraxella* infection, a *Stenotrophomonas*, a *Klebsiella* infection, and a *Legionella* infection. In some embodiments, the Gram-negative colistin-resistant bacterial infection is an infection selected from the group consisting of a *Pseudomonas aeruginosa* infection, a *Neisseria gonorrhoeae* infection, a *Chlamydia trachomatis* infection, a *Yersinia pestis* infection, a *Proteus mirabilis* infection, an *Enterobacter cloacae* infection, a *Serratia marcescens* infection, a *Helicobacter pylori* infection, a *Salmonella enteritidis* infection, a *Salmonella typhi* infection, a *Shigella* infection, a *Moraxella* infection, a *Stenotrophomonas* infection, a *Bdellovibrio* infection, an acetic acid bacterial infection, a *Klebsiella pneumoniae* infection, and a *Legionella pneumophila* infection. In some embodiments, the Gram-negative colistin-resistant bacterial infection is from a Gram-negative bacterium that contains a MCR-1 plasmid. In some embodiments, the Gram-negative bacterium that contains a MCR-1 plasmid is *E. coli*.

In some embodiments, the subject has a Gram-positive antibiotic-resistant bacterial infection (e.g., a chronic infection). In certain cases, the antibiotic the bacteria is resistant to is selected from the group consisting of: methicillin, penicillin, vancomycin, and an aminoglycoside. In some embodiments, the subject has a chronic Gram-positive methicillin-resistant bacterial infection. In some embodiments, the subject has a chronic Gram-positive penicillin-resistant bacterial infection. In some embodiments, the subject has a chronic Gram-positive vancomycin-intermediate or vancomycin-resistant bacterial infection. In some embodiments, the subject has a chronic Gram-positive aminoglycoside-resistant bacterial infection. In some embodiments, the Gram-positive antibiotic-resistant infection is from a bacterium selected from the group consisting of *Actinomyces israelii*, *Actinomyces gerencseriae*, *Propionibacterium propionicus*, *Bacillus anthracis*, *Arcanobacterium haemolyticum*, *Bacillus cereus*, bacterial vaginosis microbiota, *Clostridium botulinum*, *Mycobacterium ulcerans*, Group A *Streptococcus* and *Staphylococcus*, *Clostridium difficile*, *Corynebacterium diphtheria*, *Enterococcus species*, *Clostridium perfringens*, other *Clostridium* species, *Streptococcus pyogenes*, *Streptococcus agalactiae*, *Mycobacterium leprae*, *Mycobacterium lepromatosis*, *Listeria monocytogenes*, *Nocardia asteroides*, *Nocardia species*, *Streptococcus pneumoniae*, *Staphylococcus aureus*, *Staphylococcus species*, *Clostridium tetani*, *Mycobacterium tuberculosis*, *Yersinia pseudotuberculosis*, and *Yersinia enterocolitica*.

In some embodiments, where the StAMP is administered intravenously, the StAMP has a hemolytic activity that is less than 50% (e.g., less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, between 0-20%, 0-18%, 0-16%, 0-14%, 0-12%, 0-10%, 0-8%, 0-6%, 0-4%, 0-2%, 0-1%, or 1-20%). In some embodiments, the StAMP has a hemolytic activity that is less than 10% (e.g., less than 9%, less than 8%, less than 7%, less than 6%, less than 5%, less than 4%, less than 3%, less than 2%, or less than 1%). In some embodiments, the StAMP has a hemolytic activity that is less than 5% (e.g., less than 4%, less than 3%, less than 2%, or less than 1%). In some instances for these embodiments, the StAMP is at a concentration of 25 μg/mL or less.

In some embodiments, where the StAMP is administered by a non-intravenous route (e.g., topically, intranasally, via inhalation, orally, rectally, vaginally), where the StAMP does not need to enter the bloodstream to reach the pathogen, the StAMP can have any hemolytic activity. In some instances, the StAMP has a hemolytic activity that is greater than 20% but less than 50% (e.g., 20%-49%, 25%-49%, 30%-49%, 35%-49%, 40%-49%, less than 45%, less than 40%, less than 35%, less than 30%, or less than 25%). In other embodiments, where the StAMP is administered by a non-intravenous route, the StAMP has a hemolytic activity that is less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, or less than 0.5%). In some instances, the StAMP has a hemolytic activity that is greater than 20% but less than 100%. In some instances, the StAMP has a hemolytic activity that is greater than 20% but less than 95%. In some instances, the StAMP has a hemolytic activity that is greater than 20% but less than 90%. In some instances, the StAMP has a hemolytic activity that is greater than 20% but less than 80%. In some instances, the StAMP has a hemolytic activity that is greater than 20% but less than 70%. In some instances, the StAMP has a hemolytic activity that is greater than 20% but less than 60%. In some instances, the StAMP has a hemolytic activity that is greater than 20% but less than 50%.

In some embodiments, the StAMP has a minimum inhibitory concentration for *A. baumannii* of less than 25 µg/mL (e.g., less than 20 µg/mL, less than 15 µg/mL, less than 10 µg/mL, less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, or less than 0.5 µg/mL). In some embodiments, the StAMP has a minimum inhibitory concentration for *A. baumannii* of less than 2.5 µg/mL (e.g., less than 2.0 µg/mL, less than 1.5 µg/mL, less than 1.0 µg/mL, or less than 0.5 µg/mL). In some embodiments, the StAMP has a minimum inhibitory concentration for *A. baumannii* of less than 2.0 µg/mL (e.g., less than 1.5 µg/mL, less than 1.0 µg/mL, or less than 0.5 µg/mL). In certain embodiments, the MIC is determined using the method described in Example 1.

In some embodiments, the StAMP has a minimum inhibitory concentration for *Klebsiella pneumoniae* of less than 25 µg/mL (e.g., less than 20 µg/mL, less than 15 µg/mL, less than 10 µg/mL, less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, or less than 0.5 µg/mL). In some embodiments, the StAMP has a minimum inhibitory concentration for *Klebsiella pneumoniae* of less than 2.5 µg/mL (e.g., less than 2.0 µg/mL, less than 1.5 µg/mL, less than 1.0 µg/mL, or less than 0.5 µg/mL). In some embodiments, the StAMP has a minimum inhibitory concentration for *Klebsiella pneumoniae* of less than 2.0 µg/mL (e.g., less than 1.5 µg/mL, less than 1.0 µg/mL, or less than 0.5 µg/mL). In certain embodiments, the MIC is determined using the method described in Example 1.

In some embodiments, the StAMP has a minimum inhibitory concentration for 5 *E. coli* of less than 25 µg/mL (e.g., less than 20 µg/mL, less than 15 µg/mL, less than µg/mL, less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, or less than 0.5 µg/mL). In some embodiments, the StAMP has a minimum inhibitory concentration for *E. coli* of less than 2.0 µg/mL (e.g., less than 1.5 µg/mL, less than 1.0 µg/mL, or less than 0.5 µg/mL). In certain embodiments, the MIC is determined using the method described in Example 1.

In some embodiments, the StAMP has a minimum inhibitory concentration for a colistin-resistant Gram-negative bacterium of less 25 µg/mL (e.g., less than 20 µg/mL, less than 15 µg/mL, less than 10 µg/mL, less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, or less than 0.5 µg/mL). In some embodiments, the StAMP has a minimum inhibitory concentration for a colistin-resistant Gram-negative bacterium of less than 2.5 µg/mL (e.g., less than 2.0 µg/mL, less than 1.5 µg/mL, less than 1.0 µg/mL, or less than 0.5 µg/mL). In some embodiments, the StAMP has a minimum inhibitory concentration for a colistin-resistant Gram-negative bacterium of less than 2.0 µg/mL (e.g., less than 1.5 µg/mL, less than 1.0 µg/mL, or less than 0.5 µg/mL). In certain embodiments, the MIC is determined using the method described in Example 1.

In some embodiments, the Gram-negative colistin-resistant bacterium is *A. baumannii, E. coli, Pseudomonas aeruginosa, Neisseria gonorrhoeae, Chlamydia trachomatis, Yersinia pestis, Proteus mirabilis, Enterobacter cloacae, Serratia marcescens Helicobacter pylori, Salmonella enteritidis, Salmonella typhi, Shigella, Moraxella, Stenotrophomonas, Bdellovibrio*, an acetic acid bacterium, *Klebsiella pneumoniae*, and *Legionella pneumophila*, or a Gram-negative bacterium that contains a MCR-1 plasmid.

In some embodiments, the StAMP has a minimum inhibitory concentration for a Gram-positive antibiotic-resistant bacterium of less than 25 µg/mL (e.g., less than 20 µg/mL, less than 15 µg/mL, less than 10 µg/mL, less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, or less than 0.5 µg/mL). In some embodiments, the StAMP has a minimum inhibitory concentration for a Gram-positive antibiotic-resistant of less than 2.5 µg/mL (e.g., less than 2.0 µg/mL, less than 1.5 µg/mL, less than 1.0 µg/mL, or less than 0.5 µg/mL). In some embodiments, the StAMP has a minimum inhibitory concentration for a Gram-positive antibiotic-resistant of less than 2.0 µg/mL (e.g., less than 1.5 µg/mL, less than 1.0 µg/mL, or less than 0.5 µg/mL). In certain embodiments, the MIC is determined using the method described in Example 1.

In some embodiments, the Gram-positive antibiotic-resistant bacterium is *Actinomyces israelii, Actinomyces gerencseriae, Propionibacterium propionicus, Bacillus anthracis, Arcanobacterium haemolyticum, Bacillus cereus*, bacterial vaginosis microbiota, *Clostridium botulinum, Mycobacterium ulcerans*, Group A *Streptococcus* and *Staphylococcus, Clostridium difficile, Corynebacterium diphtheria, Enterococcus species, Clostridium perfringens*, other *Clostridium* species, *Streptococcus pyogenes, Streptococcus agalactiae, Mycobacterium leprae, Mycobacterium lepromatosis, Listeria monocytogenes, Nocardia asteroides, Nocardia species, Streptococcus pneumoniae, Staphylococcus aureus, Staphylococcus species, Clostridium tetani, Mycobacterium tuberculosis, Yersinia pseudotuberculosis*, or *Yersinia enterocolitica*. In certain embodiments, the Gram-positive bacterium is methicillin-resistant. In certain embodiments, the Gram-positive bacterium is penicillin-resistant. In certain embodiments, the Gram-positive bacterium is methicillin-resistant. In certain embodiments, the Gram-positive bacterium is vancomycin-intermediate or vancomycin-resistant. In certain embodiments, the Gram-positive bacterium is resistant to aminoglycosides.

In some embodiments of any of the methods described herein, the StAMP has a hemolytic activity of less than 5% (e.g., less than 4%, less than 3%, less than 2%, less than 1%, or less than 0.5%, or 0.5-5%), and a minimum inhibitory concentration for a Gram-negative colistin-resistant bacterium of less than 3.0 µg/mL (e.g., less than 2.5 µg/mL, less than 2.0 µg/mL, less than 1.5 µg/mL, less than 1.0 µg/mL, less than 0.5 µg/mL, or 0.5-3.0 µg/mL). In certain embodiments, the MIC is determined using the method described in Example 1.

In some embodiments, the StAMP is double-stapled.

In some embodiments, the StAMP is administered with a second agent that inhibits the growth of the Gram-negative colistin-resistant bacterium or the Gram-positive antibiotic-resistant bacterium. In some embodiments, the second agent is an antibiotic, or another antimicrobial peptide. In some embodiments, the antibiotic is selected from the group consisting of carbapenem, an aminoglycoside, vancomycin, methicillin, clarithromycin, cephalosporin, penicillin, ampicillin, fluoroquinolone, tetracycline, and a β-lactam. In certain embodiments, the second agent is a silver nanoparticle. In other embodiments, the second agent is a phage therapy. In some embodiments, the second agent is an antimicrobial vaccine. In some embodiments, the StAMP is administered with an agent that can act synergistically with the StAMP such as β-lactams, carbapenems, and other antimicrobial peptides like PGLa to inhibit the growth of the Gram-negative colistin-resistant bacterium or the Gram-positive antibiotic-resistant bacterium. In other embodiments, the StAMP is administered with an antibiotic that could get better access to bacteria such as vancomycin and oxazolidinones and thus be more effective, once the cell membrane is porated.

In one aspect, this disclosure provides methods of killing or inhibiting the growth of Gram-negative colistin-resistant bacteria that include contacting the Gram-negative colistin-resistant bacteria with a stapled and/or stitched antimicrobial peptide (StAMP) (e.g., a hydrocarbon-stapled and/or stitched antimicrobial peptide) described herein.

In one aspect, this disclosure provides methods of killing or inhibiting the growth of Gram-negative carbapenem-resistant bacteria that include contacting the Gram-negative carbapenem-resistant bacteria with a stapled and/or stitched antimicrobial peptide (StAMP) (e.g., a hydrocarbon-stapled and/or stitched antimicrobial peptide) described herein. In certain instances, the carbapenem is one or more of meropenem, imipenem, ertapenem, doripenem, panipenem, biapenem, and tebipenem.

In one aspect, this disclosure provides methods of killing or inhibiting the growth of Gram-positive antibiotic-resistant bacteria that include contacting the Gram-positive antibiotic-resistant bacteria with a stapled and/or stitched antimicrobial peptide (StAMP) (e.g., a hydrocarbon-stapled and/or stitched antimicrobial peptide) described herein. In some instances, the bacteria is resistant to a carbapenem (e.g., meropenem, imipenem, ertapenem, doripenem, panipenem, biapenem, and tebipenem).

In one aspect, this disclosure provides methods of killing or inhibiting the growth of Gram-positive carbapenem-resistant bacteria that include contacting the Gram-positive carbapenem-resistant bacteria with a stapled and/or stitched antimicrobial peptide (StAMP) (e.g., a hydrocarbon-stapled and/or stitched antimicrobial peptide) described herein. In certain instances, the carbapenem is one or more of meropenem, imipenem, ertapenem, doripenem, panipenem, biapenem, and tebipenem. In certain instances, the method further comprises contacting the Gram-positive carbapenem-resistant bacteria with one or both of daptomycin and vancomycin.

In certain embodiments, contacting is in vitro (e.g., under conventional conditions of cell culture, in a cell culture plate or dish, in an ex vivo cell culture system (i.e. propagation of cells that were previously in vivo)). In certain embodiments, contacting is in vivo (e.g., in a subject (e.g., a human subject, an animal model, a cell that is inside the subject)).

In certain embodiments, the Gram-negative colistin-resistant bacteria is selected from the group consisting of *A. baumannii, E. coli, Pseudomonas aeruginosa, Neisseria gonorrhoeae, Chlamydia trachomatis, Yersinia pestis, Proteus mirabilis, Enterobacter cloacae, Serratia marcescens Helicobacter pylori, Salmonella enteritidis, Salmonella typhi, Shigella, Moraxella, Stenotrophomonas, Bdellovibrio*, acetic acid bacteria, *Klebsiella pneumoniae*, and *Legionella pneumophila*, or a Gram-negative bacteria that contains a MCR-1 plasmid.

In certain embodiments, the Gram-positive antibiotic-resistant bacteria is selected from the group consisting of *Actinomyces israelii, Actinomyces gerencseriae, Propionibacterium propionicus, Bacillus anthracis, Arcanobacterium haemolyticum, Bacillus cereus*, bacterial vaginosis microbiota, *Clostridium botulinum, Mycobacterium ulcerans*, Group A *Streptococcus* and *Staphylococcus, Clostridium difficile, Corynebacterium diphtheria, Enterococcus species, Clostridium perfringens*, other *Clostridium* species, *Streptococcus pyogenes, Streptococcus agalactiae, Mycobacterium leprae, Mycobacterium lepromatosis, Listeria monocytogenes, Nocardia asteroides, Nocardia species, Streptococcus pneumoniae, Staphylococcus aureus, Staphylococcus species, Clostridium tetani, Mycobacterium tuberculosis, Yersinia pseudotuberculosis*, and *Yersinia enterocolitica*.

In certain embodiments, the stapled and/or stitched antimicrobial peptide (e.g., a hydrocarbon-stapled and/or stitched antimicrobial peptide) is based on or derived from a peptide selected from the group consisting of magainin, pleurocidin, pexiganan, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

In certain embodiments, the StAMP comprises or consists of the amino acid sequence set forth in any one of SEQ ID Nos.: 1-3, 34, 35 or 36-43 except for 1 to 5 amino acid substitutions, insertions, and/or deletions within SEQ ID Nos.: 1-3, 34, 35 or 36-43. In certain embodiments, the StAMP comprises or consists of a StAMP based on or derived from the scaffold of a peptide having the amino acid sequence set forth in any one of SEQ ID Nos.: 4-33 except for 1 to 5 amino acid substitutions, insertions, and/or deletions within SEQ ID Nos.: 4-33. In certain embodiments, the StAMP comprises or consists of the amino acid sequence set forth in any one SEQ ID NO: 1, 2, 3, 34, 35 or 36-43. In certain embodiments, the StAMP comprises or consists of a StAMP based on or derived from the scaffold of a peptide having the amino acid sequence set forth in any one SEQ ID NO: 4-33. In some embodiments, the StAMP comprises or consists of the sequence of any one of SEQ ID Nos.: 7, 9, 11, 13, 15, 17, 19, 21, 23, 25, 27, 29, 31, or 33.

In another aspect, the disclosure provides methods of optimizing a stabilized (e.g., stapled and/or stitched) antimicrobial peptide (StAMP) (e.g., a hydrocarbon-stapled and/or stitched antimicrobial peptide) that include: (a) providing a first StAMP; (b) generating a second StAMP that is identical to the first StAMP except at one or more amino acid positions; (c) determining that the second StAMP kills or inhibits growth of a Gram-negative colistin-resistant bacterium or a Gram-positive antibiotic-resistant bacterium to a greater level than the first StAMP.

In some embodiments, the methods further include determining that the second StAMP has the same or decreased hemolytic activity relative to the first StAMP.

In some embodiments, the first StAMP and the second StAMP are double-stapled and/or stitched. In some embodiments, the StAMP comprises or consists of the amino acid sequence set forth in any one of SEQ ID Nos.: 1-3, 34, or 35 except for 1 to 5 amino acid substitutions, insertions, and/or deletions within SEQ ID Nos.: 1-3, 34 or 35. In some embodiments, the StAMP comprises or consists of a StAMP based on or derived from the scaffold of a peptide having the amino acid sequence set forth in any one of SEQ ID Nos.: 4-33 except for 1 to 5 amino acid substitutions, insertions, and/or deletions within SEQ ID Nos.: 1-35. In some embodiments, the StAMP comprises or consists of the amino acid sequence set forth in any one SEQ ID NO: 1, 2, or 3. In some embodiments, the StAMP comprises or consists of a StAMP based on or derived from the scaffold of a peptide having the amino acid sequence set forth in any one SEQ ID NO: 4-33. In some embodiments, the StAMP comprises or consists of the sequence of any one of SEQ ID Nos.: 7, 9, 11, 13, 15, 17, 19, 21, 23, 25, 27, 29, 31, or 33.

In some embodiments, the first and second StAMP are each 6 to 100 amino acids in length (e.g., between 6 and 40 amino acids in length (e.g., between 6 and 10 amino acids in length, between 6 and 15 amino acids in length, between 6 and 20 amino acids in length, between 6 and 25 amino acids in length, between 6 and 30 amino acids in length, between 6 and 35 amino acids in length; between 10 and 15 amino acids in length, between 10 and 20 amino acids in length, between 10 and 25 amino acids in length, between 10 and 30 amino acids in length, between 10 and 35 amino acids in length; between 15 and 20 amino acids in length, between 15 and 25 amino acids in length, between 15 and 30 amino acids in length, between 15 and 35 amino acids in length; between 15 and 40 amino acids in length; between 20 and 25 amino acids in length, between 20 and 30 amino acids in length, between 20 and 35 amino acids in length; between 20 and 40 amino acids in length; between 30 and 35 amino acids in length; between 30 and 40 amino acids in length; or between 35 and 40 amino acids in length).

In some embodiments, the second StAMP is dihydroxylated as compared to the first StAMP, and the hydrophobicity of the second StAMP is reduced as compared to the first StAMP. In some embodiments, the second StAMP is aminohydroxylated as compared to the first StAMP, and the hydrophobicity of the second StAMP is reduced as compared to the first StAMP.

In some embodiments, the antimicrobial activity is against *A. baumannii*. In some embodiments, the antimicrobial activity is against *E. coli*. In some embodiments, the antimicrobial activity is against an *E. coli* strain that contains a MCR-1 plasmid. In some embodiments, the antimicrobial activity is against *S. aureus*.

In some embodiments, hemolytic activity of the second StAMP is reduced compared to the first StAMP and the hemolytic activity of the second StAMP is less than 50% (e.g., less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or 0-5%), and the minimum inhibitory concentration against a Gram-negative colistin-resistant bacterium is less than 10 µg/mL (e.g., less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, less than 0.5 µg/mL, or 0.5-3.0 µg/mL). In certain embodiments, hemolytic activity of the second StAMP is reduced compared to the first StAMP and the hemolytic activity of the second StAMP is less than 10%. In certain embodiments, hemolytic activity of the second StAMP is reduced compared to the first StAMP and the hemolytic activity of the second StAMP is greater than 20% but less than 50% (e.g., less than 45%, less than 40%, less than 35%, less than 30%, less than 25%).

In some embodiments, the Gram-negative bacterium is *A. baumannii* or *E. coli*.

In some embodiments, the Gram-negative bacterium is *A. baumannii*, *E. coli*, or a Gram-negative bacterium that contain a MCR-1 plasmid.

In another aspect, the disclosure provides methods of selecting a StAMP (e.g., hydrocarbon-StAMP) that overcomes colistin-resistance of a Gram-negative bacterium that include: (a) providing a StAMP; (b) determining the hemolytic activity and the minimum inhibitory concentration (MIC) of the StAMP for a Gram-negative bacterium; and (c) selecting the StAMP when the StAMP has: (i) a minimum inhibitory concentration against the Gram-negative bacterium of less than 10 µg/mL (e.g., less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, less than 0.5 µg/mL, or 0.5-3.0 µg/mL); and (ii) a hemolytic activity less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or 0-5%).

In some embodiments, the Gram-negative bacterium is *A. baumannii*, *E. coli*, or a Gram-negative bacterium that contains a MCR-1 plasmid. In some embodiments, the Gram-negative bacterium that contains a MCR-1 plasmid is *Klebsiella pneumoniae*.

In some embodiments, the methods further comprise: (a) generating a third StAMP that is identical to the second StAMP except at one or more amino acid positions, wherein the amino acid changes in the third StAMP (i) disrupt at least one hydrophobic patch that is present within the second StAMP, wherein the hydrophobic patch comprises at least 2 hydrophobic amino acid residues; and/or (ii) alter the charge nature of at least one cationic point charge that is present in the second StAMP. In some embodiments, the method further comprises determining that the third StAMP has a reduced renal toxicity relative to the second StAMP, e.g., by determining the renal toxicity of the second and third StAMPs using a primary proximal tubule epithelial cell (pRPTEC) renal toxicity assay or monitoring in vivo kidney function by, for example, serial serum creatinine measurements.

In some embodiments, the third StAMP comprises a disrupted hydrophobic patch relative to the second StAMP, wherein at least one hydrophobic amino acid (e.g., 1, 2, 3, 4, 5, 6, 7, 8, 9, or 10 or more hydrophobic amino acids) of at least one hydrophobic patch (e.g., 1, 2, 3, 4, or 5 hydrophobic patches) in the third StAMP is substituted with an amino acid having a reduced hydrophobicity.

In some embodiments, the method further comprises generating a fourth StAMP that is identical to the third StAMP except at one or more amino acid positions, wherein the amino acid changes in the fourth StAMP result in the substitution of at least one amino acid on the hydrophilic portion of the StAMP, e.g., the hydrophilic portion of an α-helix, that makes the hydrophilic portion of the StAMP more cationic. In some embodiments, at least one amino acid on a hydrophilic portion of the StAMP is substituted with at least one lysine, omithine, histidine, and/or arginine. In some embodiments, the fourth StAMP has an antimicrobial activity that is equivalent to or exceeds the antimicrobial activity of the third StAMP. In some embodiments, the fourth StAMP has a minimum inhibitory concentration (MIC) against an antibiotic resistant bacterium that is less than the minimum inhibitory concentration (MIC) against an antibiotic resistant bacterium of the third StAMP.

In another aspect, the disclosure provides methods of selecting a StAMP (e.g., hydrocarbon-StAMP) that overcomes antibiotic-resistance of a Gram-positive bacterium that include: (a) providing a StAMP; (b) determining the hemolytic activity and the minimum inhibitory concentration (MIC) of the StAMP for a Gram-positive bacterium; and (c) selecting the StAMP when the StAMP has: (i) a minimum inhibitory concentration against the Gram-positive bacterium of less than 10 µg/mL (e.g., less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, less than 0.5 µg/mL, or 0.5-3.0 µg/mL); and (ii) a hemolytic activity less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or 0-5%). In some embodiments, the Gram-positive bacterium is *S. aureus*.

In some embodiments, providing includes providing a StAMP from a StAMP library. In some embodiments, the StAMP is from a StAMP library. In some embodiments, the StAMP library is a library of a StAMP based on or derived from the scaffold of a peptide selected from the group consisting of: magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin. In certain embodiments, the StAMP library is a staple walk library.

In some embodiments, the stapled and/or stitched (e.g., hydrocarbon-stapled and/or stitched) antimicrobial peptide is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

In some embodiments, the methods further comprise reducing the renal toxicity of the selected StAMP by introducing at least one amino acid substitution (e.g., 1, 2, 3, 4, 5, 6, 7, 8, 9, or 10 substitutions) in the selected StAMP that: (i) disrupts at least one hydrophobic patch (e.g., 1, 2, 3, 4, or 5 hydrophobic patches) that is present within the selected StAMP, wherein the hydrophobic patch comprises at least 2 hydrophobic amino acid residues; and/or (ii) alters the charge nature of at least one cationic point charge that is present in the selected StAMP. In some embodiments, the methods further comprise determining that the StAMP with amino acid substitutions has a reduced renal toxicity relative to the StAMP that had been selected, e.g., by determining the renal toxicity of the StAMPs using a primary proximal tubule epithelial cell (pRPTEC) renal toxicity assay or monitoring in vivo kidney function by, for example, serial serum creatinine measurements.

In some embodiments, the methods further comprises introducing at least one amino acid substitution on the hydrophilic portion of the StAMP, e.g., the hydrophilic portion of an α-helix, that makes the hydrophilic portion of the StAMP more cationic. In some embodiments, at least one amino acid on a hydrophilic portion of the StAMP is substituted with at least one lysine, omithine, histidine, and/or arginine. In some embodiments, the StAMP has an antimicrobial activity that is equivalent to or exceeds the antimicrobial activity of the StAMP that had been selected.

In yet another aspect, this disclosure provides methods of screening for a StAMP that kills or inhibits the growth of a colistin-resistant Gram-negative bacterium that include: (a) providing a StAMP; (b) contacting the StAMP with a colistin-resistant Gram-negative bacterium; (c) determining that the StAMP kills or inhibits the growth of the colistin-resistant Gram-negative bacterium with a MIC of less than 5.0 µg/ml.

In certain embodiments, the methods further include determining that the StAMP has a hemolytic activity of less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or 0-5%). In certain embodiments, the StAMP has a MIC for the colistin-resistant Gram-negative bacterium of less than 10 µg/mL (e.g., less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, less than 0.5 µg/mL, or 0.5-3.0 µg/mL). In certain other embodiments, the methods further include determining that the StAMP has a hemolytic activity greater than 20% but less than 50% (e.g., less than 45%, less than 40%, less than 35%, less than 30%, less than 25%).

In another aspect, this disclosure provides methods of screening for a StAMP that kills or inhibits the growth of an antibiotic-resistant Gram-positive bacterium that include: (a) providing a StAMP; (b) contacting the StAMP with an antibiotic-resistant Gram-positive bacterium; (c) determining that the StAMP kills or inhibits the growth of the antibiotic-resistant Gram-positive bacterium with a MIC of less than 5.0 µg/ml.

In certain embodiments, the methods further include determining that the StAMP has a hemolytic activity of less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or 0-5%). In certain embodiments, the StAMP has a MIC for the antibiotic-resistant Gram-positive bacterium of less than 10 µg/mL (e.g., less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, less than 0.5 µg/mL, or 0.5-3.0 µg/mL). In certain other embodiments, the methods further include determining that the StAMP has a hemolytic activity greater than 20% but less than 50% (e.g., less than 45%, less than 40%, less than 35%, less than 30%, less than 25%).

In certain embodiments, the stapled and/or stitched antimicrobial peptide (e.g., hydrocarbon-stapled and/or stitched peptide) is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

In certain embodiments, the StAMP is from a StAMP library. In certain embodiments, the StAMP library is a library of a StAMP based on or derived from the scaffold of a peptide selected from the group consisting of: magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin. In certain embodiments, the StAMP library is a staple walk library.

In some embodiments, the methods further comprise reducing the renal toxicity of the selected StAMP by introducing at least one amino acid substitution (e.g., 1, 2, 3, 4, 5, 6, 7, 8, 9, or 10 substitutions) in the selected StAMP that: (i) disrupts at least one hydrophobic patch (e.g., 1, 2, 3, 4, or 5 hydrophobic patches) that is present within the selected StAMP, wherein the hydrophobic patch comprises at least 2 hydrophobic amino acid residues; and/or (ii) alters the charge nature of at least one cationic point charge that is present in the selected StAMP. In some embodiments, the methods further comprise determining that the StAMP with amino acid substitutions has a reduced renal toxicity relative to the StAMP screened for killing or inhibiting the growth of a colistin-resistant Gram-negative bacterium, e.g., by determining the renal toxicity of the StAMPs using a primary proximal tubule epithelial cell (pRPTEC) renal toxicity assay or monitoring in vivo kidney function by, for example, serial serum creatinine measurements.

In some embodiments, the methods further comprises introducing at least one amino acid substitution on the hydrophilic portion of the StAMP, e.g., the hydrophilic portion of an α-helix, that makes the hydrophilic portion of the StAMP more cationic. In some embodiments, at least one amino acid on a hydrophilic portion of the StAMP is substituted with at least one lysine, ornithine, histidine, and/or arginine. In some embodiments, the StAMP has an antimicrobial activity that is equivalent to or exceeds the antimicrobial activity of the StAMP screened for killing or inhibiting the growth of a colistin-resistant Gram-negative bacterium.

In certain embodiments, the StAMP is formulated with a pharmaceutical composition as a pharmaceutically acceptable carrier.

The disclosure also features the use of StAMPs as an antibacterial coating for materials, devices, or products (e.g., medical devices, catheters, bandages, adhesive tapes) or ingredient in antimicrobial solutions or products (e.g., soaps, ointments, cosmetics). Such antibacterial coatings or products can be useful in reducing or preventing the spread of Gram-negative or Gram-positive bacterial infections.

The disclosure also provides solutions, products, and reagents comprising the one or more of StAMPs disclosed herein. For example, such products are useful as cosmetics, soaps, or other liquids/reagents to avoid Gram-negative or Gram-positive bacterial infection and/or colonization.

The disclosure also features methods of determining a suitable treatment for a subject having, or suspected of having, an antibiotic-resistant Gram-negative bacterial infection that include: (a) obtaining a biological sample from the subject; (b) contacting the biological sample of the subject with a StAMP; (c) determining that the StAMP kills or inhibits the growth of the antibiotic-resistant Gram-negative bacteria in the sample; and (d) selecting and administering the StAMP to the subject. In some embodiments, the antibiotic-resistant Gram-negative bacteria is colistin-resistant.

The disclosure also features methods of determining a suitable treatment for a subject having, or suspected of having, an antibiotic-resistant Gram-positive bacterial infection that include: (a) obtaining a biological sample from the subject; (b) contacting the biological sample of the subject with a StAMP; (c) determining that the StAMP kills or inhibits the growth of the antibiotic-resistant Gram-positive bacteria in the sample; and (d) selecting and administering the StAMP to the subject.

Another feature of this disclosure relates to methods for predicting the efficacy of a StAMP in treating a colistin-resistant Gram-negative bacterial infection that include: (a) contacting Gram-negative bacteria responsible for the colistin-resistant Gram-negative bacterial infection with the StAMP; (b) determining that the StAMP kills or inhibits the growth of the Gram-negative bacteria; and (c) predicting that the StAMP is likely to treat the Gram-negative bacterial infection.

Yet another feature of this disclosure relates to methods for predicting the efficacy of a StAMP in treating an antibiotic-resistant Gram-positive bacterial infection that include: (a) contacting Gram-positive bacteria responsible for the antibiotic-resistant Gram-positive bacterial infection with the StAMP; (b) determining that the StAMP kills or inhibits the growth of the Gram-positive bacteria; and (c) predicting that the StAMP is likely to treat the Gram-positive bacterial infection.

In some embodiments, the StAMP is determined to have hemolytic activity of less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or 0-5%). In other embodiments, the StAMP is determined to have hemolytic activity of greater than 20% but less than 50% (e.g., less than 45%, less than 40%, less than 35%, less than 30%, less than 25%).

In some embodiments, the StAMP is based on or derived from the scaffold of a peptide selected from the group consisting of: magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

In some embodiments, the StAMP comprises or consists a StAMP based on or derived from the scaffold of a peptide having the amino acid sequence set forth in any one of SEQ ID Nos.: 1-43 except for 1 to 5 amino acid substitutions, insertions, and/or deletions within SEQ ID Nos.: 1-43. In some embodiments, the StAMP comprises or consists of the amino acid sequence set forth in any one of SEQ ID Nos.: 1-3, 34, or 35-43 except for 1 to 5 amino acid substitutions, insertions, and/or deletions within SEQ ID Nos.: 1-3, 34 or 35-43. In some embodiments, the StAMP comprises or consists of the sequence of any one of SEQ ID Nos.: 1-43. In some embodiments, the StAMP comprises or consists of the sequence set forth in any one of SEQ ID NO: 1, 2, 3, 34, or 35-43. In some embodiments, the StAMP comprises or consists of the sequence of any one of SEQ ID Nos.: 7, 9, 11, 13, 15, 17, 19, 21, 23, 25, 27, 29, 31, or 33.

In some embodiments, the subject is human.

In yet another aspect, the disclosure features methods of using the StAMPs disclosed herein for veterinary use. For example, this disclosure provides methods of treating livestock having, or at risk of developing a bacterial infection including an antibiotic-resistant bacterial infection (e.g., a Gram-negative infection (e.g., a Gram-negative colistin-resistant bacterial infection); or a Gram-positive infection). The method involves administering to the animal an effective amount of a StAMP disclosed herein to treat, control, or prevent the bacterial infection.

In certain embodiments, the animal to be treated includes, but is not limited to, a pig, a chicken, a cow, a buffalo, a goat, a horse, a dog, a cat, a bird (e.g., a goose, a parrot, a cockatoo, a parakeet).

In certain embodiments, the StAMP is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin. To be "based on or derived from the scaffold of a peptide" means that at least two (e.g., 2, 3, 4, 5, 6) amino acids of these peptides that are spaced at least 2, 3, or 6 amino acids apart are replaced with non-natural amino acids with olefinic side chains that can form a staple or a stitch (e.g., a hydrocarbon-staple or stitch). Examples of such peptides are provided in SEQ ID NOs.: 1-3. In certain embodiments, the StAMP (e.g., hydrocarbon-stapled and/or stitched antimicrobial peptide) is derived from the magainin scaffold. In certain embodiments, the StAMP (e.g., hydrocarbon-stapled and/or stitched antimicrobial peptide) is derived from the pleurocidin scaffold.

In certain embodiments, the StAMP comprises or consists of the amino acid sequence set forth in any one of SEQ ID Nos.: 1-3, 34 or 35-43 except for 1 to 5 (i.e., 1, 2, 3, 4, or 5) amino acid substitutions, insertions, and/or deletions within SEQ ID Nos.: 1-3, 34 or 35-43. In certain embodiments one or more of these amino substitutions are conservative amino acid substitutions. In certain embodiments, the StAMP comprises or consists of a StAMP based on or derived from the scaffold of a peptide having the amino acid sequence set forth in any one of SEQ ID Nos.: 4-33 except for 1 to 5 (i.e., 1, 2, 3, 4, or 5) amino acid substitutions, insertions, and/or deletions within SEQ ID Nos.: 4-33. In some embodiments, the StAMP comprises or consists of the sequence of any one of SEQ ID Nos.: 7, 9, 11, 13, 15, 17, 19, 21, 23, 25, 27, 29, 31, or 33, except for 1 to 5 (i.e., 1, 2, 3, 4, or 5) amino acid substitutions, insertions, and/or deletions within SEQ ID Nos.: 7, 9, 11, 13, 15, 17, 19, 21, 23, 25, 27, 29, 31, or 33. In certain embodiments one or more of these amino substitutions are conservative amino acid substitutions.

In certain embodiments, the StAMP comprises or consists of an amino acid sequence that is at least 45%, 50%, 55%, 60%, 65%, 70%, 75%, 80%, 85%, 90%, 91%, 92%, 93%, 94%, 95%, 96%, 97%, 98%, or 99% identical to the amino acid sequence set forth in any one SEQ ID NO: 1, 2, 3 or 36-43. In certain embodiments, the conservative amino acid substitution(s) made to any of these sequences (i.e., SEQ ID NOs.: 1-3) are not considered as being different/non-identical when determining the above-referenced % identity between the sequences. In some embodiments, the StAMP comprises or consists of an amino acid sequence that is at least 45%, 50%, 55%, 60%, 65%, 70%, 75%, 70%, 75%, 80%, 85%, 90%, 91%, 92%, 93%, 94%, 95%, 96%, 97%, 98%, or 99% identical to the amino acid sequence of any one of SEQ ID Nos.: 7, 9, 11, 13, 15, 17, 19, 21, 23, 25, 27, 29, 31, or 33. In certain embodiments, the conservative amino acid substitution(s) made to any of these sequences (i.e., SEQ ID Nos.: 7, 9, 11, 13, 15, 17, 19, 21, 23, 25, 27, 29, 31, or 33) are not considered as being different/non-identical when determining the above-referenced % identity between the sequences. In certain embodiments, the StAMP comprises or consists of a StAMP based on or derived from the scaffold of a peptide having an amino acid sequence that is at least 45%, 50%, 55%, 60%, 65%, 70%, 75%, 70%, 75%, 80%, 85%, 90%, 91%, 92%, 93%, 94%, 95%, 96%, 97%, 98%, or 99% identical to the amino acid sequence set forth in any one SEQ ID NO: 4-33. In certain embodiments, the conservative amino acid substitution(s) made to any of these sequences (i.e., SEQ ID Nos.: 4-33) are not considered as being different/non-identical when determining the above-referenced % identity between the sequences.

In certain embodiments, the StAMP comprises or consists of the amino acid sequence set forth in any one SEQ ID NO: 1, 2, 3, 34, or 35-43. In some embodiments, the StAMP comprises or consists of the sequence of any one of SEQ ID Nos.: 7, 9, 11, 13, 15, 17, 19, 21, 23, 25, 27, 29, 31, or 33. In certain instances, these sequences may be modified to include additional, e.g., 2 or more (e.g., 3, 4, 5, 6) non-natural olefinic side chain-containing amino acids that can form a hydrocarbon staple or stitch. In some embodiments, the StAMP comprises or consists of the sequence of any one of SEQ ID Nos.: 4-6, 8, 10, 12, 14, 16, 18, 20, 22, 24, 26, 28, 30, or 32 which are modified to have one to six (e.g., 1, 2, 3, 4, 5, or 6) "X's". The position of the "X" (i.e., the non-natural amino acid with olefinic side chains) in these sequences can be varied as long as the X's that are involved in forming a staple/stitch are separated by 2, 3, or 6 amino acids. In one embodiment, the X's that are involved in forming a staple/stitch are separated by 3 amino acids. In another embodiment, the X's that are involved in forming a staple/stitch are separated by 6 amino acids. In yet another embodiment, two of X's that are involved in forming a staple are separated by 3 amino acids; and a second two X's that are involved in forming a staple are separated by 3 amino acids. In certain embodiments, the "X's" in these sequences that are involved in forming a staple/stitch can be the same non-natural amino acid. In other embodiments, the "X's" in these sequences that are involved in forming a staple/stitch are different non-natural amino acids. In certain instances, "X" is one of (S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, or (S)-2-(2-propenyl)Ala-OH. In certain embodiments, if a sequence has two "X's" both X's are (S)-2-(4-pentenyl)Ala-OH. In certain embodiments, if a sequence has two "X's" both X's are (R)-2-(4-pentenyl)Ala-OH. In certain embodiments, if a sequence has two "X's" both X's are (R)-2-(7-octenyl)Ala-OH. In certain embodiments, if a sequence has two "X's" both X's are (S)-2-(7-octenyl)Ala-OH. In certain embodiments, if a sequence has two "X's" both X's are 2-amino-2-(pent-4-enyl)hept-6-enoic acid. In certain embodiments, if a sequence has two "X's" both X's are (R)-2-(2-propenyl)Ala-OH. In certain embodiments, if a sequence has two "X's" both X's are (R)-2-(2-propenyl)Ala-OH. In certain embodiments, if a sequence has two "X's" both X's are (S)-2-(2-propenyl)Ala-OH. In certain embodiments, if a sequence has two "X's" both X's are different non-natural amino acids and can, e.g., be selected from the group consisting of S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, and (S)-2-(2-propenyl)Ala-OH. In certain instances, if the two X's are separated by 3 amino acids, the two X's can be different non-natural residues, e.g., the first X is (R)-2-(2-propenyl)Ala-OH or (S)-2-(2-propenyl)Ala-OH and the second X is (S)-2-(2-propenyl)Ala-OH or (R)-2-(2-propenyl)Ala-OH. In certain instances, the "X's" that are in SEQ ID Nos.: 1-3, 34, 35, 7, 9, 11, 13, 15, 17, 19, 21, 23, 25, 27, 29, 31, 33 or 36-43, or inserted into SEQ ID Nos.: 4-6, 8, 10, 12, 14, 16, 18, 20, 22, 24, 26, 28, 30, or 32 can be any residue/substance that permits formation of a staple and/or stitch. In other words, the staple and/or stitch does not need to be a hydrocarbon-staple and/or stitch. Methods of performing different types of stapling are well known in the art (see, e.g., *Lactam stapling*: Shepherd et al., *J. Am. Chem. Soc.*, 127:2974-2983 (2005); *Triazole stapling*: Kawamoto et al., *J. Med. Chem.*, 55:1137-1146 (2011); *UV-cycloaddition stapling*: Madden et al., *Bioorg. Med. Chem. Lett.*, 21:1472-1475 (2011); *Disulfide stapling*: Jackson et al., *Am. Chem. Soc.*, 113:9391-9392 (1991); *Oxime stapling*: Haney et al., *Chem. Commun.*, 47:10915-10917 (2011); *Thioether stapling*: Brunel and Dawson, *Chem. Commun.*, 552-2554 (2005); *Photoswitchable stapling*: J. R. Kumita et al., *Proc. Natl. Acad. Sci. U.S.A*, 97:3803-3808 (2000); *Double-click stapling*: Lau et al., *Chem. Sci.*, 5:1804-1809 (2014); *Bis-lactam stapling*: J. C. Phelan et al., *J. Am. Chem. Soc.*, 119:455-460 (1997); and *Bis-arylation stapling*: A. M. Spokoyny et al., *J. Am. Chem. Soc.*, 135:5946-5949 (2013)). In certain instances, the "X's" that are in SEQ ID Nos.: 1-3, 34, 35, 7, 9, 11, 13, 15, 17, 19, 21, 23, 25, 27, 29, 31, 33 or 36-43, or inserted into SEQ ID Nos.: 4-6, 8, 10, 12, 14, 16, 18, 20, 22, 24, 26, 28, 30, or 32 can be any residue that permits formation of a hydrocarbon staple and/or stitch. In certain instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are lactam stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are triazole stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are stapled using a UV-cycloaddition staple. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are disulfide stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are oxime stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are thioether stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 comprise a photoswitchable staple. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are double-click stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 are bis-lactam stapled. In other instances, the peptides with the sequences recited in SEQ ID Nos.: 1-3, 34, 35, 7, 9, 11, 13, 15, 17, 19, 21, 23, 25, 27, 29, 31, 33 or 36-43, or modified peptides with the sequences recited in SEQ ID Nos.: 4-6, 8, 10, 12, 14, 16, 18, 20, 22, 24, 26, 28, 30, or 32 comprise a bis-arylation staple. In certain embodiments, the StAMP comprises or consists of the amino acid sequence set forth in, or a modified version (i.e., a sequence comprising 2 or more (e.g., 3, 4, 5, 6) non-natural olefinic side chain-containing amino acids that can form a hydrocarbon staple) of, an amino sequence set forth in any one SEQ ID NO: 4-33.

In some embodiments of any of the methods described herein, the StAMP is 6 to 100 amino acids in length (e.g., between 6 and 40 amino acids in length (e.g., between 6 and 10 amino acids in length, between 6 and 15 amino acids in length, between 6 and 20 amino acids in length, between 6 and 25 amino acids in length, between 6 and 30 amino acids in length, between 6 and 35 amino acids in length; between 10 and 15 amino acids in length, between 10 and 20 amino acids in length, between 10 and 25 amino acids in length, between 10 and 30 amino acids in length, between 10 and 35 amino acids in length; between 15 and 20 amino acids in length, between 15 and 25 amino acids in length, between 15 and 30 amino acids in length, between 15 and 35 amino acids in length; between 15 and 40 amino acids in length; between 20 and 25 amino acids in length, between 20 and 30 amino acids in length, between 20 and 35 amino acids in length; between 20 and 40 amino acids in length; between 30 and 35 amino acids in length; between 30 and 40 amino acids in length; or between 35 and 40 amino acids in length).

In a particular embodiment, the animal is a chicken. In another particular embodiments, the animal is a pig. In another particular embodiments, the animal is a cow.

In certain embodiments, the animal's infection has developed antibiotic-resistance to at least one (e.g., 1, 2, 3, 4, 5, 6, 7, 8, 9, or 10) other class of antibiotic. In some embodiments, the at least one (e.g., 1, 2, 3, 4, 5, 6, 7, 8, 9, or 10) other class of antibiotic is selected from the group consisting of: carbapenem, an aminoglycoside, vancomycin, methicillin, clarithromycin, cephalosporin, penicillin, ampicillin, fluoroquinolone, tetracycline, and a β-lactam. In certain embodiments, the at least one other class of antibiotic is carbapenem. In certain embodiments, the at least one other class of antibiotic is clarithromycin. In certain embodiments, the at least one other class of antibiotic is cephalosporin. In certain embodiments, the at least one other class of antibiotic is fluoroquinolone. In certain embodiments, the at least one other class of antibiotic is methicillin. In certain embodiments, the at least one other class of antibiotic is vancomycin. In certain embodiments, the at least one other class of antibiotic is methicillin and vancomycin. In certain embodiments, the at least one other class of antibiotic is cephalosporin and fluoroquinolone.

In some embodiments, the animal has a chronic Gram-negative colistin-resistant bacterial infection. In some embodiments, the Gram-negative colistin-resistant bacterial infection is an *A. baumannii* infection. In some embodiments, the Gram-negative colistin-resistant bacterial infection is an *E. coli* infection. In some embodiments, the Gram-negative colistin-resistant bacterial infection is a *Klebsiella pneumoniae* infection. In some embodiments, the Gram-negative colistin-resistant bacterial infection is an infection selected from the group consisting of a *Pseudomonas* infection, a *Neisseria* infection, a *Chlamydia* infection, a *Yersinia* infection, a *Proteus* infection, an *Enterobacter* infection, a *Serratia* infection, a *Helicobacter* infection, a *Salmonella* infection, a *Salmonella* infection, a *Shigella*, a *Moraxella* infection, a *Stenotrophomonas*, a *Klebsiella* infection, and a *Legionella* infection. In some embodiments, the Gram-negative colistin-resistant bacterial infection is an infection selected from the group consisting of a *Pseudomonas aeruginosa* infection, a *Neisseria gonorrhoeae* infection, a *Chlamydia trachomatis* infection, a *Yersinia pestis* infection, a *Proteus mirabilis* infection, an *Enterobacter cloacae* infection, a *Serratia marcescens* infection, a *Helicobacter pylori* infection, a *Salmonella enteritidis* infection, a *Salmonella typhi* infection, a *Shigella* infection, a *Moraxella* infection, a *Stenotrophomonas* infection, a *Bdellovibrio* infection, an acetic acid bacterial infection, a *Klebsiella pneumoniae* infection, and a *Legionella pneumophila* infection. In some embodiments, the Gram-negative colistin-resistant bacterial infection is from a Gram-negative bacterium that contains a MCR-1 plasmid. In some embodiments, the Gram-negative bacterium that contains a MCR-1 plasmid is *E. coli*.

In some embodiments, the StAMP is administered intravenously. In other embodiments, the StAMP is administered via an intravenous route.

In a further aspect, this disclosure relates to methods of using the StAMPs disclosed herein as antibiotics on plants. These methods are useful in control of bacterial diseases of plants. In some instances, these methods are useful to treat antibiotic-resistant plant bacterial infections (e.g., streptomycin- or oxytetracycline-resistant bacterial infections). The methods involves contacting or administering to a plant having, or at risk of developing, a bacterial infection an effective amount of a StAMP disclosed herein. These methods are useful in agriculture, forestry management, as well as gardening.

In certain embodiments, the bacterial infection is a Gram-negative antibiotic-resistant bacterial infection. In certain embodiments, the bacterial infection is a Gram-negative colistin-resistant bacterial infection. In certain embodiments, the bacterial infection is a streptomycin-resistant bacterial infection. In other embodiments, the bacterial infection is an oxytetracycline-resistant bacterial infection. In certain embodiments, the bacterial infection is a streptomycin-resistant and oxytetracycline-resistant bacterial infection. In certain embodiments, the bacterial infection is a Gram-positive antibiotic-resistant bacterial infection.

In certain embodiments, the methods described above can be used to control, treat, or prevent bacterial soft rot of fruits and/or vegetables. In certain embodiments, the methods described above can be used to control, treat, or prevent Citrus canker (e.g., that caused by *Xanthomonas campestris*). In some embodiments, the claimed method can be used to control, treat, or prevent fire blight. Fire blight is broken down into several sub-categories including blossom blight, shoot blight, rootstock blight, and trauma blight. The claimed method can be used for each of these. In one particular embodiment, the StAMPs are used to treat, control, or prevent blossom blight. In some cases, the fire blight is of pear. In other cases, the fire blight is of apple. In other cases, the fire blight is of quince. In other cases, the fire blight is of an ornamental tree/plant. In some embodiments, the claimed method can be used to control, treat, or prevent bacterial infections in peach and/or nectarines. In some embodiments, the claimed method can be used to control, treat, or prevent bacterial infections in floriculture. In some embodiments, the claimed method can be used to control, treat, or prevent bacterial infections in seeds. In some embodiments, the claimed method can be used to control, treat, or prevent bacterial infections in seedlings (e.g., of celery, pepper, potato, tomato, tobacco) in the field and/or the greenhouse.

In some embodiments, the StAMP is mixed in a large volume of water to a concentration of 50-200 ppm and blown into tree canopies with a high-pressure (air-blast) sprayer. In some embodiments, the StAMP is applied to the surface of plants. In some embodiments, the StAMP is injected into the trunk of a tree. In some embodiments, the StAMP is sprayed over the plants. In some embodiments, the StAMP treatment is performed weekly. In some embodiments, the StAMP treatment is performed biweekly. In some embodiments, the StAMP treatment is performed monthly. In a particular embodiment, the StAMP is applied or provided to the plant/tree during the growth phase of the pathogen on the surface of the plant, flower, or tree.

In certain embodiments, the StAMP is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin. To be "based on or derived from the scaffold of a peptide" means that at least two (e.g., 2, 3, 4, 5, 6) amino acids of these peptides that are spaced at least 2, 3, or 6 amino acids apart are replaced with non-natural amino acids with olefinic side chains that can form a staple or a stitch (e.g., a hydrocarbon-staple or stitch). Examples of such peptides are provided in SEQ ID NOs.: 1-3. In certain embodiments, the StAMP (e.g., hydrocarbon-stapled and/or stitched antimicrobial peptide) is derived from the magainin scaffold. In certain embodiments, the StAMP (e.g., hydrocarbon-stapled and/or stitched antimicrobial peptide) is derived from the pleurocidin scaffold.

In certain embodiments, the StAMP comprises or consists of the amino acid sequence set forth in any one of SEQ ID Nos.: 1-3, 34, or 35 except for 1 to 5 (i.e., 1, 2, 3, 4, or 5) amino acid substitutions, insertions, and/or deletions within SEQ ID Nos.: 1-3, 34 or 35. In certain embodiments one or more of these amino substitutions are conservative amino acid substitutions. In certain embodiments, the StAMP comprises or consists of a StAMP based on or derived from the scaffold of a peptide having the amino acid sequence set forth in any one of SEQ ID Nos.: 4-33 except for 1 to 5 (i.e., 1, 2, 3, 4, or 5) amino acid substitutions, insertions, and/or deletions within SEQ ID Nos.: 4-33. In some embodiments, the StAMP comprises or consists of the sequence of any one of SEQ ID Nos.: 7, 9, 11, 13, 15, 17, 19, 21, 23, 25, 27, 29, 31, or 33, except for 1 to 5 (i.e., 1, 2, 3, 4, or 5) amino acid substitutions, insertions, and/or deletions within SEQ ID Nos.: 7, 9, 11, 13, 15, 17, 19, 21, 23, 25, 27, 29, 31, or 33. In certain embodiments one or more of these amino substitutions are conservative amino acid substitutions.

In certain embodiments, the StAMP comprises or consists of an amino acid sequence that is at least 45%, 50%, 55%, 60%, 65%, 70%, 75%, 80%, 85%, 90%, 91%, 92%, 93%, 94%, 95%, 96%, 97%, 98%, or 99% identical to the amino acid sequence set forth in any one SEQ ID NO: 1, 2, 3, 34, or 35. In certain embodiments, the conservative amino acid substitution(s) made to any of these sequences (i.e., SEQ ID NOs.: 1-3, 34, or 35) are not considered as being different/non-identical when determining the above-referenced % identity between the sequences. In some embodiments, the StAMP comprises or consists of an amino acid sequence that is at least 45%, 50%, 55%, 60%, 65%, 70%, 75%, 70%, 75%, 80%, 85%, 90%, 91%, 92%, 93%, 94%, 95%, 96%, 97%, 98%, or 99% identical to the amino acid sequence of any one of SEQ ID Nos.: 7, 9, 11, 13, 15, 17, 19, 21, 23, 25, 27, 29, 31, or 33. In certain embodiments, the conservative amino acid substitution(s) made to any of these sequences (i.e., SEQ ID Nos.: 7, 9, 11, 13, 15, 17, 19, 21, 23, 25, 27, 29, 31, or 33) are not considered as being different/non-identical when determining the above-referenced % identity between the sequences. In certain embodiments, the StAMP comprises or consists of a StAMP based on or derived from the scaffold of a peptide having an amino acid sequence that is at least 45%, 50%, 55%, 60%, 65%, 70%, 75%, 70%, 75%, 80%, 85%, 90%, 91%, 92%, 93%, 94%, 95%, 96%, 97%, 98%, or 99% identical to the amino acid sequence set forth in any one SEQ ID NO: 4-33. In certain embodiments, the conservative amino acid substitution(s) made to any of these sequences (i.e., SEQ ID Nos.: 4-33) are not considered as being different/non-identical when determining the above-referenced % identity between the sequences.

In certain embodiments, the StAMP comprises or consists of the amino acid sequence set forth in any one SEQ ID NO: 1, 2, 3, 34, or 35. In some embodiments, the StAMP comprises or consists of the sequence of any one of SEQ ID Nos.: 7, 9, 11, 13, 15, 17, 19, 21, 23, 25, 27, 29, 31, or 33. In certain instances, these sequences may be modified to include additional, e.g., 2 or more (e.g., 3, 4, 5, 6) non-natural olefinic side chain-containing amino acids that can form a hydrocarbon staple or stitch. In some embodiments, the StAMP comprises or consists of the sequence of any one of SEQ ID Nos.: 4-6, 8, 10, 12, 14, 16, 18, 20, 22, 24, 26, 28, 30, or 32 which are modified to have one to six (e.g., 1, 2, 3, 4, 5, or 6) "X's". The position of the "X" (i.e., the non-natural amino acid with olefinic side chains) in these sequences can be varied as long as the X's that are involved in forming a staple/stitch are separated by 2, 3, or 6 amino acids. In one embodiment, the X's that are involved in forming a staple/stitch are separated by 3 amino acids. In another embodiment, the X's that are involved in forming a staple/stitch are separated by 6 amino acids. In yet another embodiment, two of X's that are involved in forming a staple are separated by 3 amino acids; and a second two X's that are involved in forming a staple are separated by 3 amino acids. In certain embodiments, the "X's" in these sequences that are involved in forming a staple/stitch can be the same non-natural amino acid. In other embodiments, the "X's" in these sequences that are involved in forming a staple/stitch are different non-natural amino acids. In certain instances, "X" is one of (S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, or (S)-2-(2-propenyl)Ala-OH. In certain embodiments, if a sequence has two "X's" both X's are (S)-2-(4-pentenyl)Ala-OH. In certain embodiments, if a sequence has two "X's" both X's are (R)-2-(4-pentenyl)Ala-OH. In certain embodiments, if a sequence has two "X's" both X's are (R)-2-(7-octenyl)Ala-OH. In certain embodiments, if a sequence has two "X's" both X's are (S)-2-(7-octenyl)Ala-OH. In certain embodiments, if a sequence has two "X's" both X's are 2-amino-2-(pent-4-enyl)hept-6-enoic acid. In certain embodiments, if a sequence has two "X's" both X's are (R)-2-(2-propenyl)Ala-OH. In certain embodiments, if a sequence has two "X's" both X's are (R)-2-(2-propenyl)Ala-OH. In certain embodiments, if a sequence has two "X's" both X's are (S)-2-(2-propenyl)Ala-OH. In certain embodiments, if a sequence has two "X's" both X's are different non-natural amino acids and can, e.g., be selected from the group consisting of S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, and (S)-2-(2-propenyl)Ala-OH. In certain instances, if the two X's are separated by 3 amino acids, the two X's can be different non-natural residues, e.g., the first X is (R)-2-(2-propenyl)Ala-OH or (S)-2-(2-propenyl)Ala-OH and the second X is (S)-2-(2-propenyl)Ala-OH or (R)-2-(2-propenyl)Ala-OH. In certain instances, the "X's" that are in SEQ ID Nos.: 1-3, 34, 35, 7, 9, 11, 13, 15, 17, 19, 21, 23, 25, 27, 29, 31, or 33, or inserted into SEQ ID Nos.: 4-6, 8, 10, 12, 14, 16, 18, 20, 22, 24, 26, 28, 30, or 32 can be any residue/substance that permits formation of a staple and/or stitch. In other words, the staple and/or stitch does not need to be a hydrocarbon-staple and/or stitch. Methods of performing different types of stapling are well known in the art (see, e.g., *Lactam stapling*: Shepherd et al., *J. Am. Chem. Soc.*, 127:2974-2983 (2005); *Triazole stapling*: Kawamoto et al., *J. Med. Chem.*, 55:1137-1146 (2011); *UV-cycloaddition stapling*: Madden et al., *Bioorg. Med. Chem. Lett.*, 21:1472-1475 (2011); *Disulfide stapling*: Jackson et al., *Am. Chem. Soc.*, 113:9391-9392 (1991); *Oxime stapling*: Haney et al., *Chem. Commun.*, 47:10915-10917 (2011); *Thioether stapling*: Brunel and Dawson, *Chem. Commun.*, 552-2554 (2005); *Photoswitchable stapling*: J. R. Kumita et al., *Proc. Natl. Acad. Sci. U.S.A*, 97:3803-3808 (2000); *Double-click stapling*: Lau et al., *Chem. Sci.*, 5:1804-1809 (2014); *Bis-lactam stapling*: J. C. Phelan et al., *J. Am. Chem. Soc.*, 119:455-460 (1997); and *Bis-arylation stapling*: A. M. Spokoyny et al., *J. Am. Chem. Soc.*, 135:5946-5949 (2013)). In certain instances, the "X's" that are in SEQ ID Nos.: 1-3, 34, 35, 7, 9, 11, 13, 15, 17, 19, 21, 23, 25, 27, 29, 31, or 33, or inserted into SEQ ID Nos.: 4-6, 8, 10, 12, 14, 16, 18, 20, 22, 24, 26, 28, 30, or 32 can be any residue that permits formation of a hydrocarbon staple and/or stitch. In certain instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 are lactam stapled. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 are triazole stapled. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 are stapled using a UV-cycloaddition staple. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 are disulfide stapled. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID NOs.: 4-6, 8, 10, 12, 14, 16, 18, 20, 22, 24, 26, 28, 30, or 32 are oxime stapled. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 are thioether stapled. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 comprise a photoswitchable staple. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 are double-click stapled. In other instances, the peptides with the sequences recited in SEQ ID NOs.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 are bis-lactam stapled. In other instances, the peptides with the sequences recited in SEQ ID Nos.: 1-3, 34, 35, 7, 9, 11, 13, 15, 17, 19, 21, 23, 25, 27, 29, 31, or 33, or modified peptides with the sequences recited in SEQ ID Nos.: 4-6, 8, 10, 12, 14, 16, 18, 20, 22, 24, 26, 28, 30, or 32 comprise a bis-arylation staple. In certain embodiments, the StAMP comprises or consists of the amino acid sequence set forth in, or a modified version (i.e., a sequence comprising 2 or more (e.g., 3, 4, 5, 6) non-natural olefinic side chain-containing amino acids that can form a hydrocarbon staple) of, an amino sequence set forth in any one SEQ ID NO: 4-33.

In some embodiments of any of the methods described herein, the StAMP is 6 to 100 amino acids in length (e.g., between 6 and 40 amino acids in length (e.g., between 6 and 10 amino acids in length, between 6 and 15 amino acids in length, between 6 and 20 amino acids in length, between 6 and 25 amino acids in length, between 6 and 30 amino acids in length, between 6 and 35 amino acids in length; between 10 and 15 amino acids in length, between 10 and 20 amino acids in length, between 10 and 25 amino acids in length, between 10 and 30 amino acids in length, between 10 and 35 amino acids in length; between 15 and 20 amino acids in length, between 15 and 25 amino acids in length, between 15 and 30 amino acids in length, between 15 and 35 amino acids in length; between 15 and 40 amino acids in length; between 20 and 25 amino acids in length, between 20 and 30 amino acids in length, between 20 and 35 amino acids in length; between 20 and 40 amino acids in length; between 30 and 35 amino acids in length; between 30 and 40 amino acids in length; or between 35 and 40 amino acids in length).

In certain embodiments, the plant infection has developed antibiotic-resistance to at least one (e.g., 1, 2, 3, 4, 5, 6, 7, 8, 9, or 10) other class of antibiotic. In some embodiments, the at least one (e.g., 1, 2, 3, 4, 5, 6, 7, 8, 9, or 10) other class of antibiotic is selected from the group consisting of: carbapenem, an aminoglycoside, vancomycin, methicillin, clarithromycin, cephalosporin, penicillin, ampicillin, fluoroquinolone, tetracycline, and a β-lactam. In certain embodiments, the at least one other class of antibiotic is carbapenem. In certain embodiments, the at least one other class of antibiotic is clarithromycin. In certain embodiments, the at least one other class of antibiotic is cephalosporin. In certain embodiments, the at least one other class of antibiotic is fluoroquinolone. In certain embodiments, the at least one other class of antibiotic is methicillin. In certain embodiments, the at least one other class of antibiotic is vancomycin. In certain embodiments, the at least one other class of antibiotic is methicillin and vancomycin. In certain embodiments, the at least one other class of antibiotic is cephalosporin and fluoroquinolone. In a particular embodiment, the plant has developed an infection with antibiotic-resistance to streptomycin. In certain embodiments, the plant has developed an infection with antibiotic-resistance to oxytetracycline.

In some embodiments, the plant has a chronic Gram-negative colistin-resistant bacterial infection. In some embodiments, the plant has a chronic Gram-positive antibiotic-resistant bacterial infection.

In another aspect, the disclosure relates to a method of reducing the renal toxicity of a stapled and/or stitched anti-microbial peptide (StAMP), the method comprising: (i) identifying at least one hydrophobic patch comprising two or more hydrophobic amino acids; (ii) introducing at least one amino acid substitution in the hydrophobic patch, wherein at least one of the hydrophobic amino acids in the hydrophobic patch is replaced with at least one amino acid with a reduced hydrophobicity, to produce a StAMP with at least one disrupted hydrophobic patch; and (iii) testing the StAMP with the at least one disrupted hydrophobic patch for reduced renal toxicity relative to a StAMP that is identical except that no amino acid substitutions have been introduced into its hydrophobic patches.

In some embodiments, the StAMP is 6 to 100 amino acids in length.

In some embodiments, at least one amino acid substitution is introduced into the StAMP to disrupt at least one hydrophobic patch. In some embodiments, one amino acid substitution is introduced into the StAMP to disrupt one hydrophobic patch. In some embodiments, at least two amino acid substitutions are introduced into the StAMP to disrupt one hydrophobic patch. In some embodiments, at least two amino acid substitutions are introduced into the StAMP to disrupt at least two hydrophobic patches.

In some embodiments, the StAMP comprises an α-helix with a hydrophobic face and a hydrophilic face. In some embodiments, at least one amino acid substitution is introduced on the hydrophilic portion of the StAMP. In some embodiments, an amino acid other than lysine on the hydrophilic portion of the StAMP is replaced with a lysine. In some embodiments, the StAMP exhibits greater anti-microbial activity relative to a StAMP that is identical except that it does not comprise a lysine substitution on the hydrophilic portion of its α-helix.

In another aspect, the disclosure relates to a method of reducing the renal toxicity of a stapled and/or stitched anti-microbial peptide (StAMP), the method comprising: (i) identifying at least one amino acid residue on the StAMP comprising a cationic point charge; (ii) introducing at least one amino acid substitution, wherein at least one cationic point charge is replaced with at least one amino acid with a different charge nature than the cationic point charge, thereby producing a StAMP with an altered cationic charge; and (iii) testing the StAMP with an altered cationic charge for reduced renal toxicity relative to a StAMP that is identical except that its cationic point charges have not been altered, thereby reducing the renal toxicity of the StAMP.

In some embodiments, at least one amino acid substitution is introduced into the StAMP to alter the charge nature of at least one cationic point charge. In some embodiments, one amino acid substitution is introduced into the StAMP to alter the charge nature of one cationic point charge. In some embodiments, at least two amino acid substitutions are introduced into the StAMP to alter the charge nature of at least two cationic point charges. In some embodiments, at least one lysine is substituted with either an arginine, histidine, or ornithine.

In some embodiments, the StAMP with reduced renal toxicity comprises or consists of any one of SEQ ID Nos.: 41-43. In some embodiments, the StAMP with reduced renal toxicity comprises an amino acid sequence that is at least 45%, 50%, 55%, 60%, 65%, 70%, 75%, 80%, 85%, 86%, 87%, 88%, 89%, 90%, 92%, 95%, 96%, 97%, 98%, 99%, 90% identical to an amino acid sequence selected from the group consisting of SEQ ID Nos.: 41-43. In some embodiments, the StAMP exhibits reduced renal toxicity relative to a StAMP that is identical except that it does not comprise an amino acid substitution that disrupts a hydrophobic patch and/or alters a cationic point charge. In some embodiments, the StAMP with reduced renal toxicity comprises or consists of any one of SEQ ID Nos.: 36-40. In some embodiments, the StAMP with reduced renal toxicity comprises an amino acid sequence that is at least 45%, 50%, 55%, 60%, 65%, 70%, 75%, 80%, 85%, 86%, 87%, 88%, 89%, 90%, 92%, 95%, 96%, 97%, 98%, or 99%, identical to an amino acid sequence selected from the group consisting of SEQ ID Nos.: 36-40.

In some embodiments, the StAMP with reduced renal toxicity is administered to a subject to treat an antibiotic-resistant bacterial infection. In some embodiments, the StAMP with reduced renal toxicity damages fewer kidney cells when administered to a subject relative to the StAMP that is identical except that it does not comprise an amino acid substitution that disrupts a hydrophobic patch and/or alters a cationic point charge. In some embodiments, the StAMP with reduced renal toxicity damages fewer kidney cells when administered to a subject relative to a StAMP that is identical except that it does not comprise an amino acid substitution that disrupts a hydrophobic patch and/or alters a cationic point charge. In some embodiments, the damage to kidney cells is monitored in the subject by serial serum creatinine measurements. In some embodiments, the subject is a human.

In some embodiments, the StAMP with reduced renal toxicity lyses fewer primary renal proximal tubule epithelial cells (pRPTECs) in an in vitro renal toxicity assay relative to the StAMP that is identical except that it does not comprise an amino acid substitution that disrupts a hydrophobic patch and/or alters a cationic point charge. In some embodiments, the StAMP with reduced renal toxicity maintains normal serum creatinine levels when administered in vivo relative to an elevation that may occur with a StAMP that is identical except that it does not comprise an amino acid substitution that disrupts a hydrophobic patch and/or alters a cationic point charge.

In another aspect, the disclosure relates to a stapled and/or stitched anti-microbial peptide (StAMP) having the formula:

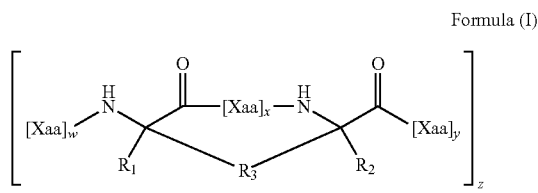

Formula (I)

or a pharmaceutically acceptable salt thereof,
wherein:
each $R_1$ and $R_2$ is independently H, alkyl, alkenyl, alkynyl, arylalkyl, cycloalkylalkyl, heteroarylalkyl, or heterocyclylalkyl, any of which is substituted or unsubstituted;
each $R_3$ is independently alkylene, alkenylene, or alkynylene, any of which is substituted or unsubstituted;
each x is independently 1, 2, 3, 4, 5, 6, 7, 8, 9, or 10;
each w and y is independently 1, 2, 3, 4, 5, 6, 7, 8, 9, 10, 11, 12, 13, 14, 15, 16, 17, 18, 19, or 20;
z is 1, 2, 3, 4, 5, 6, 7, 8, 9, or 10; and
each Xaa is independently an amino acid,
wherein the StAMP exhibits an antimicrobial effect against at least one microbe, and wherein
the $[Xaa]_w$ and/or $[Xaa]_y$ of the StAMP comprises at least one hydrophobic patch of two or more hydrophobic amino acids that is identical to a hydrophobic patch present on an anti-microbial peptide (AMP) that is identical to the StAMP of Formula I except that at least one of the two or more hydrophobic amino acids of the hydrophobic patch of the StAMP is substituted with an amino acid having reduced hydrophobicity;
and/or the StAMP comprises an amino acid substitution that alters the charge nature of a cationic point charge relative an anti-microbial peptide (AMP) that is identical to the StAMP of Formula I.

In some embodiments, the StAMP comprises an α-helix.

In some embodiments, the anti-microbial peptide (AMP) comprises an amino acid selected from the group consisting of: SEQ ID Nos.: 4-33. In some embodiments, the StAMP comprises an amino acid sequence that is at least 45%, 50%, 55%, 60%, 65%, 70%, 75%, 80%, 85%, 86%, 87%, 88%, 89%, 90%, 92%, 95%, 96%, 97%, 98%, or 99%, to an amino acid sequence selected from the group consisting of: SEQ ID Nos.: 36-41. In some embodiments, the StAMP comprises or consists of an amino acid sequence selected from the group consisting of: SEQ ID NO: 36-41.

In some embodiments, the $[Xaa]_w$ and/or $[Xaa]_y$ of the StAMP comprises at least one hydrophobic patch that has been disrupted with an amino acid substitution relative to the anti-microbial peptide (AMP).

In some embodiments, at least one amino acid on the hydrophilic portion of the α-helix of the StAMP is substituted with a lysine. In some embodiments, the StAMP exhibits greater anti-microbial activity relative to a StAMP that is identical except that it does not comprise a lysine substitution on the hydrophilic portion of its α-helix. In some embodiments, the StAMP comprises one amino acid substitution that alters one cationic point charge relative to the anti-microbial peptide (AMP). In some embodiments, the StAMP comprises at least two amino acid substitutions that alter at least two cationic point charges relative to the AMP. In some embodiments, the amino acid substitution comprises a lysine that is substituted with an arginine, histidine, or ornithine.

In some embodiments, the StAMP is administered to a subject to treat an antibiotic-resistant bacterial infection. In some embodiments, the StAMP damages fewer kidney cells when administered to a subject relative to a StAMP that is identical except that it does not comprise an amino acid substitution that disrupts a hydrophobic patch and/or alters a cationic point charge. In some embodiments, the damage to kidney cells is monitored in the subject by serial serum creatinine measurements. In some embodiments, the subject is a human.

In another aspect, the disclosure relates to a pharmaceutical composition comprising any of the stapled and/or stitched anti-microbial peptides (StAMPs) described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

DESCRIPTION OF DRAWINGS

FIG. 3 depicts levels of pRPTEC lysis following a 48-hour incubation with increasing concentrations of Mag (i+4)1,15(A9K) (SEQ ID NO: 1) or an analogue of Mag(i+4)1,15(A9K) (SEQ ID Nos.: 42-43), as measured using a lactate dehydrogenase (LDH) release assay (% LDH release).

FIG. 4 is a table providing data regarding StAMP antibacterial activity against several Gram-negative pathogens having different resistance patterns.

DETAILED DESCRIPTION

Figure 1:
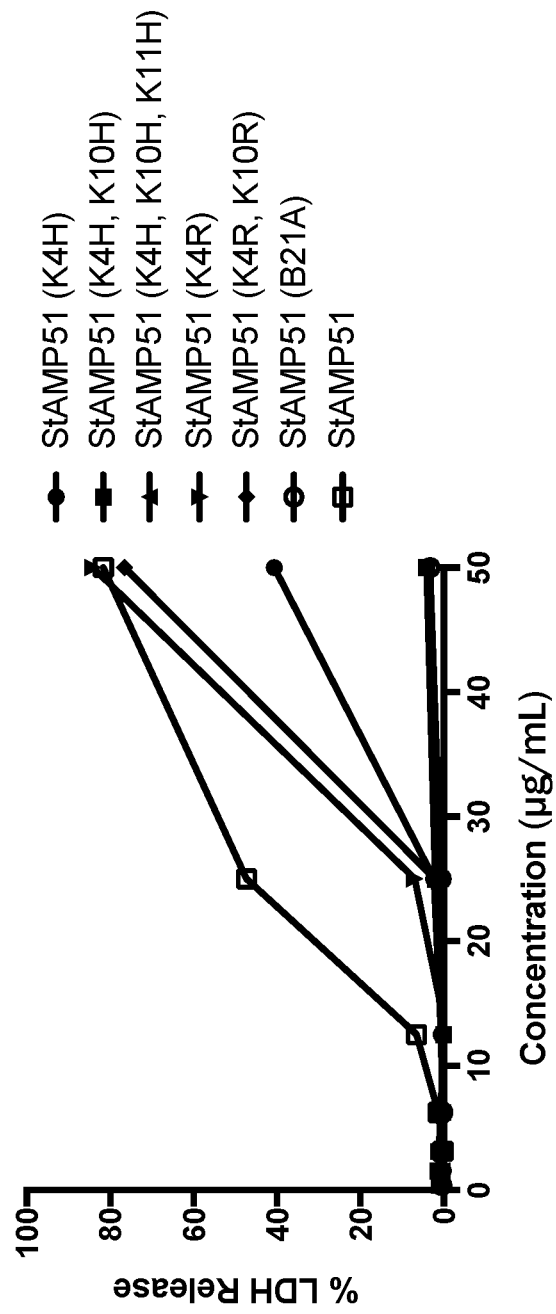
FIG. 1 depicts levels of primary proximal tubule epithelial cell (pRPTEC) lysis following a 24-hour incubation with increasing concentrations of Mag(i+4)1,15(A9K) (SEQ ID NO: 1) or an analogue of Mag(i+4)1,15(A9K) (SEQ ID Nos.: 36-41), as measured using a lactate dehydrogenase (LDH) release assay (% LDH release).

The present disclosure provides methods of treating bacterial infections of human subjects, animals (e.g., livestock), or plants, including antibiotic-resistant bacterial infections. In certain instances, the methods find use in the treatment of antibiotic-resistant Gram-negative bacterial infections. In some embodiments, the antibiotic that the bacteria is resistant to is selected from the group consisting of: carbapenem, an aminoglycoside, vancomycin, methicillin, clarithromycin, cephalosporin, penicillin, ampicillin, fluoroquinolone, tetracycline, and a β-lactam. In certain instances, the methods are useful to treat antibiotic-resistant Gram-positive bacterial infections.

In one particular aspect, the disclosure features methods of treating Gram-negative colistin-resistant bacterial infections in a human subject, animal, or plant, and methods for the development of stabilized (e.g., stapled and/or stitched (e.g., hydrocarbon-stapled and/or stitched)) antimicrobial peptides (StAMPs) that overcome Gram-negative colistin-resistance.

Treatment of patients with antibiotics has led to the development of resistance to almost all antibiotic classes (e.g., fluoroquinolones, tetracyclines, and β-lactams). Accordingly, there is a need for treatments for antibiotic-resistant bacterial infections. The only remaining treatment option for patients with chronic Gram-negative infections has become colistin, a cationic cyclic polypeptide. However, reports of colistin-resistant clinical isolates (e.g., colistin-resistant *A. baumannii* infections) has steadily risen, suggesting that this last line of treatment will soon become obsolete. In addition, a new plasmid, MCR-1, was recently discovered in *E. coli* isolated that confers colistin-resistance unto these pathogens and allows the resistance to spread rapidly to other Gram-negative bacterial species (e.g., *Klebsiella pneumonia*). Given that there are currently no viable drug candidates in the antibiotic pipeline that can address this problem, this disclosure features a platform from which new agents against colistin-resistant bacteria can be generated with potent and selective activity. In light of these dangerous developments, the present inventors have generated stabilized (e.g., stapled and/or stitched) antimicrobial peptides (StAMPs) that overcome colistin-resistance in Gram-negative bacteria. Furthermore, this disclosure provides a platform from which new StAMPs can be generated that reinforce the alpha-helical structure of antimicrobial peptides while greatly increasing their potency and selectivity against colistin-resistant bacteria. When tested against various clinical isolates of *A. baumannii* and *E. coli*, StAMPs consistently displayed potent antimicrobial activity independent of the pathogen's sensitivity to colistin. These results confirm that StAMPs have the potential to be a viable treatment option in patients where colistin-resistance has been developed.

Gram-Negative Bacteria

Gram-negative bacteria were first defined by their ability not to retain Gram staining, however, since then Gram-negative bacteria have been further defined as bacteria that has an outer membrane that contains porins and/or hydrophilic channels, and a cell wall thickness of 8-12 nm. Non-limiting examples of Gram-negative bacteria include: *Acinetobacter baumannii, Anaplasma* species, bacterial vaginosis microbiota, *Bacteroides* species, *Bartonella, Brucella* species, Enterobacteriaceae, *Burkholderia cepacia* and other *Burkholderia* species, *Campylobacter* species, *Bartonella bacilliformis, Bartonella henselae, Haemophilus ducreyi, Chlamydia trachomatis, Chlamydophila pneumoniae, Vibrio cholera Ehrlichia* species, *Rickettsia prowazekii, Fusobacterium* species, *Burkholderia mallei, Neisseria gonorrhoeae, Klebsiella granulomatis, Haemophilus influenza, Helicobacter pylori, Escherichia coli* O157:H7, O111 and O104:H4, *Ehrlichia ewingii, Anaplasma phagocytophilum, Ehrlichia chaffeensis, Kingella kingae, Legionella*

*pneumophila, Leptospira* species, *Borrelia burgdorferi, Borrelia garinii, Borrelia afzelii, Burkholderia pseudomallei, Neisseria meningitides, Rickettsia typhi, Mycoplasma pneumoniae, Bordetella pertussis, Yersinia pestis, Prevotella* species, *Chlamydophila psittaci, Coxiella burnetii, Borrelia hermsii, Borrelia recurrentis, Borrelia* species, *Rickettsia* species, *Rickettsia akari, Rickettsia, Salmonella* species, *Shigella* species, *Treponema pallidum, Francisella tularensis, Salmonella enterica* subsp. *enterica serovar typhi, Rickettsia, Ureaplasma urealyticum, Vibrio vulnificus, Vibrio parahaemolyticus, Yersinia pseudotuberculosis,* and *Yersinia enterocolitica.*

Gram-negative bacteria are responsible for the vast majority of bacterial infections, and most often develop antibiotic- and/or drug-resistance. In some embodiments of any of the methods described herein, the Gram-negative bacteria is colistin-resistant and confers colistin-resistance. In some embodiments of any of the methods described herein, the Gram-negative colistin-resistant bacterium is *Acinetobacter, Escherichia, Pseudomonas, Neisseria, Chlamydia, Yersinia, Proteus, Enterobacter, Serratia, Helicobacter, Salmonella, Shigella, Moraxella, Stenotrophomonas, Bdellovibrio,* an acetic acid bacterium, *Klebsiella,* or *Legionella.* In some embodiments of any of the methods described herein, the Gram-negative colistin-resistant bacterium is *A. baumannii, E. coli, Pseudomonas aeruginosa, Neisseria gonorrhoeae, Chlamydia trachomatis, Yersinia pestis, Proteus mirabilis, Enterobacter cloacae, Serratia marcescens, Helicobacter pylori, Salmonella enteritidis, Salmonella typhi, Shigella, Klebsiella pneumoniae, Legionella pneumophila,* or a Gram-negative bacterium that contains a MCR-1 plasmid.

In some embodiments, the Gram-negative colistin-resistant bacterial infection is an *A. baumannii* infection. In some embodiments, the Gram-negative colistin-resistant bacterial infection is an *E. coli* infection. In some embodiments, the Gram-negative colistin-resistant bacterial infection is a *Klebsiella pneumoniae* infection. In some embodiments, the Gram-negative colistin-resistant bacterial infection is from a Gram-negative bacterium that contains a MCR-1 plasmid. In some embodiments, the Gram-negative bacterium that contains a MCR-1 plasmid is *E. coli.* In some embodiments, the Gram-negative bacterium that contains a MCR-1 plasmid is *Klebsiella pneumoniae.*

Gram-Positive Bacteria

Gram-positive bacteria are defined by their ability to give a positive result in the Gram stain test. Gram-positive bacteria take up the crystal violet stain used in this test, thereby appearing to be purple-colored when seen through a microscope. This is explained by the fact that the thick peptidoglycan layer in the Gram-positive bacterial cell wall retains the stain after it is washed away from the rest of the sample, in the decolorization stage of the test. All gram-positive bacteria are bounded by a single-unit lipid membrane, and, in general, contain a thick layer (20-80 nm) of peptidoglycan. Non-limiting examples of Gram-positive bacteria include: *Actinomyces israelii, Actinomyces gerencseriae, Propionibacterium propionicus, Bacillus anthracis, Arcanobacterium haemolyticum, Bacillus cereus,* bacterial vaginosis microbiota, *Clostridium botulinum, Mycobacterium ulcerans,* Group A *Streptococcus* and *Staphylococcus, Clostridium difficile, Corynebacterium diphtheria, Enterococcus* species, *Clostridium perfringens,* other *Clostridium* species, *Streptococcus pyogenes, Streptococcus agalactiae, Mycobacterium leprae, Mycobacterium lepromatosis, Listeria monocytogenes, Nocardia asteroides, Nocardia* species, *Streptococcus pneumoniae, Staphylococcus aureus, Staphylococcus* species, *Clostridium tetani, Mycobacterium tuberculosis, Yersinia pseudotuberculosis,* and *Yersinia enterocolitica.*

In some embodiments, the Gram-positive antibiotic-resistant bacterial infection is a *S. aureus* infection.

Antibiotic-Resistance

The term "antibiotic-resistance" refers to a loss or reduction in the effectiveness of an antibiotic (e.g., an antimicrobial agent, an antimicrobial peptide, a hydrocarbon-stapled and/or stitched peptide) to kill or inhibit the growth of a bacterial strain that was once responsiveness to the antibiotic. In certain embodiments, an antibiotic has a cytostatic effect on a bacterium instead of having a cytotoxic effect. In certain embodiments, a bacterium can develop antibiotic-resistance by genetically altering (e.g., mutating) the antibiotic target-binding site. In certain embodiments, a bacterium can develop antibiotic-resistance by preventing (e.g., inhibiting or reducing) penetrance of the antibiotic into the bacterium (e.g., genetically mutating the docking site of the antibiotic, genetically mutating the antibiotic transport pump (e.g., increasing the efflux of the antibiotic)). In certain embodiments, a bacterium can develop antibiotic-resistance by acquiring an antibiotic-resistance gene (e.g., MCR-1 plasmid) by horizontal gene transfer (e.g., conjugation, transformation or transduction) from another bacterial strain. In certain embodiments, a bacterium can develop antibiotic-resistance by expressing enzymes that inactivate the antibiotic.

In some embodiments, a bacterium can develop antibiotic-resistance to one or more (e.g., 1, 2, 3, 4, 5, 6, 7, 8, 9, 10) classes of antibiotic. In some embodiments, the one or more classes of antibiotic is selected from the group consisting of: carbapenem, an aminoglycoside, vancomycin, methicillin, clarithromycin, cephalosporin, penicillin, ampicillin, fluoroquinolone, tetracycline, and a β-lactam.

In some embodiments of any of the methods described herein, a Gram-negative bacterium can have acquired resistance to an antibiotic (i.e. antibiotic-resistance). In some embodiments of any of the methods described herein, a Gram-negative bacterial infection can have acquired resistance to an antibiotic (i.e. an antibiotic-resistant Gram-negative bacterial infection (e.g., a colistin-resistant Gram-negative bacterial infection, a carbapenem-resistant Gram-negative bacterial infection). In some embodiments of any of the methods described herein, a subject can have acquired resistance to an antibiotic (e.g., colistin-resistance, carbapenem-resistance).

Stapled and/or Stitched Antimicrobial Peptides (StAMP)

The present disclosure provides structurally-stabilized and microbial-selective peptides related to anti-bacterial peptides (AMP) (e.g., StAMP) comprising at least two modified amino acids joined by an internal (intramolecular) cross-link (or staple), wherein the at least two amino acids are separated by, e.g., 2, 3, or 6 amino acids. Stabilized peptides herein can include, e.g., stapled (e.g., hydrocarbon-stapled) peptides, including peptides having, e.g., 1, 2, 3, 4, 5, or more staples and/or stitched peptides. Examples of such stabilized peptides are provided in Table 1. These stabilized peptides can be modified by amino acid substitutions, insertions, and/or deletions. In some instances, the stabilized peptides are one of SEQ ID Nos.: 1-3 or 36-43 with 1 to 5 (i.e., 1, 2, 3, 4, or 5) amino acid substitutions, insertions, and/or deletions. In some instances, the stabilized peptides are one of SEQ ID Nos.: 7, 9, 11, 13, 15, 17, 19, 21, 23, 25, 27, 29, 31, or 33 with 1 to 5 (i.e., 1, 2, 3, 4, or 5) amino acid substitutions, insertions, and/or deletions. In some instances, the stabilized peptides are one of SEQ ID Nos.: 1-3 or 36-43, with 1 to 5 (i.e., 1, 2, 3, 4, or 5) amino acid substitutions. In some instances, the stabilized peptides are one of SEQ ID Nos.: 7, 9, 11, 13, 15, 17, 19, 21, 23, 25, 27, 29, 31, or 33, with 1 to 5 (i.e., 1, 2, 3, 4, or 5) amino acid substitutions. These substitutions may be conservative amino acid substitutions. The modified or substituted stabilized peptide has the same or better antimicrobial activity as the parent stabilized peptide. Antimicrobial activity can be assayed as described in the Examples. In some instances, the stabilized peptides are one of SEQ ID Nos.: 1-3 or 36-43. In other instances, the stabilized peptides are one of SEQ ID Nos.: 7, 9, 11, 13, 15, 17, 19, 21, 23, 25, 27, 29, 31, or 33.

A "peptide" or "polypeptide" comprises a polymer of amino acid residues linked together by peptide (amide) bonds. The terms, as used herein, refer to proteins, polypeptides, and peptides of any size, structure, or function. Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. "Dipeptide" refers to two covalently linked amino acids.

AMPs can be divided into four main structural groups: stabilized β-sheet peptides with two to four disulfide bridges; loop peptides with a single disulfide bridge; α-helical peptides; and extended structures rich in arginine, glycine, proline, tryptophan, and histidine. Typically, 6 to 100 (e.g., 12 to 50) amino acids in length, these peptides are usually cationic with an amphipathic character. These biophysical properties allow them to interact with bacterial membranes resulting in either disruption of membrane integrity or translocation into bacterial cells and disruption of intracellular processes.

The alpha-helical structural motif of AMPs can be important to the ability of AMPs to interact with bacterial membranes. Upon binding to the membrane, AMPs can either translocate or insert themselves and permeabilize the membrane through a barrel-stave mechanism, a carpet-like mechanism or a toroidal pore mechanism. This process of permeabilization and disruption of membrane integrity can account for the antimicrobial properties of alpha-helical AMPs.

A stapled and/or stitched antimicrobial peptide (StAMP) provided herein can exhibit helical stability by the maintenance of α-helical structure as measured by circular dichroism or NMR. For example, in some aspects, the stapled and/or stitched anti-microbial peptide exhibits at least a 1.25, 1.5, 1.75 or 2-fold increase in α-helicity as determined by circular dichroism compared to a corresponding un-cross-linked peptide (i.e. a non-stapled and non-stitched peptide). In some aspects, the stapled and/or stitched (e.g., hydrocarbon-stapled and/or stitched) anti-microbial peptide can exhibit about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% helicity. Amino acids are the building blocks of the peptides herein. The term "amino acid" refers to a molecule containing both an amino group and a carboxyl group as well as a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), Leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnatural beta-amino acids. Amino acids used in the construction of peptides of the present disclosure can be prepared by organic synthesis, or obtained by other routes, such as, for example, degradation of or isolation from a natural source.

There are many known non-natural or unnatural amino acids any of which may be included in the peptides of the present disclosure. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, and glycosylated, to name a few.

Peptide Stapling

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (see, e.g., Blackwell et al., *J Org Chem.*, 66: 5291-5302, 2001; Angew et al., *Chem Int Ed.* 37:3281, 1994). As used herein, the term "peptide stapling" includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed, e.g., in WO 2008121767 and WO 2010/068684, which are both hereby incorporated by reference in their entirety. In some instances, staples, as used herein, can retain the unsaturated bond or can be reduced (e.g., as mentioned below in the stitching paragraph description).

While peptide staples can have all hydrocarbon cross-links, other type of cross-links or staples can also be used. For example, triazole-containing (e.g., 1, 4 triazole or 1, 5 triazole) crosslinks can be used (see, e.g., Kawamoto et al. 2012 *J Med Chem.* 55:1137; WO 2010/060112). In addition, other methods of performing different types of stapling are well known in the art (see, e.g., *Lactam stapling*: Shepherd et al., *J. Am. Chem. Soc.*, 127:2974-2983 (2005); *UV-cycloaddition stapling*: Madden et al., *Bioorg. Med. Chem. Lett.*, 21:1472-1475 (2011); *Disulfide stapling*: Jackson et al., *Am. Chem. Soc.*, 113:9391-9392 (1991); *Oxime stapling*: Haney et al., *Chem. Commun.*, 47:10915-10917 (2011); *Thioether stapling*: Brunel and Dawson, *Chem. Commun.*, 552-2554 (2005); *Photoswitchable stapling*: J. R. Kumita et al., *Proc. Natl. Acad. Sci. U.S.A,* 97:3803-3808 (2000); *Double-click stapling*: Lau et al., *Chem. Sci.*, 5:1804-1809 (2014); *Bis-lactam stapling*: J. C. Phelan et al., *J. Am. Chem. Soc.*, 119:455-460 (1997); and *Bis-arylation stapling*: A. M. Spokoyny et al., *J. Am. Chem. Soc.*, 135:5946-5949 (2013)).

Stapling of a peptide using an all-hydrocarbon cross-link has been shown to help maintain its native conformation and/or secondary structure, particularly under physiologically relevant conditions (see, e.g., Schafmiester et al., *J Am Chem Soc.*, 122:5891-5892, 2000; Walensky et al., *Science*, 305:1466-1470, 2004).

Stapling the polypeptide herein by an all-hydrocarbon crosslink predisposed to have an alpha-helical secondary structure can improve stability and various pharmacokinetic properties.

Stabilized peptides herein include at least two internally cross-linked or stapled amino acids, wherein the at least two amino acids are separated, e.g., by two (i.e., i, i+3), three (i.e., i, i+4), or six (i.e., i, i+7) amino acids. While at least two amino acids are required to support an internal cross-link (e.g., a staple), additional pairs of internally cross-linked amino acids can be included in a peptide, e.g., to support additional internal cross-links (e.g., staples). For example, peptides can include 1, 2, 3, 4, 5, or more staples. Examples of peptide staples are illustrated in the figures. Cross-linked peptides (e.g., stapled and/or stitched peptides) are generally referred to herein as stapled and/or stitched antimicrobial (StAMP) peptides (e.g., hydrocarbon-stapled and/or stitched peptides).

Alternatively, or in addition, peptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid) forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids (e.g., i, i−3, i, i−4, i, i−7). The number of amino acids on either side of the core (e.g., between the core amino acid and an amino acid cross-linked to the core) can be the same or different.

In some aspects, peptides herein can include a combination of at least one (e.g., 1, 2, 3, 4, or 5) staple and at least one (e.g., 1, 2, 3, 4, or 5) stitch.

Cross-linked peptides (e.g., stapled and/or stitched peptides) are generally referred to herein as StAMP peptides. Peptides can include cross-linked amino acids at one or more of the positions.

Selection of amino acids for modification (e.g., to support an internal cross-link) can also be facilitated by staple scanning. The terms "staple scan" and "staple walk" refer interchangeably to the synthesis of a library of stapled peptides whereby the location of the i and i+3; i and i+4; and i and i+7 single and multiple staple, or stitches, are positioned sequentially down the length of the peptide sequence, sampling all possible positions, to identify desired, effective, suitable, or optimal properties and activities for the stapled or stitched constructs. Examples of staple scanning methods are illustrated in the figures.

Suitable tethers are described herein and in, e.g., US2005/0250680, PCT/US2008/058575, WO 2009/108261, and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain aspects, a "terminally unsaturated amino acid side chain" is a terminal olefinic amino acid side chain. In certain aspects, a "terminally unsaturated amino acid side chain" is a terminal acetylenic amino acid side chain. In certain aspects, the terminal moiety of a "terminally unsaturated amino acid side chain" is not further substituted.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (see, e.g., Bang, et al., *J. Am. Chem. Soc.* 126:1377). Alternately, large peptides are routinely synthesized using a convergent approach whereby fully protected fragments are specifically and sequentially reacted to form the full length desired product, after final deprotection, such as in the industrial synthesis of Fuzeon.

Methods of Making a Stapled and/or Stitched Antimicrobial Peptide

Methods suitable for obtaining (e.g., synthesizing), stapling, and purifying the peptides disclosed herein are also known in the art (see, e.g., Bird et. al., *Meth Enzymol.*, 446:369-386 (2008); Bird et al, *Curr Protoc Chem Biol.*, 2011; Walensky et al., *Science*, 305:1466-1470 (2004); Schafmeister et al., *J Am Chem Soc.*, 122:5891-5892 (2000); U.S. Patent Application Publication No. 2010/0168388; and U.S. Pat. No. 7,723,468, issued May 25, 2010, each of which are hereby incorporated by reference in their entirety).

Any of the methods disclosed herein can include a StAMP selected from, or prepared using an AMP from, Table 1. In some embodiments of any of the methods disclosed herein, the StAMP comprises or consists of the amino acid sequence set forth in any one of SEQ ID Nos.: 1-33 or 36-43, except for 1 to 5 amino acids substitutions, insertions and/or deletions. In some embodiments of any of the methods disclosed herein, the StAMP comprises or consists of an amino acid sequence that is at least 45%, 50%, 55%, 60%, 65%, 70%, 75%, 80%, 85%, 90%, 91%, 92%, 93%, 94%, 95%, 96%, 97%, 98%, or 99% identical to the amino acid sequence set forth in any one of SEQ ID Nos.: 1-33 or 36-43. In some embodiments of any of the methods disclosed herein, the StAMP comprises or consists of the amino acid sequence set forth in any one of SEQ ID Nos.: 1-33 or 36-43. In some embodiments of any of the methods disclosed herein, the StAMP comprises or consists of the amino acid sequence set forth in any one of SEQ ID Nos.: 1-3 or 36-43, except for 1 to 5 (e.g., 1, 2, 3, 4 or 5) amino acids substitutions, insertions and/or deletions. In some embodiments of any of the methods disclosed herein, the StAMP comprises or consists of the amino acid sequence set forth in any one of SEQ ID Nos.: 7, 9, 11, 13, 15, 17, 19, 21, 23, 25, 27, 29, 31, or 33, except for 1 to 5 (e.g., 1, 2, 3, 4 or 5) amino acids substitutions, insertions and/or deletions. In some embodiments of any of the methods disclosed herein, the StAMP comprises or consists of an amino acid sequence that is at least 45%, 505, 55%, 60%, 65%, 70%, 75%, 80%, 85%, 90%, 91%, 92%, 93%, 94%, 95%, 96%, 97%, 98%, or 99% identical to the amino acid sequence set forth in any one of SEQ ID Nos.: 1-3 or 36-43. In certain instances, in determining the identity between these amino acid sequences, conservative amino acid substitutions are considered to be "identical." In some embodiments of any of the methods disclosed herein, the StAMP comprises or consists of an amino acid sequence that is at least 45%, 50%, 55%, 60%, 65%, 70%, 75%, 80%, 85%, 90%, 91%, 92%, 93%, 94%, 95%, 96%, 97%, 98%, or 99% identical to the amino acid sequence set forth in any one of SEQ ID Nos.: 7, 9, 11, 13, 15, 17, 19, 21, 23, 25, 27, 29, 31, or 33. In certain instances, in determining the identity between these amino acid sequences, conservative amino acid substitutions are considered to be "identical." In some embodiments of any of the methods disclosed herein, the StAMP comprises or consists of the amino acid sequence set forth in any one of SEQ ID Nos.: 1-3 or 36-43. In some embodiments of any of the methods disclosed herein, the StAMP comprises or consists of the sequence of any one of SEQ ID Nos.: 7, 9, 11, 13, 15, 17, 19, 21, 23, 25, 27, 29, 31, or 33.

TABLE 1

List of Antimicrobial Peptides

| Name | SEQUENCE | SEQ ID NO: |
|---|---|---|
| Mag(i+4)1,15(A9K) | GXGKFXHSKKKFGKAXVGEXBNS | 1 |
| Mag(i+4)2,15(A9K) | GIXKFLXSKKKFGKAXVGEXBNS | 2 |
| Pleu(i+4)1,15(A9K) | GXGSFXKKKAHVGKHXGKAXLTHYL | 3 |
| Magainin | GIGKFLHSAKKFGKAFVGEIMNS | 4 |
| Pexiganan | GIGKFLKKAKKFGKAFVKILKK | 5 |
| Pleurocidin | GWGSFFKKAAHVGKHVGKAALTHYL | 6 |
| Pleurocidin | GWGSFFKKAAHXGKHVGKXALTHYL | 7 |
| Pardaxin | GFFALIPKIISSPLFKTLLSAVGSALSSSGEQE | 8 |
| Pardaxin | GFFALIPKIISXPLFKTLXSAVGSALSSSGEQE | 9 |
| Hagfish Intestinal Antimicrobial Peptide (HFIAP) | GFFKKAWRKVKHAGRRVLKKGVGRHYVNNWLK | 10 |
| HFIAP | GFFKKAWRKVKHAXRRVLKKXVGRHYVNNWLK | 11 |
| PGQ | GVLSNVIGYLKKLGTGALNAVLKQ | 12 |
| PGQ | GVLSNVIGYLKKLXTGALNAXLKQ | 13 |
| Buforin II | TRSSRAGLQFPVGRVHRLLRK | 14 |
| Buforin II | TRSSRAGLQFPXGRVHRLXRK | 15 |
| Dermaseptin | ALWKTMLKKLGTMALHAGKAALGAAAD TISQGTQ-NH2 | 16 |
| Dermaseptin | ALWKTMLKKLGTMXLHAGKAXLGAAAD TISQGTQ-NH2 | 17 |
| Caerin | GLFKVLGSVAKHLLPHVVPVIAEKL-NH2 | 18 |
| Caerin | GLFKVLGSVAKHLXPHVVPVXAEKL-NH2 | 19 |
| Melittin | GIGAVLKVLTTGLPALISWIKRKRQQ-NH2 | 20 |
| Melittin | GIGAVLKVLTTGXPALISWXKRKRQQ-NH2 | 21 |
| Cecropin A | KWKLFKKIEKVGQNIRDGIIKAGPAVAV VGQATQIAK-NH2 | 22 |

TABLE 1-continued

List of Antimicrobial Peptides

| Name | SEQUENCE | SEQ ID NO: |
|---|---|---|
| Cecropin A | KWKXFKKIEKXGQNIRDGIIKAGPAVAV VGQATQIAK-NH2 | 23 |
| Lycotoxin I | KIKWFKTMKSIAKFIAKEQMKKHLG GE-COOH | 24 |
| Lycotoxin I | KIKWFKTXKSIAKFXAKEQMKKHLG GE-COOH | 25 |
| Styelins B | GFGPAFHSVSNFAKKHKTA-NH2 | 26 |
| Styelins B | GFGPXFHSVSNXAKKHKTA-NH2 | 27 |
| Clavanin B | VFQFLGRIIHHVGNFVHGFSHVF-NH2 | 28 |
| Clavanin B | VFQFXGRIIHHXGNFVHGFSHVF-NH2 | 29 |
| Cathelicidin A | ILKKWPWWPWRRK-NH2 | 30 |
| Cathelicidin A | IXKKWPWWXWRRK-NH2 | 31 |
| Dermicidin | SSLLEKGLDGAKKAVGGLGKLGKDAV EDLESVGKGAVHDVKDVLDSVL-COOH | 32 |
| Dermicidin | SSLLEKGLDGXKKAVGGXGKLGKDAV EDLESVGKGAVHDVKDVLDSVL-COOH | 33 |
| Mag(i+4)1,15(A9K, K4H) | GXGHFXHSKKKFGKAXVGEXBNS | 36 |
| Mag(i+4)1,15(A9K, K4H, K10H) | GXGHFXHSKHKFGKAXVGEXBNS | 37 |
| Mag(i+4)1,15(A9K, K4H, K10H, K11H) | GXGHFXHSKHHFGKAXVGEXBNS | 38 |
| Mag(i+4)1,15(A9K, K4R) | GXGRFXHSKKKFGKAXVGEXBNS | 39 |
| Mag(i+4)1,15(A9K, K4R, K10R) | GXGRFXHSKRKFGKAXVGEXBNS | 40 |
| Mag(i+4)1,15(A9K, B21A) | GXGKFXHSKKKFGKAXVGEXANS | 41 |
| Mag(i+4)1,15(A9K, B21K) | GXGKFXHSKKKFGKAXVGEXKNS | 42 |
| Mag(i+4)1,15(A9K, B21A, N22K, S23K) | GXGKFXHSKKKFGKAXVGEXAKK | 43 |

In certain embodiments, the X's in the sequences above are the same amino acid (e.g., same non-natural amino acid). In other embodiments, the X's are different amino acids (e.g., different non-natural amino acids). In certain instances, the X's are non-natural amino acids comprising olefinic side chains. In certain cases, the locations of the X's in the above sequences can be altered so long as "the partner residues" (i.e., those that are involved in forming a staple/stitch) are separated by at least 2, 3, or 6 amino acids. In some cases, at least one of the "W's" in the above sequences is a brominated Trp residue. In other cases, all of the "W's" in the above sequences are brominated Trp residues. In certain embodiments, the X is selected from the group consisting of (S)-2-(4-pentenyl)Ala-OH, (R)-2-(4-pentenyl)Ala-OH, (R)-2-(7-octenyl)Ala-OH, (S)-2-(7-octenyl)Ala-OH and 2-amino-2-(pent-4-enyl)hept-6-enoic acid, (R)-2-(2-propenyl)Ala-OH, (S)-2-(2-propenyl)Ala-OH. In certain embodiments, if a sequence has two "X's" both X's are (S)-2-(4-pentenyl)Ala-OH. In certain embodiments, if a sequence has two "X's" both X's are (R)-2-(4-pentenyl)Ala-OH. In certain embodiments, if a sequence has two "X's" both X's are (R)-2-(7-octenyl)Ala-OH. In certain embodiments, if a sequence has two "X's" both X's are (S)-2-(7-octenyl)Ala-OH. In certain embodiments, if a sequence has two "X's" both X's are 2-amino-2-(pent-4-enyl)hept-6-enoic acid. In certain embodiments, if a sequence has two "X's" both X's are (R)-2-(2-propenyl)Ala-OH. In certain embodiments, if a sequence has two "X's" both X's are (R)-2-(2-propenyl)Ala-OH. In certain embodiments, if a sequence has two "X's" both X's are (S)-2-(2-propenyl)Ala-OH. In certain embodiments, if a sequence has two "X's" both X's are different non-natural amino acids and can, e.g., be selected from the group consisting of S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, and (S)-2-(2-propenyl)Ala-OH. In certain instances, if the two X's are separated by 3 amino acids, the two X's can be different non-natural residues, e.g., the first X is (R)-2-(2-propenyl)Ala-OH or (S)-2-(2-propenyl)Ala-OH and the second X is (S)-2-(2-propenyl)Ala-OH or (R)-2-(2-propenyl)Ala-OH. In certain instances, the "X's" that are in SEQ ID Nos.: 1-3, 7, 9, 11, 13, 15, 17, 19, 21, 23, 25, 27, 29, 31, 33, 34, 35, or 36-43 or inserted into SEQ ID Nos.: 4-6, 8, 10, 12, 14, 16, 18, 20, 22, 24, 26, 28, 30, or 32 can be any residue/substance that permits formation of a staple and/or stitch. In other words, the staple and/or stitch does not need to be a hydrocarbon-staple and/or stitch. Methods of performing different types of stapling are well known in the art. In certain instances, the "X's" that are in SEQ ID Nos.: 1-3, 7, 9, 11, 13, 15, 17, 19, 21, 23, 25, 27, 29, 31, 33, 34, 35, or 36-43 or inserted into SEQ ID Nos.: 4-6, 8, 10, 12, 14, 16, 18, 20, 22, 24, 26, 28, 30, or 32 can be any residue that permits formation of a hydrocarbon staple and/or stitch. In certain instances, the peptides with the sequences recited in SEQ ID Nos.: 1-3, 7, 9, 11, 13, 15, 17, 19, 21, 23, 25, 27, 29, 31, 33, 34, 35, or 36-43 or modified peptides with the sequences recited in SEQ ID Nos.: 4-6, 8, 10, 12, 14, 16, 18, 20, 22, 24, 26, 28, 30, or 32 are lactam stapled. In other instances, the peptides with the sequences recited in SEQ ID Nos.: 1-3, 7, 9, 11, 13, 15, 17, 19, 21, 23, 25, 27, 29, 31, 33, 34, 35, or 36-43 or modified peptides with the sequences recited in SEQ ID Nos.: 4-6, 8, 10, 12, 14, 16, 18, 20, 22, 24, 26, 28, 30, or 32 are triazole stapled. In other instances, the peptides with the sequences recited in SEQ ID Nos.: 1-3, 7, 9, 11, 13, 15, 17, 19, 21, 23, 25, 27, 29, 31, 33, 34, 35, or 36-43 or modified peptides with the sequences recited in SEQ ID Nos.: 4-6, 8, 10, 12, 14, 16, 18, 20, 22, 24, 26, 28, 30, or 32 are stapled using a UV-cycloaddition staple. In other instances, the peptides with the sequences recited in SEQ ID Nos.: 1-3, 7, 9, 11, 13, 15, 17, 19, 21, 23, 25, 27, 29, 31, 33, 34, 35 or 36-43 or modified peptides with the sequences recited in SEQ ID Nos.: 4-6, 8, 10, 12, 14, 16, 18, 20, 22, 24, 26, 28, 30, or 32 are disulfide stapled. In other instances, the peptides with the sequences recited in SEQ ID Nos.: 1-3, 7, 9, 11, 13, 15, 17, 19, 21, 23, 25, 27, 29, 31, 33, 34, 35 or 36-43 or modified peptides with the sequences recited in SEQ ID Nos.: 4-6, 8, 10, 12, 14, 16, 18, 20, 22, 24, 26, 28, 30, or 32 are oxime stapled. In other instances, the peptides with the sequences recited in SEQ ID Nos.: 1-3, 7, 9, 11, 13, 15, 17, 19, 21, 23, 25, 27, 29, 31, 33, 34, 35 or 36-43 or modified peptides with the sequences recited in SEQ ID Nos.: 4-6, 8, 10, 12, 14, 16, 18, 20, 22, 24, 26, 28, 30, or 32 are thioether stapled. In other instances, the peptides with the sequences recited in SEQ ID Nos.: 1-3, 7, 9, 11, 13, 15, 17, 19, 21, 23, 25, 27, 29, 31, 33, 34, 35 or 36-43 or modified peptides with the sequences recited in SEQ ID Nos.: 4-6, 8, 10, 12, 14, 16, 18, 20, 22, 24, 26, 28, 30, or 32 comprise a photoswitchable staple. In other instances, the peptides with the sequences recited in SEQ ID Nos.: 1-3, 7, 9, 11, 13, 15, 17, 19, 21, 23, 25, 27, 29, 31, 33, 34, 35 or 36-43 or modified peptides with the sequences recited in SEQ ID Nos.: 4-6, 8, 10, 12, 14, 16, 18, 20, 22, 24, 26, 28, 30, or 32 are double-click stapled. In other instances, the peptides with the sequences recited in SEQ ID Nos.: 1-3, 7, 9, 11, 13, 15, 17, 19, 21, 23, 25, 27, 29, 31, 33, 34, 35 or 36-43 or modified peptides with the sequences recited in SEQ ID Nos.: 4-6, 8, 10, 12, 14, 16, 18, 20, 22, 24, 26, 28, 30, or 32 are bis-lactam stapled. In other instances, the peptides with the sequences recited in SEQ ID Nos.: 1-3, 7, 9, 11, 13, 15, 17, 19, 21, 23, 25, 27, 29, 31, 33, 34, 35 or 36-43 or modified peptides with the sequences recited in SEQ ID Nos.: 4-6, 8, 10, 12, 14, 16, 18, 20, 22, 24, 26, 28, 30, or 32 comprise a bis-arylation staple.

In some instances of any of the methods provided herein, the StAMP can include (e.g., comprise, consist essentially of, or consist of) at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or more contiguous amino acids of a sequence selected from Table 1, wherein the peptide has a reinforced or stabilized alpha helical secondary structure (e.g., wherein the peptide includes at least one internal crosslink).

In some aspects, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50%, or 60% DMSO. In a specific aspect, a 50%/50% DMSO/NMP solution is used. The solution may be incubated for a period of 1, 6, 12, or 24 hours, following which the resin may be washed, for example with dichloromethane or NMP. In one aspect, the resin is washed with NMP. Shaking and bubbling an inert gas into the solution may be performed.

Properties of the cross-linked polypeptides of the disclosure can be assayed, for example, using the methods described below, and throughout the specification.

Hydrophobicity Assays

Various methods are known by those in the art to calculate or to experimentally-determine the hydrophobicity of a peptide or polypeptide (e.g., a hydrocarbon-stapled and/or stitched antimicrobial peptide). Non-limiting examples of such techniques include: hydrophilicity plots; hydropathy plots; Kyte-Doolittle hydrophobicity plots; von Heijne; hydrophobic moment; CCS; Kyle and Eisen scales; and high performance liquid chromatography (HPLC). In some embodiments of any of the methods described herein, the hydrophobicity of a stapled and/or stitched peptide (e.g., hydrocarbon-stapled and/or stitched peptide) can be determined using bioinformatics tools (e.g., ExPASy (www.expasy.org); or HeliQuest (heliquest.ipmc.cnrs.fr/cgi-bin/ComputParamsV2.py). In some embodiments, the hydrophobicity of a stapled and/or stitched antimicrobial peptide is calculated (e.g., calculated hydrophobicity). In some embodiments, the hydrophobicity of a stapled and/or stitched antimicrobial peptide is determined experimentally. In some embodiments, a helical wheel is generated to visually highlight amphipathicity along a helix. Hydrophobic patches within a peptide or protein may be identified using techniques generally known in the art, including, e.g., computational prediction/simulation (e.g., using ExPASy ProtScale, available at web.expasy.org/protscale/, Scoobydomain prediction, available at www.ibi.vu.nl/programs/scoobywww/, PSIPRED, available at bioinf.cs.ucl.ac.uk/psipred/, hydrophobic cluster analysis, see, e.g., www.impmc.upmc.fr/~callebau/HCA.html, Kyte Doolittle plotting, available at, e.g., gcat.davidson.edu/DGPB/kd/kyte-doolittle.htm or www.vivo.colostate.edu/molkit/hydropathy/index.html, and/or SPLIT, available at split.pmfst.hr/split/4/) and/or experimental determination (e.g., using techniques involving NMR spectroscopy, electron microscopy, homology modeling, small-angle X-ray and/or neutron scattering (SAXS/SANS), and/or X-ray crystallography) of the structure of the peptide or protein.

Alpha-Helicity Assays

The alpha-helicity of a peptide of interest can be determined by any method known in the art. In some cases, circular dichroism or nuclear magnetic resonance spectroscopy (NMR) may be employed. Peptides are dissolved in an aqueous solution (e.g., 5 mM potassium phosphate solution at pH 7, or distilled $H_2O$, to concentrations of 25-50 µM). Circular dichroism (CD) spectra are obtained on a spectropolarimeter (e.g., Jasco J-710, Aviv) using standard measurement parameters (e.g., temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

In some embodiments of any of the methods described herein, a stapled and/or stitched antimicrobial peptide (StAMP) that has a percent α-helicity of 40% to 90%, 40% to 85%, 40% to 80%, 40% to 75%, 40% to 70%, 40% to 65%, 40% to 60%, 40% to 55%, 40% to 50%, 45% to 90%, 45% to 85%, 45% to 80%, 45% to 75%, 45% to 70%, 45% to 65%, 45% to 60%, 45% to 55%, 45% to 50%, 50% to 90%, 50% to 85%, 50% to 80%, 50% to 75%, 50% to 70%, 50% to 65%, 50% to 60%, 50% to 55%, 55% to 90%, 55% to 85%, 55% to 80%, 55% to 75%, 55% to 70%, 55% to 65%, 55% to 60%, 60% to 90%, 60% to 85%, 60% to 80%, 60% to 75%, 60% to 70%, 60% to 65%, 65% to 90%, 65% to 85%, 65% to 80%, 65% to 75%, 65% to 70%, 70% to 90%, 70% to 85%, 70% to 80%, 70% to 75%, 75% to 90%, 75% to 85%, 75% to 80%, 80% to 90%, 80% to 85%, 85% to 90%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, or 90%. In certain embodiments, a StAMP has a percent α-helicity of 15% to 20%, 15% to 25%, 15% to 30%, or 20% to 40%. In certain instances, this percent α-helicity of the StAMP increases once it contacts a cell membrane (e.g., a membrane of a Gram-negative bacterium).

A non-limiting example of a stapled and/or stitched antimicrobial peptide (StAMP) that has a relatively high ability to inhibit the growth of a Gram-negative colistin-resistant bacterium and/or bacterial species that contains a MCR-1 plasmid, and a relatively low ability to lyse or inhibit the growth of a mammalian cell can have a minimum inhibitory concentration (MIC) between about 0.1 μM and about 50 μM, or between about 0.5 μM and about 20 μM. In some cases, the MIC is determined as described in Example 1. The MIC of any stapled and/or stitched anti-microbial peptides (e.g., hydrocarbon-stapled and/or stitched peptide) described herein can be about 0.1 μM, about 0.2 μM, about 0.3 μM, about 0.4 μM, about 0.5 μM, about 0.6 μM, about 0.7 μM, about 0.8 μM, about 0.9 μM, about 1 μM, about 1.1 μM, about 1.2 μM, about 1.3 μM, about 1.4 μM, about 1.5 μM, about 1.6 μM, about 1.7 μM, about 1.8 μM, about 1.9 μM, about 2 μM, about 2.1 μM, about 2.2 μM, about 2.3 μM, about 2.4 μM, about 2.5 μM, about 2.6 μM, about 2.7 μM, about 2.8 μM, about 2.9 μM, about 3 μM, about 3.1 μM, about 3.2 μM, about 3.3 μM, about 3.4 μM, about 3.5 μM, about 3.6 μM, about 3.7 μM, about 3.8 μM, about 3.9 μM, about 4 μM, about 4.1 μM, about 4.2 μM, about 4.3 μM, about 4.4 μM, about 4.5 μM, about 4.6 μM, about 4.7 μM, about 4.8 μM, about 4.9 μM, about 5 μM, about 5.1 μM, about 5.2 μM, about 5.3 μM, about 5.4 μM, about 5.5 μM, about 5.6 μM, about 5.7 μM, about 5.8 μM, about 5.9 μM, about 6 μM, about 6.1 μM, about 6.2 μM, about 6.3 μM, about 6.4 μM, about 6.5 μM, about 6.6 μM, about 6.7 μM, about 6.8 μM, about 6.9 μM, about 7 μM, about 7.1 μM, about 7.2 μM, about 7.3 μM, about 7.4 μM, about 7.5 μM, about 7.6 μM, about 7.7 μM, about 7.8 μM, about 7.9 μM, about 8 μM, about 8.1 μM, about 8.2 μM, about 8.3 μM, about 8.4 μM, about 8.5 μM, about 8.6 μM, about 8.7 μM, about 8.8 μM, about 8.9 μM, about 9 μM, about 9.1 μM, about 9.2 μM, about 9.3 μM, about 9.4 μM, about 9.5 μM, about 9.6 μM, about 9.7 μM, about 9.8 μM, about 9.9 μM, about 10 μM, about 10.5 μM, about 11 μM, about 11.5 μM, about 12 μM, about 12.5 μM, about 13 μM, about 13.5 μM, about 14 μM, about 14.5 μM, about 15 μM, about 15.5 μM, about 16 μM, about 16.5 μM, about 17 μM, about 17.5 μM, about 18 μM, about 18.5 μM, about 19 μM, about 19.5 μM, about 20 μM, 1.0 μg/mL, 1.1 μg/mL, 1.2 μg/mL, 1.3 μg/mL, 1.4 μg/mL, 1.5 μg/mL, 1.6 μg/mL, 1.7 μg/mL, 1.8 μg/mL, 1.9 μg/mL, 2.0 μg/mL, 2.1 μg/mL, 2.2 μg/mL, 2.3 μg/mL, 2.4 μg/mL, 2.5 μg/mL, 2.6 μg/mL, 2.7 μg/mL, 2.8 μg/mL, 2.9 μg/mL, 3.0 μg/mL, 3.1 μg/mL, 3.2 μg/mL, 3.3 μg/mL, 3.4 μg/mL, 3.5 μg/mL, 3.6 μg/mL, 3.7 μg/mL, 3.8 μg/mL, 3.9 μg/mL, 4.0 μg/mL, 4.1 μg/mL, 4.2 μg/mL, 4.3 μg/mL, 4.4 μg/mL, 4.5 μg/mL, 4.6 μg/mL, 4.7 μg/mL, 4.8 μg/mL, 4.9 μg/mL, 5.0 μg/mL, 5.1 μg/mL, 5.2 μg/mL, 5.3 μg/mL, 5.4 μg/mL, 5.5 μg/mL, 5.6 μg/mL, 5.7 μg/mL, 5.8 μg/mL, 5.9 μg/mL, 6.0 μg/mL, 6.5 μg/mL, 7.0 μg/mL, 7.5 μg/mL, 8.0 μg/mL, 8.5 μg/mL 9.0 μg/mL, 9.5 μg/mL, 10.0 μg/mL, 10.5 μg/mL, 11.0 μg/mL, 11.5 μg/mL, 12.0 μg/mL, 12.5 μg/mL, 13.0 μg/mL, 13.5 μg/mL, 14.0 μg/mL, 14.5 μg/mL, 15.0 μg/mL, 15.5 μg/mL, 16.0 μg/mL, 16.5 μg/mL, 17.0 μg/mL, 17.5 μg/mL, 18.0 μg/mL, 18.5 μg/mL, 19.0 μg/mL, 19.5 μg/mL, or 20.0 μg/mL. At the MIC, the stapled and/or stitched anti-microbial peptides has hemolytic activity against human red cells, as measured in the hemolytic assay described in the Methods herein, which can be 0-10%, 5-10%, 0-5%, about 0%, about 1%, about 2%, about 3%, about 4%, about 5%, about 6%, about 7%, about 8%, about 9%, about 10%, less than 10%, less than 9%, less than 8%, less than 7%, less than 6%, less than 5%, less than 4%, less than 3%, less than 2%, less than 1%, 0.1%, 0.2%, 0.3%, 0.4%, 0.5%, 0.6%, 0.7%, 0.8%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 15%, 20%, 25%, 30%, 35%, 40%, 45%, or 50%. As used herein, the terms "about" and "approximately" are defined as being within plus or minus 10% of a given value or state, preferably within plus or minus 5% of said value or state.

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, e.g., those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this disclosure can be made by chemical synthesis methods, which are well known to the ordinarily skilled artisan. See, e.g., Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH$_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation or convergent solid phase peptide synthesis. Alternatively, the longer synthetic peptides can be synthesized by well-known recombinant DNA techniques. Such techniques are provided in well-known standard manuals with detailed protocols. To construct a gene encoding a peptide of this disclosure, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH$_3$; and a fluoro-ketomethylene bond (C(O)—CFR or CFR—C(O) wherein R is H or F or CH$_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C$_1$-C$_{20}$ straight or branched alkyl groups); fatty acid radicals; and combinations thereof.

α, α-Disubstituted non-natural amino acids containing olefinic side chains of varying length can be synthesized by known methods (see, e.g., Williams et al. J. Am. Chem. Soc., 113:9276, 1991; Schafmeister et al., J. Am. Chem Soc., 122:5891, 2000; and Bird et al., Methods Enzymol., 446: 369, 2008; Bird et al, Current Protocols in Chemical Biology, 2011). For peptides where an i linked to 1+7 staple is used (two turns of the helix stabilized), either: a) one S$_5$ amino acid and one R$_8$ is used or b) one S$_8$ amino acid and one R$_5$ amino acid is used. R$_8$ is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-S$_5$—OH, Fmoc-R$_8$—OH, Fmoc-R$_8$—OH, Fmoc-S$_5$—OH and Fmoc-R$_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N, N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (see, e.g., Williams et al., Org. Synth., 80:31, 2003).

The compounds of this disclosure may be modified by appending appropriate functionalities to enhance selective biological properties (including, e.g., hydrophobicity and/or the position/occurrence of hydrophobic patches). Such modifications are known in the art and include those which increase biological penetration into a given biological compartment (e.g., blood, lymphatic system, central nervous system), increase oral availability, increase solubility to allow administration by injection, alter metabolism, and alter rate of excretion.

A stabilized AMP selective for microbial versus mammalian membranes (i.e., a peptide able to kill or inhibit the growth of a microbe (e.g., Gram-negative bacteria, an antibiotic-resistant Gram-negative bacteria) while also having a relatively low ability to lyse or inhibit the growth of a mammalian cell) may, e.g., possess a MIC for one or more microbes (e.g., Gram-negative bacteria, an antibiotic-resistant Gram-negative bacteria) more than about 1.5-fold lower, more than about 2-fold lower, more than about 2.5-fold lower, more than about 3-fold lower, more than about 4-fold lower, more than about 5-fold lower, more than about 6-fold lower, more than about 7-fold lower, more than about 8-fold lower, more than about 9-fold lower, more than about 10-fold lower, more than about 15-fold lower, or more than about 20-fold lower than the MIC of the corresponding parent (i.e., unmodified) non-internally cross-linked peptide for the same one or more microbes (e.g., Gram-negative bacteria, an antibiotic-resistant Gram-negative bacteria). An antimicrobial peptide selective for microbial versus mammalian membranes can have a MIC of, e.g., about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 12 µg/ml, about 14 µg/ml, about 16 µg/ml, about 18 µg/ml, about 20 µg/ml, about 22 µg/ml, about 24 µg/ml, about 26 µg/ml, about 28 µg/ml, or about 30 µg/ml. An antimicrobial peptide selective for microbial versus mammalian membranes may lyse, e.g., less than about 50%, less than about 40%, less than about 30%, less than about 25%, less than about 20%, less than about 15%, less than about 10%, less than about 5%, less than about 2.5%, less than about 2%, or less than about 1% of red blood cells (RBCs) in a RBC hemolytic activity assay when administered at a concentration, e.g., greater than or approximately equal to 1-fold, 1.5-fold, 2-fold, 2.5-fold, 3-fold, 4-fold, 5-fold, 6-fold, 7-fold, 8-fold, 9-fold, or 10-fold its MIC for one or more microbes (e.g., Gram-negative bacteria, an antibiotic-resistant Gram-negative bacteria).

Methods of Optimizing a Stapled and/or Stitched Antimicrobial Peptide that Overcomes Gram-Negative Colistin-Resistance Provided herein are methods of optimizing a stapled and/or stitched antimicrobial peptide (StAMP) that include: providing a first stapled and/or stitched antimicrobial peptide (StAMP), generating a second StAMP that is identical to the first StAMP except at one or more amino acid positions (e.g., 1, 2, 3, 4, 5, 6, 7, 8, 9, or 10 amino acid positions); determining that the second StAMP kills or inhibits growth of Gram-negative colistin-resistant bacteria to a greater level that the first StAMP.

In some embodiments, the methods can further include determining that the second StAMP has the same or decreased hemolytic activity relative to the first StAMP. In some embodiments, the first StAMP and the second StAMP are double-stapled. In some embodiments, the first StAMP comprises or consists of any one of SEQ ID Nos.: 1-3, 34, 35 or 36-43. In some embodiments, the first StAMP comprises or consists of SEQ ID Nos.: 1-35.

In some embodiments, the first and second StAMP are each 6 to 100 amino acids in length.

In some embodiments, the second StAMP is dihydroxylated as compared to the first StAMP, and the hydrophobicity of the second StAMP is reduced as compared to the first StAMP. In some embodiments, the Sharpless dihydroxylation reaction can be used to introduce two alcohol groups into the alkene group present in the antimicrobial peptide (see, e.g., US Patent Publication No. 2017/0015716, incorporated in its entirety herein).

In some embodiments, the second StAMP is aminohydroxylated as compared to the first StAMP, and the hydrophobicity of the second StAMP is reduced as compared to the first StAMP. In some embodiments, the Sharpless aminohydroxylation reaction can be used to modify the alkene group (see, e.g., US Patent Publication No. 2017/0015716, incorporated in its entirety herein).

In some embodiments, the StAMP (e.g., hydrocarbon-stapled and/or stitched peptide) is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin A, cathelicidin A, and dermicidin.

In certain embodiments, the hemolytic activity of the second StAMP is reduced compared to the first StAMP and the hemolytic activity of the second StAMP is less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, 0-4%, 0-2%, 0-1%, 1-4%, 1-3.5%, 1-3%, 1-2.5%, 1-2%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1% 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.95%, 0.9%, 0.8%, 0.7%, 0.6%, 0.5%, 0.4%, 0.3%, 0.25%, 0.2%, 0.1%, 0.095%, 0.09%, 0.085%, 0.08%, 0.075%, 0.07%, 0.065%, 0.06%, 0.055%, 0.05%, 0.045%, 0.04%, 0.035%, 0.03%, 0.025%, 0.02%, 0.015%, or 0.001%), and the minimum inhibitory concentration against a Gram-negative colistin-resistant bacterium is less than 10.0 μg/mL (e.g., less than 9.5 μg/mL, less than 9.0 μg/mL, less than 8.5 μg/mL, less than 8.0 μg/mL, less than 7.5 μg/mL, less than 7.0 μg/mL, less than 6.5 μg/mL, less than 6.0 μg/mL, less than 5.5 μg/mL, less than 5.0 μg/mL, less than 4.5 μg/mL, less than 4.0 μg/mL, less than 3.5 μg/mL, less than 3.0 μg/mL, less than 2.5 μg/mL, less than 2.0 μg/mL, less than 1.5 μg/mL, less than 1.0 μg/mL, or less than 0.5 μg/mL, 0.5-3.0 μg/mL, 0.5-2.5 μg/mL 0.5-2.0 μg/mL, 0.5-1.5 μg/mL, 0.5-1.0 μg/mL, 1.0-3.0 μg/mL, 1.0-2.5 μg/mL 1.0-2.0 μg/mL, 1.0-1.5 μg/mL, 1.5-3.0 μg/mL, 1.5-2.5 μg/mL 1.5-2.0 μg/mL, 2.0-3.0 μg/mL, 2.0-2.5 μg/mL, 2.5-3.0 μg/mL, 0.1 μg/mL, 0.2 μg/mL, 0.3 μg/mL, 0.4 μg/mL, 0.5 μg/mL, 0.6 μg/mL, 0.7 μg/mL, 0.8 μg/mL, 0.9 μg/mL, 1.0 μg/mL, 1.1 μg/mL, 1.2 μg/mL, 1.3 μg/mL, 1.4 μg/mL, 1.5 μg/mL, 1.6 μg/mL, 1.7 μg/mL, 1.8 μg/mL, 1.9 μg/mL, 2.0 μg/mL, 2.1 μg/mL, 2.2 μg/mL, 2.3 μg/mL, 2.4 μg/mL, 2.6 μg/mL, 2.7 μg/mL, 2.8 μg/mL, 2.9 μg/mL, 3.0 μg/mL, 3.5 μg/mL, 4.0 μg/mL, 5.0 μg/mL, 5.5 μg/mL, 6.0 μg/mL, 6.5 μg/mL, 7.0 μg/mL, 7.5 μg/mL, 8.0 μg/mL, 8.5 μg/mL, 9.0 μg/mL, 9.5 μg/mL).

In some embodiments, the Gram-negative colistin-resistant antimicrobial activity is against *A. baumannii*. In some embodiments, the Gram-negative colistin-resistant antimicrobial activity is against *E. coli*. In some embodiments, the Gram-negative colistin-resistant antimicrobial activity is against a Gram-negative colistin-resistant bacterium that contains a MCR-1 plasmid. In some embodiments, the Gram-negative colistin-resistant antimicrobial activity is against an *E. coli* strain that contains a MCR-1 plasmid. In some embodiments, the Gram-negative colistin-resistant antimicrobial activity is against a *Klebsiella pneumoniae* strain that contains a MCR-1 plasmid.

These methods are based on the modifications of specific amino acid residues of a first stapled and/or stitched antimicrobial peptide that may serve as a control and/or reference stapled and/or stitched antimicrobial peptide. Specific amino acid residues of a first stapled and/or stitched antimicrobial peptide can be modified by various methods, e.g., site-direct mutagenesis or by making a point mutant library. In some embodiments, the at least one point-mutation is a non-synonymous substitution (i.e., at least one point-mutation that results in a codon that encodes for a different amino acid). The at least one point-mutation can result in an amino acid being replaced with any other amino acid residue known in the art, including, e.g., an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In some embodiments, the at least one point-mutation results in an amino acid substitution that does not have a similar side chain as the amino acid at that position in the first stapled and/or stitched peptide.

In some instances, one or more (e.g., 1, 2, 3, 4, or 5) amino acid is replaced by a non-hydrophobic amino acid. In some instances, any of the StAMPs disclosed herein include an internal staple replacing the side chains of two amino acids separated by two, three, or six amino acids comprises an internal staple. In some instances, the internal staples and/or the internal stitch replacing the side chains of the three amino acids includes an internal stitch. In some instances, the internal staples and/or the internal stitch comprises at least two internal staples (replacing the side chains of 4 amino acids, i.e., each staple is between two amino acids separated by 3 amino acids). In some instances, the internal staples and/or the internal stitch comprises a combination of at least one internal staple and an internal stitch. In some instances, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some aspects, the internal stitch replacing the side chains of the three amino acids cross-links a pair of amino acids separated by two, three, or six amino acids. In some aspects, the side chains of the four amino acids of the internally cross-linked polypeptides of the disclosure are replaced by two distinct internal staples. In some aspects, a first of the two distinct internal staples cross-links a first pair of amino acids separated by two, three, or six amino acids, and a second of the at least two distinct internal staples cross-links a second pair of amino acids separated by two, three, or six amino acids.

In some instances, the stapled and/or stitched antimicrobial peptide (StAMP) is a modified peptide that includes 1, 2, 3, 4, or 5 amino acid substitutions (e.g., 1, 2, 3, 4, or 5 amino acids are replaced with A or 1, 2, 3, 4, or 5 amino acids are conservatively substituted).

In some instances, stapled and/or stitched antimicrobial peptide (StAMP) can have at least 80% (e.g., 80%, 85%, 90%, 95%, 98%, 99%, 99.5%, or 100%) identity one of SEQ ID Nos.: 1-43 or can include one of SEQ ID Nos.: 1-43 with one or more (e.g., 1, 2, 3, 4, 5, 6, 7, 8, 9, 10, 11, 12, 13, 14, 15, 16, 17, 18, e.g., 1-2, 1-3, 1-4, or 1-5) conservative amino acid substitutions. In some cases, the stapled and/or stitched antimicrobial peptide (StAMP) has the sequence of one SEQ ID Nos.: 1-43 with one or two staples (e.g., one staple between two amino acids separated by 2 or 3 (or 6) amino acids or two staples each between two amino acids that are separated by 2 or 3 (or 6) amino acids).

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes can be at least 30%, at least 40%, at least 50%, at least 60%, and at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences can be accomplished using, e.g., the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described, e.g., in Altschul et al. (*Nucleic Acids Res.* 25:3389-3402, 1997).

This document also features a method of designing an antimicrobial peptide or stapled antimicrobial peptide (StAMP) that has improved microbial activity and/or reduced hemolytic activity relative to the unmodified antimicrobial peptide or stapled antimicrobial peptide. The method involves one or more of: (i) increasing the net positive charge of the antimicrobial peptide or stapled antimicrobial peptide (e.g., by increasing the number of basic residues, such as lysine, in the peptide, e.g., by amino acid substitution); (ii) increasing the number of histidine residues, e.g., by amino acid substitution; and/or (iii) reducing the rigid helicity of an AMP or StAMP (e.g., substituting an amino acid with D-alanine). In certain instances, the AMP or StAMP has at least one (e.g., 1, 2, 3, 4, 5) histidines and/or lysines relative to the unmodified antimicrobial peptide. The methods of optimizing a StAMP that overcomes antibiotic-resistance of a Gram-negative bacterium described above can be modified and applied to optimize a StAMP that overcomes antibiotic-resistance of a Gram-positive bacterium.

Methods of Selecting a Stapled and/or Stitched Antimicrobial Peptide (StAMP) that Overcomes Colistin-Resistance of a Gram-Negative Bacterium Provided herein are methods of selecting a stapled and/or stitched antimicrobial peptide that overcomes colistin-resistance of a Gram-negative bacterium that includes: providing a StAMP, determining the hemolytic activity and the minimum inhibitory concentration (MIC) of the StAMP for a Gram-negative bacterium; and selecting the StAMP when the StAMP has a minimum inhibitory concentration against the colistin-resistant Gram-negative bacterium of less than 10.0 μg/mL (e.g., less than 9.5 μg/mL, less than 9.0 μg/mL, less than 8.5 μg/mL, less than 8.0 μg/mL, less than 7.5 μg/mL, less than 7.0 μg/mL, less than 6.5 μg/mL, less than 6.0 μg/mL, less than 5.5 μg/mL, less than 5.0 μg/mL, less than 4.5 μg/mL, less than 4.0 μg/mL, less than 3.5 μg/mL, less than 3.0 μg/mL, less than 2.5 μg/mL, less than 2.0 μg/mL, less than 1.5 μg/mL, less than 1.0 μg/mL, or less than 0.5 μg/mL, 0.5-3.0 μg/mL, 0.5-2.5 μg/mL 0.5-2.0 μg/mL, 0.5-1.5 μg/mL, 0.5-1.0 μg/mL, 1.0-3.0 μg/mL, 1.0-2.5 μg/mL 1.0-2.0 μg/mL, 1.0-1.5 μg/mL, 1.5-3.0 μg/mL, 1.5-2.5 μg/mL 1.5-2.0 μg/mL, 2.0-3.0 μg/mL, 2.0-2.5 μg/mL, 2.5-3.0 μg/mL, 0.1 μg/mL, 0.2 μg/mL, 0.3 μg/mL, 0.4 μg/mL, 0.5 μg/mL, 0.6 μg/mL, 0.7 μg/mL, 0.8 μg/mL, 0.9 μg/mL, 1.0 μg/mL, 1.1 μg/mL, 1.2 μg/mL, 1.3 μg/mL, 1.4 μg/mL, 1.5 μg/mL, 1.6 μg/mL, 1.7 μg/mL, 1.8 μg/mL, 1.9 μg/mL, 2.0 μg/mL, 2.1 μg/mL, 2.2 μg/mL, 2.3 μg/mL, 2.4 μg/mL, 2.6 μg/mL, 2.7 μg/mL, 2.8 μg/mL, 2.9 μg/mL, 3.0 μg/mL, 3.5 μg/mL, 4.0 μg/mL, 5.0 μg/mL, 5.5 μg/mL, 6.0 μg/mL, 6.5 μg/mL, 7.0 μg/mL, 7.5 μg/mL, 8.0 μg/mL, 8.5 μg/mL, 9.0 μg/mL, 9.5 μg/mL); and a hemolytic activity of less than 5.0% (e.g., less than 4%, less than 3%, less than 2%, less than 1%, less than 0.5%, 0-4%, 0-2%, 0-1%, 1-4%, 1-30.5%, 1-3%, 1-20.5%, 1-2%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1% 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.95%, 0.9%, 0.8%, 0.7%, 0.6%, 0.5%, 0.4%, 0.3%, 0.25%, 0.2%, 0.1%, 0.095%, 0.09%, 0.085%, 0.08%, 0.075%, 0.07%, 0.065%, 0.06%, 0.055%, 0.05%, 0.045%, 0.04%, 0.035%, 0.03%, 0.025%, 0.02%, 0.015%, or 0.001%).

In some embodiments, the stapled and/or stitched antimicrobial peptide (StAMP) is selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

In some embodiments, the methods further include providing a StAMP from a StAMP library. In some embodiments, the StAMP library is a library of a StAMP selected from the group consisting of: magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin. In some embodiments, the StAMP library is a staple walk library.

The methods of selecting a StAMP that overcomes antibiotic-resistance of a Gram-negative bacterium described above can be modified and applied in methods of selecting a StAMP that overcomes antibiotic-resistance of a Gram-positive bacterium.

Methods of Screening for a StAMP that Kills and/or Inhibits Growth of a Colistin-Resistant Gram-Negative Bacterium Provided herein are methods of screening for a stapled and/or stitched antimicrobial peptide (StAMP) that kills and/or inhibits the growth of a colistin-resistant Gram-negative bacterium that includes: providing a StAMP, contacting the StAMP with a colistin-resistant Gram-negative bacterium; determining that the StAMP kills and/or inhibits the growth of the colistin-resistant Gram-negative bacterium with a MIC of less than 10.0 µg/mL (e.g., less than 9.5 µg/mL, less than 9.0 µg/mL, less than 8.5 µg/mL, less than 8.0 µg/mL, less than 7.5 µg/mL, less than 7.0 µg/mL, less than 6.5 µg/mL, less than 6.0 µg/mL, less than 5.5 µg/mL, less than 5.0 µg/mL, less than 4.5 µg/mL, less than 4.0 µg/mL, less than 3.5 µg/mL, less than 3.0 µg/mL, less than 2.5 µg/mL, less than 2.0 µg/mL, less than 1.5 µg/mL, less than 1.0 µg/mL, or less than 0.5 µg/mL, 0.5-3.0 µg/mL, 0.5-2.5 µg/mL 0.5-2.0 µg/mL, 0.5-1.5 µg/mL, 0.5-1.0 µg/mL, 1.0-3.0 µg/mL, 1.0-2.5 µg/mL 1.0-2.0 µg/mL, 1.0-1.5 µg/mL, 1.5-3.0 µg/mL, 1.5-2.5 µg/mL 1.5-2.0 µg/mL, 2.0-3.0 µg/mL, 2.0-2.5 µg/mL, 2.5-3.0 µg/mL, 0.1 µg/mL, 0.2 µg/mL, 0.3 µg/mL, 0.4 µg/mL, 0.5 µg/mL, 0.6 µg/mL, 0.7 µg/mL, 0.8 µg/mL, 0.9 µg/mL, 1.0 µg/mL, 1.1 µg/mL, 1.2 µg/mL, 1.3 µg/mL, 1.4 µg/mL, 1.5 µg/mL, 1.6 µg/mL, 1.7 µg/mL, 1.8 µg/mL, 1.9 µg/mL, 2.0 µg/mL, 2.1 µg/mL, 2.2 µg/mL, 2.3 µg/mL, 2.4 µg/mL, 2.6 µg/mL, 2.7 µg/mL, 2.8 µg/mL, 2.9 µg/mL, 3.0 µg/mL, 3.5 µg/mL, 4.0 µg/mL, 5.0 µg/mL, 5.5 µg/mL, 6.0 µg/mL, 6.5 µg/mL, 7.0 µg/mL, 7.5 µg/mL, 8.0 µg/mL, 8.5 µg/mL, 9.0 µg/mL, 9.5 µg/mL).

In some embodiments, the method can further include determining that the StAMP has a hemolytic activity of less than 5.0% (e.g., less than 4%, less than 3%, less than 2%, less than 1%, less than 0.5%, 0-4%, 0-2%, 0-1%, 1-4%, 1-3.5%, 1-3%, 1-2.5%, 1-2%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1% 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.95%, 0.9%, 0.8%, 0.7%, 0.6%, 0.5%, 0.4%, 0.3%, 0.25%, 0.2%, 0.1%, 0.095%, 0.09%, 0.085%, 0.08%, 0.075%, 0.07%, 0.065%, 0.06%, 0.055%, 0.05%, 0.045%, 0.04%, 0.035%, 0.03%, 0.025%, 0.02%, 0.015%, or 0.001%).

In some embodiments, the stapled and/or stitched antimicrobial peptide (StAMP) is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

The methods of screening for a StAMP that kills and/or inhibits growth of an antibiotic-resistant Gram-negative bacterium described can be modified and applied for screening for a StAMP that kills and/or inhibits growth of an antibiotic-resistant Gram-positive bacterium.

Methods of Treating an Antibiotic-resistant Bacterial Infection

Provided herein are methods of treating an antibiotic-resistant Gram-negative or Gram-positive bacterial infection. The methods involve administering a therapeutically effective amount of a StAMP (e.g., a hydrocarbon-stapled and/or stitched peptide) described herein to the subject that has, or is at risk of developing, the antibiotic-resistant Gram-negative or Gram-positive bacterial infection.

In one instance, the disclosure provides methods of treating a Gram-negative colistin-resistant bacterial infection in a subject in need thereof that include administering a therapeutically effective amount of a StAMP (e.g., a hydrocarbon-stapled and/or stitched peptide) described herein to the subject that has, or is at risk of developing, the Gram-negative colistin-resistant bacterial infection. In some embodiments, the subject has, or is at risk of developing a Gram-negative bacterial infection selected from the group consisting of: gastritis, gastric cancer, gall bladder carcinoma, pneumonia, or urinary tract infection. In some embodiments, the subject has, or is at risk of developing a Gram-negative bacterial infection that primarily affects the gastro-intestinal system. In some embodiments, the subject has, or is at risk of developing a Gram-negative bacterial infection that primarily affects the respiratory system.

In another instance, the disclosure provides methods of treating an antibiotic-resistant Gram-positive bacterial infection in a subject in need thereof that include administering a therapeutically effective amount of a StAMP (e.g., a hydrocarbon-stapled and/or stitched peptide) described herein to the subject that has, or is at risk of developing, the antibiotic-resistant Gram-positive bacterial infection. In some cases, the Gram-positive bacterium is *S. aureus*. In some cases, the Gram-positive bacterium is resistant to methicillin. In some cases, the Gram-positive bacterium is resistant to penicillin. In some cases, the Gram-positive bacterium is resistant to vancomycin. In some cases, the Gram-positive bacterium is resistant to an aminoglycoside. In some cases, the Gram-positive bacterium is one of: *Actinomyces israelii, Actinomyces gerencseriae, Propionibacterium propionicus, Bacillus anthracis, Arcanobacterium haemolyticum, Bacillus cereus*, bacterial vaginosis microbiota, *Clostridium botulinum, Mycobacterium ulcerans*, Group A *Streptococcus* and *Staphylococcus, Clostridium difficile, Corynebacterium diphtheria, Enterococcus species, Clostridium perfringens*, other *Clostridium* species, *Streptococcus pyogenes, Streptococcus agalactiae, Mycobacterium leprae, Mycobacterium lepromatosis, Listeria monocytogenes, Nocardia asteroides, Nocardia species, Streptococcus pneumoniae, Staphylococcus aureus, Staphylococcus species, Clostridium tetani, Mycobacterium tuberculosis, Yersinia pseudotuberculosis*, or *Yersinia enterocolitica*.

In certain embodiments, the subject has developed an infection with antibiotic-resistance to at least one (e.g., 1, 2, 3, 4, 5, 6, 7, 8, 9, or 10) other class of antibiotic. In some embodiments, the at least one (e.g., 1, 2, 3, 4, 5, 6, 7, 8, 9, or 10) other class of antibiotic is selected from the group consisting of: carbapenem, an aminoglycoside, vancomycin, methicillin, clarithromycin, cephalosporin, penicillin, ampicillin, fluoroquinolone, tetracycline, and a β-lactam. In certain embodiments, the at least one other class of antibiotic is carbapenem. In certain embodiments, the at least one other class of antibiotic is clarithromycin. In certain embodiments, the at least one other class of antibiotic is cephalosporin. In certain embodiments, the at least one other class of antibiotic is fluoroquinolone. In certain embodiments, the at least one other class of antibiotic is methicillin. In certain embodiments, the at least one other class of antibiotic is vancomycin. In certain embodiments, the at least one other class of antibiotic is methicillin and vancomycin. In certain embodiments, the at least one other class of antibiotic is cephalosporin and fluoroquinolone.

In certain embodiments, the at least one other class of antibiotic is carbapenem and at least one (e.g., 1, 2, 3, 4, 5, 6, 7, 8, 9) other class of antibiotics selected from the group consisting of: an aminoglycoside, vancomycin, methicillin, clarithromycin, cephalosporin, penicillin, ampicillin, fluoroquinolone, tetracycline, and a β-lactam. In certain embodiments, the at least one other class of antibiotic is an aminoglycoside and at least one other class (e.g., 1, 2, 3, 4, 5, 6, 7, 8, 9) of antibiotics selected from the group consisting of: carbapenem, vancomycin, methicillin, clarithromycin, cephalosporin, penicillin, ampicillin, fluoroquinolone, tetracycline, and a β-lactam. In certain embodiments, the at least one other class of antibiotic is vancomycin and at least one (e.g., 1, 2, 3, 4, 5, 6, 7, 8, 9) other class of antibiotics selected from the group consisting of: carbapenem, an aminoglycoside, methicillin, clarithromycin, cephalosporin, penicillin, ampicillin, fluoroquinolone, tetracycline, and a β-lactam. In certain embodiments, the at least one other class of antibiotic is methicillin and at least one (e.g., 1, 2, 3, 4, 5, 6, 7, 8, 9) other class of antibiotics selected from the group consisting of: carbapenem, an aminoglycoside, vancomycin, clarithromycin, cephalosporin, penicillin, ampicillin, fluoroquinolone, tetracycline, and a β-lactam. In certain embodiments, the at least one other class of antibiotic is clarithromycin and at least one (e.g., 1, 2, 3, 4, 5, 6, 7, 8, 9) other class of antibiotics selected from the group consisting of: carbapenem, an aminoglycoside, vancomycin, methicillin, cephalosporin, penicillin, ampicillin, fluoroquinolone, tetracycline, and a β-lactam. In certain embodiments, the at least one other class of antibiotic is cephalosporin and at least one (e.g., 1, 2, 3, 4, 5, 6, 7, 8, 9) other class of antibiotics selected from the group consisting of: carbapenem, an aminoglycoside, vancomycin, methicillin, clarithromycin, penicillin, ampicillin, fluoroquinolone, tetracycline, and a β-lactam. In certain embodiments, the at least one other class of antibiotic is penicillin and at least one (e.g., 1, 2, 3, 4, 5, 6, 7, 8, 9) other class of antibiotics selected from the group consisting of: carbapenem, an aminoglycoside, vancomycin, methicillin, clarithromycin, cephalosporin, ampicillin, fluoroquinolone, tetracycline, and a β-lactam.

In certain embodiments, the at least one other class of antibiotic is ampicillin and at least one (e.g., 1, 2, 3, 4, 5, 6, 7, 8, 9) other class of antibiotics selected from the group consisting of: carbapenem, an aminoglycoside, vancomycin, methicillin, clarithromycin, cephalosporin, penicillin, fluoroquinolone, tetracycline, and a β-lactam. In certain embodiments, the at least one other class of antibiotic is fluoroquinolone and at least one (e.g., 1, 2, 3, 4, 5, 6, 7, 8, 9) other class of antibiotics selected from the group consisting of: carbapenem, an aminoglycoside, vancomycin, methicillin, clarithromycin, cephalosporin, penicillin, ampicillin, tetracycline, and a β-lactam. In certain embodiments, the at least one other class of antibiotic is tetracycline and at least one (e.g., 1, 2, 3, 4, 5, 6, 7, 8, 9) other class of antibiotics selected from the group consisting of: carbapenem, an aminoglycoside, vancomycin, methicillin, clarithromycin, cephalosporin, penicillin, ampicillin, fluoroquinolone, and a β-lactam. In certain embodiments, the at least one other class of antibiotic is β-lactam and at least one (e.g., 1, 2, 3, 4, 5, 6, 7, 8, 9) other class of antibiotics selected from the group consisting of: carbapenem, an aminoglycoside, vancomycin, methicillin, clarithromycin, cephalosporin, penicillin, ampicillin, fluoroquinolone, and tetracycline.

In certain embodiments, the subject has a chronic Gram-negative colistin-resistant bacterial infection. In some embodiments, the Gram-negative colistin-resistant bacterial infection is an *A. baumannii* infection. In some embodiments, the Gram-negative colistin-resistant bacterial infection is an *E. coli* infection. In some embodiments, the Gram-negative colistin-resistant bacterial infection is a *Klebsiella pneumonia* infection. In some embodiments, the Gram-negative colistin-resistant bacterial infection is an infection selected from the group consisting of a *Pseudomonas* infection, a *Neisseria* infection, a *Chlamydia* infection, a *Yersinia* infection, a *Proteus* infection, an *Enterobacter* infection, a *Serratia* infection, a *Helicobacter* infection, a *Salmonella* infection, a *Shigella* infection, a *Moraxella* infection, a *Stenotrophomonas* infection, a *Bdellovibrio* infection, an acetic acid bacterial infection, a *Klebsiella* infection, and a *Legionella* infection. In some embodiments, the Gram-negative colistin-resistant bacterial infection is an infection selected from the group consisting of a *Pseudomonas aeruginosa* infection, a *Neisseria gonorrhoeae* infection, a *Chlamydia trachomatis* infection, a *Yersinia pestis* infection, a *Proteus mirabilis* infection, an *Enterobacter cloacae* infection, a *Serratia marcescens* infection, a *Helicobacter pylori* infection, a *Salmonella enteritidis* infection, a *Salmonella typhi* infection, a *Klebsiella pneumoniae* infection, and a *Legionella pneumophila* infection.

In some embodiments, the Gram-negative colistin-resistant bacterial infection is from a Gram-negative bacterium that contains a MCR-1 plasmid. In some embodiments, the Gram-negative bacterium that contains a MCR-1 plasmid is *E. coli, Salmonella enteric, Klebsiella pneumonia, Pseudomonas aeruginosa, Enterobacter aerogenes*, or *E. cloacae*. In one embodiment, the Gram-negative bacterium that contains a MCR-1 plasmid is *E. coli*. In another embodiment, the Gram-negative bacterium that contains a MCR-1 plasmid is *Klebsiella pneumonia*.

In certain embodiments, the subject has a chronic antibiotic-resistant Gram-positive bacterial infection. In certain embodiments, the subject has a chronic Gram-positive methicillin-resistant bacterial infection. In some embodiments, the Gram-positive methicillin-resistant bacterial infection is a *S. aureus* infection.

In some embodiments, the stapled and/or stitched antimicrobial peptide (StAMP) is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

In some embodiments, the StAMP comprises or consists of the amino acid sequence set forth in any one of SEQ ID Nos.: 1-35, except for 1 to 5 amino acid substitutions, insertions, and/or deletions within SEQ ID Nos.: 1-35. In some embodiments, the StAMP comprises or consists of the amino acid sequence set forth in SEQ ID NO: 1-35. In some embodiments, the StAMP comprises or consists of the amino acid sequence set forth in any one of SEQ ID Nos.: 1-3, 34, or 35, except for 1 to 5 amino acid substitutions, insertions, and/or deletions within SEQ ID Nos.: 1-3, 34, or 35. In some embodiments, the StAMP comprises or consists of the amino acid sequence set forth in any one of SEQ ID Nos.: 1-3, 34, or 35. In some embodiments, the StAMP comprises or consists of the sequence of any one of SEQ ID Nos.: 7, 9, 11, 13, 15, 17, 19, 21, 23, 25, 27, 29, 31, 33, 34, or 35. In some embodiments of any of the methods described herein, the StAMP is double-stapled.

In some embodiments of any of the methods described herein, the StAMP is 6 to 100 amino acids in length (e.g., between 6 and 40 amino acids in length (e.g., between 6 and 10 amino acids in length, between 6 and 15 amino acids in length, between 6 and 20 amino acids in length, between 6 and 25 amino acids in length, between 6 and 30 amino acids in length, between 6 and 35 amino acids in length; between 10 and 15 amino acids in length, between 10 and 20 amino acids in length, between 10 and 25 amino acids in length, between 10 and 30 amino acids in length, between 10 and 35 amino acids in length; between 15 and 20 amino acids in length, between 15 and 25 amino acids in length, between 15 and 30 amino acids in length, between 15 and 35 amino acids in length; between 15 and 40 amino acids in length; between 20 and 25 amino acids in length, between 20 and 30 amino acids in length, between 20 and 35 amino acids in length; between 20 and 40 amino acids in length; between 30 and 35 amino acids in length; between 30 and 40 amino acids in length; or between 35 and 40 amino acids in length).

In some embodiments of any of the methods described herein, when the StAMP is to be administered intravenously to a subject, the StAMP preferably has a hemolytic activity that is less than 50% (e.g., less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, between 0-20%, 0-18%, 0-16%, 0-14%, 0-12%, 0-10%, 0-8%, 0-6%, 0-4%, 0-2%, 0-1%, 1-20%, 1-18%, 1-16%, 1-14%, 1-12%, 1-10%, 1-8%, 1-6%, 1-4%, 1-2%, 1.5-20%, 1-5-18%, 1.5-16%, 1.5-14%, 1.5-12%, 1.5-10%, 1.5-8%, 1.5-6%, 1.5-4%, 1.5-2%, 2-20%, 2-18%, 2-16%, 2-14%, 2-12%, 2-10%, 2-8%, 2-6%, 2-4%, 2.5-20%, 2.5-18%, 2.5-16%, 2.5-14%, 2.5-12%, 2.5-10%, 2.5-8%, 2.5-6%, 2.5-4%, 3-20%, 3-18%, 3-16%, 3-14%, 3-12%, 3-10%, 3-8%, 3-6%, 3-4%, 3.5-20%, 3.5-18%, 3.5-16%, 3.5-14%, 3.5-12%, 3.5-10%, 3.5-8%, 3.5-6%, 3.5-4%, 4-20%, 4-18%, 4-16%, 4-14%, 4-12%, 4-10%, 4-8%, 4-6%, 4.5-20%, 4.5-18%, 4.5-16%, 4.5-14%, 4.5-12%, 4.5-10%, 4.5-8%, 4.5-6%, 5-20%, 5-18%, 5-16%, 5-14%, 5-12%, 5-10%, 5-8%, 5-6%, 5.5-20%, 5.5-18%, 5.5-16%, 5.5-14%, 5.5-12%, 5.5-10%, 5.5-8%, 5.5-6%, 6-20%, 6-18%, 6-16%, 6-14%, 6-12%, 6-10%, 36-8%, 6.5-20%, 6.5-18%, 6.5-16%, 6.5-14%, 6.5-12%, 6.5-10%, 6.5-8%, 7-20%, 7-18%, 7-16%, 7-14%, 7-12%, 7-10%, 7-8%, 7.5-20%, 7.5-18%, 7.5-16%, 7.5-14%, 7.5-12%, 7.5-10%, 7.5-8%, 8-20%, 8-18%, 8-16%, 8-14%, 8-12%, 8-10%, 8.5-20%, 8.5-18%, 8.5-16%, 8.5-14%, 8.5-12%, 8.5-10%, 9-20%, 9-18%, 9-16%, 9-14%, 9-12%, 9-10%, 9.5-20%, 9.5-18%, 9.5-16%, 9.5-14%, 9.5-12%, 9.5-10%, 10-20%, 10-18%, 10-16%, 10-14%, 10-12%, 10.5-20%, 10.5-18%, 10.5-16%, 10.5-14%, 10.5-12%, 12-20%, 12-18%, 12-16%, 12-14%, 12.5-20%, 12.5-18%, 12.5-16%, 12.5-14%, 13-20%, 13-18%, 13-16%, 13-14%, 13.5-20%, 13.5-18%, 13.5-16%, 13.5-14%, 14-20%, 14-18%, 14-16%, 14.5-20%, 14.5-18%, 14.5-16%, 15-20%, 15-18%, 15-16%, 15.5-20%, 15.5-18%, 15.5-16%, 16-20%, 16-18%, 16.5-20%, 16.5-18%, 17-20%, 17-18%, 17.5-20%, 17.5-18%, 18-20%, 18.5-20%, 19-20%, 19.5-20%, 20%, 19.9%, 19.8%, 19.7%, 19.6%, 19.5%, 19.4%, 19.3%, 19.20%, 19.1%, 19%, 18.9%, 18.8%, 18.7%, 18.6%, 18.5%, 18.4%, 18.3%, 18.2%, 18.1%, 18%, 17.9%, 17.8%, 17.7%, 17.6%, 17.5%, 17.4%, 17.3%, 17.2%, 17.1%, 170%, 16.9%, 16.8%, 16.7%, 16.6%, 16.5%, 16.4%, 16.3%, 16.2%, 16.1%, 16%, 15.9%, 15.8%, 15.7%, 15.6%, 15.5%, 15.4%, 15.3%, 15.2%, 15.10%, 15%, 14.9%, 14.80%, 14.7%, 14.6%, 14.5%, 14.4%, 14.3%, 14.2%, 14.1%, 14%, 13.9%, 13.8%, 13.70%, 13.6%, 13.5%, 13.4%, 13.3%, 13.2%, 13.1%, 13%, 12.9%, 12.8%, 12.7%, 12.60%, 12.5%, 12.4%, 12.3%, 12.2%, 12.1%, 12%, 11.9%, 11.8%, 11.7%, 11.6%, 11.5%, 11.4%, 11.3%, 11.2%, 11.1%, 11%, 10.9%, 10.8%, 10.7%, 10.6%, 10.5%, 10.40%, 10.3%, 10.2%, 10.1%, 10%, 9.9%, 9.8%, 9.7%, 9.6%, 9.5%, 9.4%, 9.3%, 9.2%, 9.1%, 9%, 8.9%, 8.8%, 8.7%, 8.6%, 8.5%, 8.4%, 8.3%, 8.2%, 8.1%, 8%, 7.9%, 7.8%, 7.7%, 7.6%, 7.5%, 7.4%, 7.30%, 7.2%, 7.1%, 7%, 6.9%, 6.8%, 6.7%, 6.6%, 6.5%, 6.4%, 6.3%, 6.2%, 6.1%, 6%, 5.9%, 5.8%, 5.7%, 5.6%, 5.5%, 5.4%, 5.3%, 5.2%, 5.1%, 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.95%, 0.9%, 0.8%, 0.7%, 0.6%, 0.5%, 0.4%, 0.3%, 0.25%, 0.2%, 0.1%, 0.095%, 0.09%, 0.085%, 0.08%, 0.075%, 0.07%, 0.065%, 0.06%, 0.055%, 0.05%, 0.045%, 0.04%, 0.035%, 0.03%, 0.025%, 0.02%, 0.015%, or 0.001%).

In some embodiments of any of the methods described herein, when the StAMP is to be administered via a non-intravenous route to a subject, the StAMP can have any hemolytic activity. In certain embodiments, the StAMP has a hemolytic activity that is greater than 20% (e.g., less than 95%, less than 90%, less than 85%, less than 80%, less than 75%, less than 70%, less than 65%, less than 60%, less than 55%, less than 50%, less than 45%, less than 40%, less than 35%, less than 30%, less than 25%). In other embodiments, when the StAMP is to be administered via a non-intravenous route to a subject, the StAMP has a hemolytic activity that is less than 20% (e.g., less than 15%, less than 10%, less than 5%).

In some embodiments of any of the methods described herein, the StAMP has a minimum inhibitory concentration (MIC) for a colistin-resistant Gram-negative bacterium (e.g., *A. baumannii, E. coli, Klebsiella pneumoniae*) of less than 10.0 μg/mL (e.g., less than 9.5 μg/mL, less than 9.0 μg/mL, less than 8.5 μg/mL, less than 8.0 μg/mL, less than 7.5 μg/mL, less than 7.0 μg/mL, less than 6.5 μg/mL, less than 6.0 μg/mL, less than 5.5 μg/mL, less than 5.0 μg/mL, less than 4.5 μg/mL, less than 4.0 μg/mL, less than 3.5 μg/mL less than 3.0 μg/mL, less than 2.5 μg/mL, less than 2.0 μg/mL, less than 1.5 μg/mL, less than 1.0 μg/mL, less than 0.5 μg/mL, 0.5-8.0 μg/mL, 0.5-6.0 μg/mL, 0.5-4.0 μg/mL, 0.5-3.5 μg/mL, 0.5-2.0 μg/mL, 1-8.0 μg/mL, 1-6.0 μg/mL, 1-4.0 μg/mL, 1-2.0 μg/mL, 1.5-8.0 μg/mL, 1.5-6.0 μg/mL, 1.5-4.0 μg/mL, 1.5-2.0 μg/mL, 2-8.0 μg/mL, 2-6.0 μg/mL, 2-4.0 μg/mL, 2-8.0 μg/mL, 2-6.0 μg/mL, 2-4.0 μg/mL, 2.5-8.0 μg/mL, 2.5-6.0 μg/mL, 2.5-4.0 μg/mL, 2.5-8.0 μg/mL, 2.5-6.0 μg/mL, 2.5-4.0 μg/mL, 3-8.0 μg/mL, 3-6.0 μg/mL, 3-4.0 μg/mL, 3-8.0 μg/mL, 3-6.0 μg/mL, 3-4.0 μg/mL, 3-3.5 μg/mL, 3.5-4.0 μg/mL, 0.1 μg/mL, 0.2 μg/mL, 0.3 μg/mL, 0.4 μg/mL, 0.5 μg/mL, 0.6 μg/mL, 0.7 μg/mL, 0.8 µg/mL, 0.9 µg/mL, 1.0 µg/mL, 1.1 µg/mL, 1.2 µg/mL, 1.3 µg/mL, 1.4 µg/mL, 1.5 µg/mL, 1.6 µg/mL, 1.7 µg/mL, 1.8 µg/mL, 1.9 µg/mL, 2.0 µg/mL, 2.1 µg/mL, 2.2 µg/mL, 2.3 µg/mL, 2.4 µg/mL, 2.6 µg/mL, 2.7 µg/mL, 2.8 µg/mL, 2.9 µg/mL, 3.0 µg/mL, 3.1 µg/mL, 3.2 µg/mL, 3.3 µg/mL, 3.4 µg/mL, 3.5 µg/mL, 3.6 µg/mL, 3.7 µg/mL, 3.8 µg/mL, 3.9 µg/mL, 4.0 µg/mL, 4.1 µg/mL, 4.2 µg/mL, 4.3 µg/mL, 4.4 µg/mL, 4.5 µg/mL, 4.6 µg/mL, 4.7 µg/mL, 4.8 µg/mL, 4.9 µg/mL, 5.0 µg/mL, 5.2 µg/mL, 5.4 µg/mL, 5.6 µg/mL, 5.7 µg/mL, 5.8 µg/mL, 6.0 µg/mL, 6.2 µg/mL, 6.4 µg/mL, 6.6 µg/mL, 6.8 µg/mL, 7.0 µg/mL, 7.2 µg/mL, 7.4 µg/mL, 7.6 µg/mL, 7.8 µg/mL, 8.0 µg/mL, 8.1 µg/mL, 8.2 µg/mL, 8.3 µg/mL, 8.4 µg/mL, 8.5 µg/mL, 8.6 µg/mL, 8.7 µg/mL, 8.8 µg/mL, 8.9 µg/mL, 9.0 µg/mL, 9.1 µg/mL, 9.2 µg/mL, 9.3 µg/mL, 9.4 µg/mL, 9.5 µg/mL, 9.6 µg/mL, 9.7 µg/mL, 9.8 µg/mL, or 9.9 µg/mL).

In some embodiments of any of the methods described herein, the StAMP has a hemolytic activity of less than 10% (e.g., less than 9%, less than 8%, less than 7%, less than 6%, less than 5%, less than 4%, less than 3%, less than 2%, less than 1%, less than 0.5%, 0-4%, 0-2%, 0-1%, 1-4%, 1-3.5%, 1-3%, 1-2.5%, 1-2%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1% 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.95%, 0.9%, 0.8%, 0.7%, 0.6%, 0.5%, 0.4%, 0.3%, 0.25%, 0.2%, 0.1%, 0.095%, 0.09%, 0.085%, 0.08%, 0.075%, 0.07%, 0.065%, 0.06%, 0.055%, 0.05%, 0.045%, 0.04%, 0.035%, 0.03%, 0.025%, 0.02%, 0.015%, or 0.001%) and a minimum inhibitory concentration for a Gram-negative colistin-resistant bacterium of less than 3.0 µg/mL (e.g., less than 2.5 µg/mL, less than 2.0 µg/mL, less than 1.5 µg/mL, less than 1.0 µg/mL, less than 0.5 µg/mL, 0.5-3.0 µg/mL, 0.5-2.5 µg/mL 0.5-2.0 µg/mL, 0.5-1.5 µg/mL, 0.5-1.0 µg/mL, 1.0-3.0 µg/mL, 1.0-2.5 µg/mL 1.0-2.0 µg/mL, 1.0-1.5 µg/mL, 1.5-3.0 µg/mL, 1.5-2.5 µg/mL 1.5-2.0 µg/mL, 2.0-3.0 µg/mL, 2.0-2.5 µg/mL, 2.5-3.0 µg/mL, 0.1 µg/mL, 0.2 µg/mL, 0.3 µg/mL, 0.4 µg/mL, 0.5 µg/mL, 0.6 µg/mL, 0.7 µg/mL, 0.8 µg/mL, 0.9 µg/mL, 1.0 µg/mL, 1.1 µg/mL, 1.2 µg/mL, 1.3 µg/mL, 1.4 µg/mL, 1.5 µg/mL, 1.6 µg/mL, 1.7 µg/mL, 1.8 µg/mL, 1.9 µg/mL, 2.0 µg/mL, 2.1 µg/mL, 2.2 µg/mL, 2.3 µg/mL, 2.4 µg/mL, 2.6 µg/mL, 2.7 µg/mL, 2.8 µg/mL, or 2.9 µg/mL).

In certain embodiments of any of the methods described herein, the StAMP is administered with a second agent that inhibits the growth of the Gram-negative colistin-resistant bacterium. In some embodiments, the second agent is an antibiotic. In certain embodiments, the antibiotic is selected from the group consisting of carbapenem, an aminoglycoside, vancomycin, methicillin, clarithromycin, cephalosporin, penicillin, ampicillin, fluoroquinolone, tetracycline, and a β-lactam. In some embodiments, the second agent is a silver nanoparticle(s). In some embodiments, the second agent is a vaccine. In some embodiments, the second agent is phage therapy.

Also provided herein are methods of killing and/or inhibiting the growth of Gram-negative colistin-resistant bacteria that includes contacting the Gram-negative colistin-resistant bacteria with a stapled and/or stitched antimicrobial peptide (StAMP). In some embodiments, contacting is in vitro (e.g., under conventional conditions of cell culture, in a cell culture plate or dish, in an ex vivo cell culture system (i.e. propagation of cells that were previously in vivo)). In some embodiments, contacting is in vivo (e.g., in a subject (e.g., a human subject, an animal model, a cell that is inside the subject)). Various methods of detecting bacterial death and/or growth inhibition are known in the art, and include, but are not limited to: bacterial viability assay kit, cytotoxicity assay kit, LIVE/DEAD BacLight™ bacterial viability assay, microbroth dilution assay, and agar diffusion test. In certain embodiments, contacting can further include determining hemolytic activity.

Also provided herein are methods of determining a suitable treatment for a subject having, or suspected of having, an antibiotic-resistant Gram-negative bacterial infection, the method comprising: (a) obtaining a biological sample from the subject; (b) contacting the biological sample from the subject with a StAMP; (c) determining that the StAMP kills or inhibits the growth of the antibiotic-resistant Gram-negative bacteria in the sample; and (d) selecting and administering the StAMP to the subject. In some embodiments, the subject is a human.

In some embodiments, the antibiotic-resistant Gram-negative bacteria is colistin-resistant. In some embodiments, the StAMP is determined to have a hemolytic activity of less than 50% (e.g., less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, 0-4%, 0-2%, 0-1%, 1-4%, 1-3.5%, 1-3%, 1-2.5%, 1-2%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1% 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.95%, 0.9%, 0.8%, 0.7%, 0.6%, 0.5%, 0.4%, 0.3%, 0.25%, 0.2%, 0.1%, 0.095%, 0.09%, 0.085%, 0.08%, 0.075%, 0.07%, 0.065%, 0.06%, 0.055%, 0.05%, 0.045%, 0.04%, 0.035%, 0.03%, 0.025%, 0.02%, 0.015%, or 0.001%).

Also provided herein are methods for predicting the efficacy of a StAMP in treating a Gram-negative bacterial infection that include: contacting a Gram-negative bacteria responsible for a colistin-resistant Gram-negative bacterial infection with the StAMP; determining that the StAMP kills or inhibits the growth of the Gram-negative bacteria; and predicting that the StAMP is likely to treat the Gram-negative bacterial infection.

In some embodiments, the StAMP is determined to have a hemolytic activity of less than 50% (e.g., less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, 0-4%, 0-2%, 0-1%, 1-4%, 1-3.5%, 1-3%, 1-2.5%, 1-2%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1% 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.95%, 0.9%, 0.8%, 0.7%, 0.6%, 0.5%, 0.4%, 0.3%, 0.25%, 0.2%, 0.1%, 0.095%, 0.09%, 0.085%, 0.08%, 0.075%, 0.07%, 0.065%, 0.06%, 0.055%, 0.05%, 0.045%, 0.04%, 0.035%, 0.03%, 0.025%, 0.02%, 0.015%, or 0.001%).

In some embodiments of any of the methods described herein, the stapled and/or stitched antimicrobial peptide (StAMP) is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin.

In certain embodiments of any of the methods described herein, the StAMP comprises or consists of SEQ ID Nos.: 1-35. In certain embodiments, the StAMP comprises or consists of the amino acid sequence set forth in any one of SEQ ID Nos.: 1-35, except for at 1 to 5 amino acid substitutions, insertions, and/or deletions within SEQ ID Nos.: 1-35. In certain embodiments, the StAMP comprises or consists of any one of SEQ ID Nos.: 1-3, 34, or 35. In certain embodiments, the StAMP comprises or consists of the amino acid sequence set forth in any one of SEQ ID Nos.: 1-3, 34, or 35 except for at 1 to 5 amino acid substitutions, insertions, and/or deletions within SEQ ID Nos.: 1-3. In some embodiments, the StAMP comprises or consists of the sequence of any one of SEQ ID Nos.: 7, 9, 11, 13, 15, 17, 19, 21, 23, 25, 27, 29, 31, 33, 34, or 35 except for at 1 to 5 amino acid substitutions, insertions, and/or deletions within SEQ ID Nos.: 7, 9, 11, 13, 15, 17, 19, 21, 23, 25, 27, 29, 31, or 33. In some embodiments, the StAMP comprises or consists of the sequence of any one of SEQ ID Nos.: 1, 2, 3, 7, 9, 11, 13, 15, 17, 19, 21, 23, 25, 27, 29, 31, 33, 34, or 35. In certain embodiments of any of the methods described herein, the StAMP is double-stapled.

In some embodiments of any of the methods described herein, the StAMP is 6 to 100 amino acids in length (e.g., between 6 and 40 amino acids in length (e.g., between 6 and 10 amino acids in length, between 6 and 15 amino acids in length, between 6 and 20 amino acids in length, between 6 and 25 amino acids in length, between 6 and 30 amino acids in length, between 6 and 35 amino acids in length; between 10 and 15 amino acids in length, between 10 and 20 amino acids in length, between 10 and 25 amino acids in length, between 10 and 30 amino acids in length, between 10 and 35 amino acids in length; between 15 and 20 amino acids in length, between 15 and 25 amino acids in length, between 15 and 30 amino acids in length, between 15 and 35 amino acids in length; between 15 and 40 amino acids in length; between 20 and 25 amino acids in length, between 20 and 30 amino acids in length, between 20 and 35 amino acids in length; between 20 and 40 amino acids in length; between 30 and 35 amino acids in length; between 30 and 40 amino acids in length; or between 35 and 40 amino acids in length).

The disclosure includes methods of using the peptides herein for the prophylaxis and/or treatment of infection. The terms "treat", "treating", or "treatment" as used herein, refers to partially or completely alleviating, inhibiting, ameliorating, and/or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., infection) refers to any lessening, whether permanent or temporary, lasting or transient that can be attributed to or associated with treatment by the compositions and methods of the present disclosure. In some aspects, treatment can promote or result in, for example, a decrease in the number of microbial cells or organisms (e.g., in a subject) relative to the number of microbial cells or organisms prior to treatment; a decrease in the viability (e.g., the average/mean viability) of microbial cells or organisms (e.g., in a subject) relative to the viability (e.g., the average/ mean viability) of microbial cells or organisms (e.g., in the subject) prior to treatment; and/or reductions in one or more symptoms associated with one or more infections in a subject relative to the subject's symptoms prior to treatment.

Examples of bacteria internally cross-linked AMPS are active against include, without limitation, *Neisseria* (e.g., N. gonorrhea and *N. meningitidis*), *Chlamydia trachomatis*, *Treponema* (e.g., *T. pallidum*, *T. pertenue*, and T. ceratium), *Haemophilus* bacteria (e.g., *H. ducreyi*, *H. influenzae*, and *H. aegyptius*), (e.g., *B. pertussis*, *B. parapertussis*, and *B. bronchiseptica*), *Gardnerella vaginalis Borrelia burgdorferi*, *Actinobacillus pleuropneumonias*, *Helicobacter pylori*, *Escherichia coli*, *Porphyromonas gingivalis*, *Vibrio cholerae*, *Salmonella* bacteria (e.g., *S. enteritidis*, *S. typhimurium*, and *S. typhi*), *Shigella* bacteria, *Francisella* bacteria, *Yersinia* bacteria (e.g. *Y. pestis* and *Y. enterocolitica*), *Burkholderia* bacteria, *Pseudomonas* bacteria, and *Brucella* bacteria.

Disorders that can be treated by the compositions, formulations, and/or methods described herein include, but are not limited to, infectious diseases. Infectious diseases can be caused by pathogens, such as bacteria, viruses, fungi or parasites. In some aspects, an infectious disease can be passed from person to person. In some aspects, an infectious disease can be transmitted by bites from insects or animals. In some aspects, an infectious disease can be acquired by ingesting contaminated food or water or being exposed to organisms in the environment. Some infectious diseases can be prevented by vaccines.

In specific aspects, infectious diseases that can be treated by the compositions, formulations, and/or methods described herein include, but are not limited to, *Acinetobacter baumannii*, *Actinomyces israelii*, *Actinomyces gerencseriae* and *Propionibacterium* propionicus, *Trypanosoma brucei*, HIV (Human immunodeficiency virus), *Entamoeba histolytica*, *Anaplasma* species, *Angiostrongylus*, *Anisakis*, *Bacillus anthracis*, *Arcanobacterium haemolyticum*, *Junin virus*, *Ascaris lumbricoides*, *Aspergillus* species, Astroviridae family, *Babesia* species, *Bacillus cereus*, bacterial vaginosis microbiota, *Bacteroides* species, *Balantidium coli*, *Bartonella*, *Baylisascaris* species, BK virus, *Piedraia hortae*, *Blastocystis* species, *Blastomyces* dermatitidis, Machupo virus, *Clostridium botulinum*, Sabia, *Brucella* species, Enterobacteriaceae, *Burkholderia cepacia* and other *Burkholderia* species, *Mycobacterium ulcerans*, Caliciviridae family, *Campylobacter* species, *Candida albicans* and other *Candida* species, *Capillaria philippinensis*, *Capillaria hepatica*, *Capillaria aerophila*, *Bartonella bacilliformis*, *Bartonella henselae*, Group A *Streptococcus* and *Staphylococcus*, *Trypanosoma cruzi*, *Haemophilus ducreyi*, Varicella zoster virus (VZV), Alphavirus, *Chlamydia trachomatis*, *Chlamydophila pneumoniae*, *Vibrio cholera*, *Fonsecaea pedrosoi*, *Batrachochytrium* dendrobatidis, *Clonorchis sinensis*, *Clostridium difficile*, *Coccidioides immitis* and *Coccidioides posadasii*, Colorado tick fever virus (CTFV), rhinoviruses and coronaviruses, PRNP, Crimean-Congo hemorrhagic fever virus, *Cryptococcus neoformans*, *Cryptosporidium species*, *Ancylostoma braziliense*; multiple other parasites, *Cyclospora cayetanensis*, *Taenia solium*, Cytomegalovirus, Dengue viruses (DEN-1, DEN-2, DEN-3 and DEN-4) Flaviviruses, Green algae Desmodesmus armatus, *Dientamoeba fragilis*, *Corynebacterium diphtheria*, *Diphyllobothrium*, *Dracunculus medinensis*, Ebolavirus (EBOV), *Echinococcus* species, *Ehrlichia* species, *Enterobius vermicularis*, *Enterococcus* species, Enterovirus species, *Rickettsia prowazekii*, Parvovirus B19, Human herpesvirus 6 (HHV-6) and Human herpesvirus 7 (HHV-7), *Fasciola hepatica* and *Fasciola gigantica*, *Fasciolopsis buski*, PRNP, Filarioidea superfamily, *Clostridium perfringens*, *Fusobacterium species*, *Clostridium perfringens*, other *Clostridium* species, *Geotrichum candidum*, *Giardia lam-* blia, *Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenza*, Enteroviruses, mainly Coxsackie A virus and Enterovirus 71 (EV71), Sin Nombre virus, Heartland virus, *Helicobacter pylori, Escherichia coli* O157:H7, O111 and O104:H4, Bunyaviridae family, Hepatitis A virus, Hepatitis B virus, Hepatitis C virus, Hepatitis D Virus, Hepatitis E virus, Herpes simplex virus 1 and 2 (HSV-1 and HSV-2), *Histoplasma capsulatum, Ancylostoma duodenale* and *Necator americanus*, Human bocavirus (HBoV), *Ehrlichia ewingii, Anaplasma phagocytophilum*, Human metapneumovirus (hMPV), *Ehrlichia chaffeensis*, Human papillomavirus (HPV), Human parainfluenza viruses (HPIV), *Hymenolepis nana* and *Hymenolepis diminuta*, Epstein-Barr Virus (EBV), Orthomyxoviridae family, *Isospora belli, Kingella kingae*, Lassa virus, *Legionella pneumophila, Leishmania species, Mycobacterium leprae, Mycobacterium* lepromatosis, *Leptospira* species, *Listeria monocytogenes, Borrelia burgdorferi, Borrelia garinii, Borrelia afzelii, Wuchereria bancrofti, Brugia malayi*, Lymphocytic choriomeningitis virus (LCMV), *Plasmodium* species, Marburg virus, Measles virus, Middle East respiratory syndrome coronavirus, *Burkholderia pseudomallei, Neisseria meningitides, Metagonimus yokogawai*, Microsporidia phylum, Molluscum contagiosum virus (MCV), Monkeypox virus, Mumps virus, *Rickettsia typhi, Mycoplasma pneumoniae*, Actinomycetoma, Eumycetoma, parasitic dipterous fly larvae, *Chlamydia trachomatis, Neisseria gonorrhoeae, Nocardia asteroides, Nocardia species, Onchocerca volvulus, Opisthorchis viverrini* and *Opisthorchis felineus, Paracoccidioides brasiliensis, Pediculus humanus* capitis, *Phthirus pubis, Bordetella pertussis, Yersinia pestis, Streptococcus pneumoniae, Pneumocystis jirovecii*, Poliovirus, *Prevotella* species, *Naegleria fowleri*, JC virus, *Chlamydophila psittaci, Coxiella burnetii*, Rabies virus, *Borrelia hermsii, Borrelia recurrentis, Borrelia* species, Respiratory syncytial virus (RSV), *Rhinosporidium seeberi*, Rhinovirus, *Rickettsia* species, *Rickettsia akari*, Rift Valley fever virus, *Rickettsia*, Rotavirus, Rubella virus, *Salmonella* species, SARS coronavirus, *Sarcoptes scabiei, Schistosoma species, Shigella* species, Varicella zoster virus (VZV), *Variola major, Variola minor, Sporothrix schenckii, Staphylococcus species, Strongyloides stercoralis, Measles* virus, *Treponema pallidum, Taenia species, Clostridium tetani, Trichophyton species, Trichophyton tonsurans, Epidermophyton floccosum, Trichophyton rubrum, Trichophyton mentagrophytes, Trichophyton rubrum, Hortaea werneckii, Trichophyton species, Malassezia species, Toxocara canis, Toxocara cati, Chlamydia trachomatis, Toxoplasma gondii, Trichinella spiralis, Trichomonas vaginalis, Trichuris trichiura, Mycobacterium tuberculosis, Francisella tularensis, Salmonella enterica* subsp. *enterica*, serovar *typhi, Rickettsia, Ureaplasma urealyticum, Coccidioides immitis, Coccidioides posadasii*, Venezuelan equine encephalitis virus, Guanarito virus, *Vibrio vulnificus, Vibrio parahaemolyticus*, multiple viruses, West Nile virus, *Trichosporon beigelii, Yersinia pseudotuberculosis, Yersinia enterocolitica*, Yellow fever virus, Mucorales order (Mucormycosis), and Entomophthorales order (Entomophthoramycosis).

The compositions, formulations, and/or methods described herein can be used to treat a pathogen. In some aspects, the pathogen can be a virus, bacterium, prion, a fungus, or a parasite.

All the methods of treatment and prophylaxis described herein may be applied to at least any or all the above-listed microbial organisms.

In some aspects, the stapled and/or stitched anti-microbial peptide can be toxic to one colistin-resistant pathogen. In some aspects, the stapled and/or stitched anti-microbial peptide can be toxic to two microbes (e.g., Gram-negative bacteria). In some aspects, the stapled and/or stitched anti-microbial peptide can be toxic to three microbes (e.g., Gram-negative bacteria). In some aspects, the stapled and/or stitched anti-microbial peptide can be toxic to four microbes (e.g., Gram-negative bacteria). In some aspects, the stapled and/or stitched anti-microbial peptide can be toxic to five microbes (e.g., Gram-negative bacteria).

In some aspects, the stapled and/or stitched anti-microbial peptide can be used to treat a microbe (e.g., an antibiotic-resistant Gram-negative bacteria and/or a colistin-resistant Gram-negative bacteria) without damaging the host subject. In some aspects, the stapled and/or stitched anti-microbial peptide can be used to treat two microbes (e.g., Gram-negative bacteria) without damaging the host subject. In some aspects, the stapled and/or stitched anti-microbial peptide can be used to treat three microbes (e.g., Gram-negative bacteria) without damaging the host subject. In some aspects, the stapled and/or stitched anti-microbial peptide can be used to treat four microbes (e.g., Gram-negative bacteria) without damaging the host subject. In some aspects, the stapled and/or stitched anti-microbial peptide can be used to treat five microbes (e.g., Gram-negative bacteria) without damaging the host subject.

In general, methods include selecting a subject and administering to the subject an effective amount of one or more of the stapled and/or stitched anti-microbial peptide described herein, e.g., in or as a pharmaceutical composition, and optionally repeating administration as required for the prophylaxis or treatment of a Gram-negative colistin-resistant bacterial infection and can be administered, e.g., orally, intravenously or topically.

Specific dosage and treatment regimens for any particular patient will depend upon a variety of factors, including the activity of the specific stapled and/or stitched anti-microbial peptide used, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic stapled and/or stitched anti-microbial peptide (i.e., an effective dosage) depends on the therapeutic stapled and/or stitched anti-microbial peptide selected. The therapeutically effective amount of a stapled and/or stitched anti-microbial peptide can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present.

Moreover, treatment of a subject with a therapeutically effective amount of the therapeutic stapled and/or stitched anti-microbial peptide described herein can include a single treatment or a series of treatments. For example, effective amounts can be administered at least once. Upon improvement of a patient's condition, a maintenance dose of a stapled and/or stitched anti-microbial peptide, composition or combination of this disclosure may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the peptides herein can further be co-administered with one or more additional therapeutic agents in amounts effective for achieving a modulation of disease or disease symptoms. Such additional therapeutic agents may include conventional antimicrobial agents (e.g., antibiotics) known in the art. When co-administered, stapled AMPs of the disclosure operate in conjunction with conventional antimicrobial agents to produce mechanistically additive or synergistic antimicrobial effects. Without being limited by any particular mechanism of action, certain internally cross-linked (e.g., stapled) AMPs having the ability to produce "pores" in the membranes of certain microbial organisms (including, e.g., Gram-negative bacteria) can act to facilitate and/or enhance the passage of appropriate conventional antimicrobial agents to the interiors of relevant microbial cells. For the same purpose, the internally cross-linked AMPs can be conjugated (covalently or non-covalently) to appropriate antimicrobial agents, the resulting conjugates being administered to appropriate subjects.

The ability of internally cross-linked AMPs to produce "pores" in the membranes of microbial organisms provides the basis for another utility for them. Thus, e.g., relevant microbial organisms (e.g., any of those disclosed herein) can be contacted either in a subject or in vitro to an internally cross-linked AMP with the ability to produce "pores" or even lysis of the microbial organism. As result of this activity, nucleic acids (e.g., DNA and/or RNA) are released from microbial organisms into their surroundings. This phenomenon can be used as a basis for accurate, rapid, and inexpensive identification of the microbial organism. Where the contacting occurs in a subject, any of a variety of bodily fluids (e.g., blood, lymph, urine, feces, mucus, or tears) or body lavages can be tested. Where the contacting occurs in vitro, culture medium can be tested.

Methods of Optimizing a Stapled and/or Stitched Antimicrobial Peptide to Reduce Renal Toxicity Provided herein are methods for optimizing a stapled and/or stitched anti-microbial peptide (StAMP) to reduce the renal toxicity of the StAMP. In some embodiments, one or more amino acid substitutions, insertions, and/or deletions are introduced into a StAMP to reduce its renal toxicity, such that the StAMP is less likely to damage or kill kidney cells. For example, following an optimization to reduce renal toxicity, as described herein, the StAMP is less likely to damage or kill kidney cells in a subject following administration of the StAMP to the subject to treat a bacterial infection; e.g., an antibiotic-resistant bacterial infection. In some embodiments, serum creatinine levels can be measured to assess kidney filtration damage in a subject following the administration of a StAMP, e.g., a StAMP optimized as described herein to reduce renal toxicity. In some embodiments, urinary sediment may be measured to assess possible kidney cell pathology in a subject following administration of a StAMP. In some embodiments, the amount of serum creatinine and/or urinary sediment in a subject following administration of a StAMP, e.g., a StAMP optimized to reduce renal toxicity, can be compared to the amount of serum creatinine and/or urinary sediment present in one or more control subjects, e.g., a healthy subject not administered with a StAMP, a subject with a bacterial infection not administered with a StAMP, and/or a subject with a bacterial infection administered with a StAMP that has not been optimized to reduce renal toxicity.

In other embodiments, following optimization to reduce renal toxicity, the StAMP is less likely to damage or kill primary human renal proximal tubule epithelial cells (pRPTECs) when tested in an in vitro renal toxicity assay. Renal toxicity assays using pRPTECs are known in the art. In one embodiment, pRPTECs are seeded at a density of 10,000 cells per well on 96 well plates and incubated for 48 hours at 37° C. Cells are then treated with different concentrations of the StAMP and incubated for another 24-to-48 hour period. Cell viability is then determined and/or lactate dehydrogenase (LDH) release is measured. In some embodiments, the cell viability and/or LDH release of pRPTECs cells incubated with a StAMP optimized to reduce renal toxicity is compared to the cell viability and/or LDH release of control pRPTECs, e.g., pRPTECs cells not incubated with a StAMP or pRPTECs incubated with a StAMP that has not been optimized to reduce renal toxicity.

Altering the Hydrophobicity of Stapled and/or Stitched Anti-Microbial Peptides (StAMPs)

In some embodiments, the methods of optimizing the stapled and/or stitched anti-microbial peptide (StAMP) to reduce renal toxicity include: providing a first stapled and/or stitched anti-microbial peptide (StAMP), generating a second StAMP that is identical to the first StAMP except at one or more amino acid positions (e.g., 1, 2, 3, 4, 5, 6, 7, 8, 9, or 10 amino acid positions); and determining that the second StAMP exhibits reduced renal toxicity compared to the first StAMP e.g., by killing or damaging fewer kidney cells. In some embodiments, the second StAMP is tested for reduced renal toxicity relative to the first StAMP in vitro using a pRPTEC renal toxicity assay. In some embodiments, the renal toxicity of second StAMP is reduced relative to the renal toxicity of the first StAMP by at least 10% (e.g., at least 15%, at least 20%, at least 25%, at least 30%, at least 35%, at least 40%, at least 45%, at least 50%, at least 55%, at least 60%, at least 65%, at least 65%, at least 70%, at least 75%, at least 80%, at least 85%, at least 90%, at least 95%, or at least 99% reduced renal toxicity). In some embodiments, the second StAMP kills or damages at least 10% fewer pRPTECs in an in vitro toxicity assay than the first StAMP (e.g., at least 15%, at least 20%, at least 25%, at least 30%, at least 35%, at least 40%, at least 45%, at least 50%, at least 55%, at least 60%, at least 65%, at least 65%, at least 70%, at least 75%, at least 80%, at least 85%, at least 90%, at least 95%, or at least 99% fewer pRPTECs).

In some embodiments, the second StAMP comprises at least one amino acid substitution, wherein at least one hydrophobic amino acid in at least one hydrophobic patch is replaced with at least one amino acid with reduced hydrophobicity, thus disrupting at least one hydrophobic patch relative to the first StAMP. In some embodiments, the second StAMP includes 1, 2, 3, 4, or 5 amino acid substitutions in one hydrophobic patch. In some embodiments, the second StAMP includes 1, 2, 3, 4, 5, 6, 7, 8, 9, or 10 or more amino acid substitutions in at least two hydrophobic patches, thus disrupting two or more hydrophobic patches. In some embodiments, an amino acid with a hydrophobic side chain in a hydrophobic patch (an alanine, isoleucine, leucine, methionine, phenylalanine, tryptophan, tyrosine, or valine) is substituted with an amino acid that does not have a hydrophobic side chain. In some embodiments, the amino acid substitutions comprise replacing at least one amino acid in a hydrophobic patch with at least one natural or non-natural amino acid that is less hydrophobic than the amino acid being replaced in the hydrophobic patch. In some embodiments, at least one amino acid in a hydrophobic patch is substituted with a serine, asparagine, ornithine, threonine, arginine, histidine, norvaline, alanine or lysine.

In some embodiments, a StAMP that has been identified as killing or inhibiting the growth of antibiotic-resistant bacterium, e.g., a Gram-negative colistin-resistant bacterium, is modified using the methods described herein to reduce the renal toxicity of the StAMP. In some embodiments, the StAMP is based on or derived from the scaffold of a peptide selected from the group consisting of magainin, pexiganan, pleurocidin, pardaxin, hagfish intestinal antimicrobial peptide (HFIAP), PGQ, buforin II, dermaseptin, caerin, melittin, cecropin, lycotoxin I, styelins B, clavanin B, cathelicidin A, and dermicidin. In some embodiments, the StAMP is based on or derived from a peptide selected from the group consisting of SEQ ID Nos.: 4-33. In some embodiments, the StAMP is based on or derived from a peptide selected from the group consisting of SEQ ID Nos.: 1-3 or 35.

In some embodiments, the StAMP that has further been identified as exhibiting reduced hemolytic activity, as described herein, is modified to reduce the renal toxicity of the StAMP.

In some embodiments, the StAMP comprises or consists of the amino acid sequence set forth in any one of SEQ ID Nos.: 1-3 or 35-43 or any one of SEQ ID Nos.: 7, 9, 11, 13, 15, 17, 19, 21, 23, 25, 27, 29, 31, or 33, except for 1 to 5 amino acid substitutions, insertions, and/or deletions within SEQ ID Nos.: 1-3 or 35-43 or SEQ ID Nos.: 7, 9, 11, 13, 15, 17, 19, 21, 23, 25, 27, 29, 31, or 33. In some embodiments, the StAMP comprises an amino acid sequence that is at least 45% identical to the amino acid sequence of any of SEQ ID Nos.: 1-35, e.g., e.g., 45%, 50%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID Nos.: 1-35.

In some embodiments, the StAMP comprises or consists of the amino acid sequence set forth in any one of SEQ ID Nos.: 41-43. In some embodiments, the StAMP comprises an amino acid sequence that is at least 45% identical to the amino acid sequence of any of SEQ ID Nos.: 41-43, e.g., 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID Nos.: 41-43. In some embodiments, the StAMP comprises an amino acid sequence that differs from the amino acid sequence of any of SEQ ID Nos.: 41-43 by 1 or more amino acids, e.g., by 1, 2, 3, 4, 5, 6, 7, or 8 or more amino acids.

In some embodiments, the StAMP is 6 to 100 amino acids in length.

In some embodiments, the methods described herein include reducing the renal toxicity of a stapled and/or stitched anti-microbial peptide (StAMP) include: (i) identifying at least one hydrophobic patch comprising at least two hydrophobic amino acids (e.g., 2, 3, 4, or 5 or more hydrophobic amino acids that comprise a continuous or uninterrupted hydrophobic surface on the peptide); (ii) introducing at least one amino acid substitution in the hydrophobic patch, wherein at least one of the hydrophobic amino acids in hydrophobic patch is replaced with at least one amino acid with reduced hydrophobicity, to produce a StAMP with at least one disrupted hydrophobic patch; and (iii) testing the StAMP with the at least one disrupted hydrophobic patch for reduced renal toxicity relative to a StAMP that is identical except that no amino acid substitutions have been introduced into its hydrophobic patches, i.e., its hydrophobic patches have not been disrupted.

In some embodiments, the hydrophobic patch in the StAMP comprises 2 or more hydrophobic amino acids, e.g., 2, 3, 4, 5, 6, 7, 8, 9, or 10 or more amino acids. In some embodiments, the hydrophobic amino acids of the hydrophobic patch can be any combination of alanine, isoleucine, leucine, methionine, phenylalanine, tryptophan, tyrosine, or valine. In some embodiments, at least one hydrophobic amino acid of the hydrophobic patch can be a hydrophobic non-natural amino acid, e.g., norleucine, norvaline, d-alanine, homoalanine, and/or cyclobutylalanine.

As used herein, a "hydrophobic patch" is two or more hydrophobic amino acids, e.g., 2, 3, 4, 5, 6, 7, 8, 9, 10, or more hydrophobic amino acids, that make up a continuous hydrophobic surface area on a helical peptide, e.g., a continuous hydrophobic area on the surface of an alpha helix of a peptide or protein. In some cases, two or more consecutive hydrophobic amino acids in an amino acid sequence form a hydrophobic patch. In some cases, hydrophobic amino acids at the i+3 and i+4 positions form a continuous hydrophobic surface area on a helical peptide, and can therefore form a hydrophobic patch. Typically, the two or more hydrophobic amino acids that form a hydrophobic patch form a continuous hydrophobic surface area on the same face of a helical peptide. In some cases, an amino acid residue is considered hydrophobic if it has a hydrophobicity similar to that of alanine (a hydrophobicity value of 3.9, as determined by Kovacs et al. Biopolymers. 2006; 84(3):283-97) or higher, so that a hydrophobic patch is made of two or more amino acids that are each at least as hydrophobic as alanine. In some embodiments, an amino acid is considered hydrophobic if it has a hydrophobicity value of 3.5 or above, e.g., 3.9, as described by Kovacs et al. Biopolymers. 2006; 84(3): 283-97.

As used herein, a "disrupted hydrophobic patch" is a hydrophobic patch comprising two or more hydrophobic amino acids, e.g., 2, 3, 4, 5, 6, 7, 8, 9, 10, or more consecutive hydrophobic amino acids, wherein at least one of the hydrophobic amino acids that makes up the hydrophobic patch is mutated (e.g., by means of an amino acid substitution) to reduce the hydrophobicity of the hydrophobic patch. In some embodiments, a disrupted hydrophobic patch comprises at least one amino acid substitution wherein at least one of the amino acids of the patch is replaced with an amino acid having a lower hydrophobicity. In some cases, a disrupted hydrophobic patch comprises at least one amino acid substitution wherein at least one of the amino acids of the patch is replaced with a charged amino acid residue.

In some embodiments, at least one amino acid substitution is introduced into the StAMP to disrupt at least one hydrophobic patch, e.g., at least 1, 2, 3, 4, 5, 6, 7, 8, 9, or 10 or more substitutions are introduced into the StAMP to disrupt at least one hydrophobic patch. In some embodiments, one amino acid substitution is introduced into the StAMP to disrupt one hydrophobic patch. In some embodiments, at least two amino acid substitutions (e.g., 1, 2, 3, 4, or 5 amino acid substitutions) are introduced into the StAMP to disrupt one hydrophobic patch. In some embodiments, at least two amino acid substitutions (e.g., 1, 2, 3, 4, 5, 6, 7, 8, 9, or 10 or more amino acid substitutions) are introduced into the StAMP to disrupt at least two hydrophobic patches. For example, one or more amino acid substitutions can be introduced into a first hydrophobic patch to produce a first disrupted hydrophobic patch and one or more amino acids can be introduced into a second hydrophobic patch to produce a second disrupted hydrophobic patch. In some embodiments, a hydrophobic amino acid in a hydrophobic patch is substituted with an amino acid having a lower hydrophobicity. In some embodiments, a hydrophobic amino acid in a hydrophobic patch is substituted with a charged amino acid.

Hydrophobic patches within a peptide or protein may be identified using techniques generally known in the art, including, e.g., computational prediction/simulation (e.g., using ExPASy ProtScale, available at web.expasy.org/protscale/, Scooby-domain prediction, available at www.ibi.vu.nl/programs/scoobywww/, PSIPRED, available at bioinf.cs.ucl.ac.uk/psipred/, hydrophobic cluster analysis, see, e.g., www.impmc.upmc.fr/~callebau/HCA.html, Kyte Doolittle plotting, available at, e.g., gcat.davidson.edu/DGPB/kd/kyte-doolittle.htm or www.vivo.colostate.edu/molkit/hydropathy/index.html, and/or SPLIT, available at split.pmfst.hr/split/4/) and/or experimental determination (e.g., using techniques involving NMR spectroscopy, electron microscopy, homology modeling, small-angle X-ray and/or neutron scattering (SAXS/SANS), and/or X-ray crystallography) of the structure of the peptide or protein.

In some cases, introducing one or more mutations in a StAMP, e.g., amino acid substitutions, reduces the renal toxicity of the StAMP, but can also have the effect of reducing the antimicrobial activity of the StAMP. Thus, it may be desirable to further modify the StAMP to increase its antimicrobial activity to levels that are near or exceed the antimicrobial activity of the StAMP before the one or more mutations were introduced to reduce renal toxicity. In some embodiments, the antimicrobial activity of a StAMP comprising one or more disrupted hydrophobic patches is increased by introducing one or more mutations (e.g., a deletion, insertion, and/or a substitution) that make the hydrophilic portion of the StAMP more cationic. In some embodiments, the StAMP comprises an α-helical structure (e.g., an α-helix), wherein the α-helical structure has a hydrophobic portion or face and a hydrophilic portion or face. In some embodiments, the antimicrobial activity of a StAMP comprising one or more disrupted hydrophobic patches is increased by introducing one or more mutations (e.g., a deletion, insertion, and/or a substitution) that make the hydrophilic portion of the α-helix of the StAMP more cationic. In some embodiments, the hydrophilic portion of the StAMP (e.g., the hydrophilic portion of an α-helix) can be made more cationic by introducing an amino acid substitution that replaces a native amino acid with an amino acid that is more cationic, e.g., an amino acid that has a cationic side chain, such as an arginine, an omithine, a histidine, or a lysine. In some embodiments, at least one amino acid in the hydrophilic portion of a StAMP is substituted with at least one arginine, histidine, and/or lysine.

In some embodiments, the StAMP comprising at least one amino acid substitution (e.g., at least one arginine, omithine, histidine, and/or lysine substitution) that makes the hydrophilic portion of the StAMP (e.g., the hydrophilic portion of the α-helix) more cationic, exhibits greater anti-microbial activity relative to a StAMP that does not comprise at least one amino acid substitution that makes its hydrophilic portion more cationic. The levels of anti-microbial activity of the StAMPs can be determined using assays as described herein.

In some embodiments, the StAMP with reduced renal toxicity, as described herein, is administered to a subject, e.g., a human or animal, to treat an antibiotic-resistant bacterial infection. In some embodiments, the StAMP with reduced renal toxicity damages (e.g., disrupts cellular membranes, lyses, or kills) fewer kidney cells when administered to a subject relative to the StAMP that is identical except that it does not comprise an amino acid substitution that disrupts a hydrophobic patch. In some embodiments, the StAMP with reduced renal toxicity damages fewer primary renal proximal tubule epithelial cells (pRPTECs) in an in vitro renal toxicity assay relative to the StAMP that is identical except that it does not comprise an amino acid substitution that disrupts a hydrophobic patch.

Altering the Charge Nature of Stapled and/or Stitched Anti-Microbial Peptides (StAMPs)

Some antibiotics, such as colistin, cause renal nephrotoxicity during the course of treatment. The degree of renal nephrotoxicity can be influenced by the number of cationic point charges present on the antibiotic. For example, a significant determinant of the renal toxicity of colistin, a cationic lipopeptide, is determined by its number of cationic point charges. Colistin's renal toxicity profile can be improved by masking its point charges using methanesulfate.

In some cases, a StAMP having cationic charges that are point charges can exhibit renal toxicity in e.g., a pRPTEC toxicity assay. In some embodiments, changing the charge nature of one or more cationic point charges on the StAMP reduces the renal toxicity of the StAMP.

In some embodiments, the methods of optimizing the stapled and/or stitched anti-microbial peptide (StAMP) to reduce renal toxicity include: (i) identifying at least one amino acid residue on the StAMP that is a cationic point charge; (ii) introducing at least one amino acid substitution, wherein at least one cationic point charge is replaced with at least one amino acid with a different charge nature, thereby producing a StAMP with an altered cationic charge; and (iii) testing the StAMP with an altered cationic charge for reduced renal toxicity relative to a StAMP that is identical except that its cationic charge has not been altered.

In some embodiments, at least one amino acid substitution (e.g., 1, 2, 3, 4, 5, 6, 7, 8, 9, or 10 or more amino acid substitutions) is introduced into the StAMP to alter the charge nature of at least one cationic point charge (e.g., 1, 2, 3, 4, 5, 6, 7, 8, 9, or 10 or more cationic point charges). In some embodiments, one amino acid substitution is introduced into the StAMP to alter the charge nature of one cationic point charge. In some embodiments, at least two amino acid substitutions are introduced into the StAMP to alter the charge nature of at least two cationic point charges. A cationic point charge can be a cationic charge formed by the presence of a primary amine on the end of an amino acid side chain. In some embodiments, a cationic point charge can be any amino acid residue with a primary amine on its side chain. In some embodiments, the charge nature of one or more cationic point charges is altered, e.g., the side chain is altered such that the charge is either permanent or delocalized (e.g., by changing a lysine to an arginine) or more sensitive to pH changes (e.g., by changing a lysine to a histidine).

In some embodiments, the cationic point charge is a lysine. In some embodiments, the cationic point charge is a non-naturally occurring amino acid, such as omithine, 2,3-diaminopropionic acid, or N-trimethyl lysine. In some embodiments, the StAMP comprises at least one lysine that constitutes at least one cationic point charge. In some embodiments, at least one lysine on the StAMP is substituted with another cationic amino acid, i.e., another amino acid with a cationic side chain. In some embodiments, at least one cationic point charge, e.g., at least one lysine, is substituted with at least one amino acid with a delocalized cationic charge, e.g., at least one arginine. In some embodiments, at least one cationic point charge, e.g., at least one lysine, is substituted with at least one amino acid with a cationic charge that can become protonated under certain conditions, e.g., at least one histidine (which can be protonated at a pH below 6). In some embodiments, any lysine on any portion of the StAMP can be substituted with an arginine or a histidine to alter the charge nature of the StAMP. In some embodiments, any lysine on a hydrophilic face or surface of the StAMP can be substituted with an arginine or a histidine to alter the charge nature of the StAMP. In some embodiments, the primary amine of at least one lysine on the StAMP is changed into a pyridinium cap, e.g., through the Zincke reaction, to make a highly delocalized cationic charge. In some embodiments, any lysine on any portion of the StAMP can be substituted with an omithine to alter the charge nature of the StAMP.

In some embodiments, the StAMP comprises or consists of the amino acid sequence set forth in any one of SEQ ID Nos.: 1-3 or 35-43 or any one of SEQ ID Nos.: 7, 9, 11, 13, 15, 17, 19, 21, 23, 25, 27, 29, 31, or 33, except for 1 to 5 amino acid substitutions, insertions, and/or deletions within SEQ ID Nos.: 1-3 or 35-43 or SEQ ID Nos.: 7, 9, 11, 13, 15, 17, 19, 21, 23, 25, 27, 29, 31, or 33. In some embodiments, the StAMP comprises an amino acid sequence that is at least 45% identical to the amino acid sequence of any of SEQ ID Nos.: 1-35, e.g., e.g., 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID Nos.: 1-35.

In some embodiments, the StAMP comprises or consists of the amino acid sequence set forth in any one of SEQ ID Nos.: 36-40. In some embodiments, the StAMP comprises an amino acid sequence that is at least 45% identical to the amino acid sequence of any of SEQ ID Nos.: 36-40, e.g., 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID Nos.: 36-40. In some embodiments, the StAMP comprises an amino acid sequence that differs from the amino acid sequence of any of SEQ ID Nos.: 36-40 by 1 or more amino acids, e.g., by 1, 2, 3, 4, 5, 6, 7, or 8 or more amino acids.

In some embodiments, a StAMP comprising at least one amino acid substitution that alters the charge nature of at least one cationic point charge (e.g., 1, 2, 3, 4, 5, 6, 7, 8, 9, or 10 or more amino acid substitutions wherein at least one lysine is replaced with at least one arginine and/or histidine) exhibits reduced renal toxicity relative to a StAMP that is identical except that it does not comprise an amino acid substitution that alters the charge nature of a cationic point charge.

In some embodiments, the StAMP with reduced renal toxicity, as described herein, is administered to a subject, e.g., a human or animal, to treat an antibiotic-resistant bacterial infection. In some embodiments, the StAMP with reduced renal toxicity damages fewer kidney cells when administered to a subject relative to the StAMP that is identical except that it does not comprise an amino acid substitution that alters the charge nature of a cationic point charge. In some embodiments, the StAMP with reduced renal toxicity lyses fewer primary renal proximal tubule epithelial cells (pRPTECs) in an in vitro renal toxicity assay relative to the StAMP that is identical except that it does not comprise an amino acid substitution that alters the charge nature of a cationic point charge.

In some embodiments, the methods of optimizing the stapled and/or stitched anti-microbial peptide (StAMP) to reduce renal toxicity include: providing a first stapled and/or stitched anti-microbial peptide (StAMP), generating a second StAMP that is identical to the first StAMP except at one or more amino acid positions (e.g., 1, 2, 3, 4, 5, 6, 7, 8, 9, or 10 amino acid positions); and determining that the second StAMP exhibits reduced renal toxicity compared to the first StAMP e.g., by killing or damaging fewer kidney cells. In some embodiments, the second StAMP is tested for reduced renal toxicity relative to the first StAMP in vitro using a pRPTEC renal toxicity assay. In some embodiments, the renal toxicity of second StAMP is reduced relative to the renal toxicity of the first StAMP by at least 10% (e.g., at least 15%, at least 20%, at least 25%, at least 30%, at least 35%, at least 40%, at least 45%, at least 50%, at least 55%, at least 60%, at least 65%, at least 65%, at least 70%, at least 75%, at least 80%, at least 85%, at least 90%, at least 95%, or at least 99% reduced renal toxicity). In some embodiments, the second StAMP kills or damages at least 10% fewer pRPTECs in an in vitro toxicity assay than the first StAMP (e.g., at least 15%, at least 20%, at least 25%, at least 30%, at least 35%, at least 40%, at least 45%, at least 50%, at least 55%, at least 60%, at least 65%, at least 65%, at least 70%, at least 75%, at least 80%, at least 85%, at least 90%, at least 95%, or at least 99% fewer pRPTECs).

Stapled and/or Stitched Antimicrobial Peptides with Reduced Renal Toxicity

In some aspects, stapled and/or stitched antimicrobial peptide (StAMPs) can have 5, 6, 7, 8, 9, 10, 11, 12, 13, 14, 15, 16, 17, 18, 19, 20, 21, 22, 23, 24, 25, 26, 27, 28, 29, 30 or more amino acids.

In some embodiments, a StAMP described herein features a polypeptide of Formula (I),

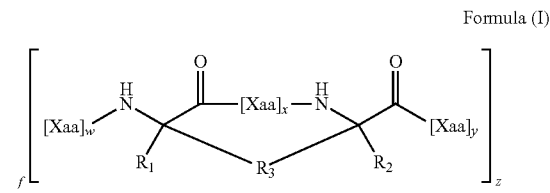

Formula (I)

or a pharmaceutically acceptable salt thereof,
wherein:
each $R_1$ and $R_2$ is independently H, alkyl, alkenyl, alkynyl, arylalkyl, cycloalkylalkyl, heteroarylalkyl, or heterocyclylalkyl, any of which is substituted or unsubstituted;
each $R_3$ is independently alkylene, alkenylene, or alkynylene, any of which is substituted or unsubstituted;
each x is independently 1, 2, 3, 4, 5, 6, 7, 8, 9, or 10;
each w and y is independently 1, 2, 3, 4, 5, 6, 7, 8, 9, 10, 11, 12, 13, 14, 15, 16, 17, 18, 19, or 20;
z is 1, 2, 3, 4, 5, 6, 7, 8, 9, or 10; and
each Xaa is independently an amino acid,
wherein the StAMP exhibits an antimicrobial effect against at least one microbe, and wherein
the [Xaa]$_w$ and/or [Xaa]$_y$ of the StAMP comprises at least one hydrophobic patch of two or more hydrophobic amino acids that is identical to a hydrophobic patch present on an anti-microbial peptide (AMP) that is identical to the StAMP of Formula I except that at least one of the two or more hydrophobic amino acids of the hydrophobic patch of the StAMP is substituted with an amino acid having reduced hydrophobicity;

and/or the StAMP comprises an amino acid substitution that alters the charge nature of a cationic point charge relative an anti-microbial peptide (AMP) that is identical to the StAMP of Formula I.

As used above, and elsewhere in the present document, an anti-microbial peptide (AMP) that is identical to the StAMP of Formula I, and it does not comprise an amino acid substitution present in the StAMP that disrupts a hydrophobic patch or changes the charge nature of a cationic point charge, can be a wild-type AMP, or any of the variants of a wild-type AMP disclosed in the present document, except that such a variant would not include an internal cross-link as described herein. In some embodiments, the anti-microbial peptide (AMP) comprises an amino acid selected from the group consisting of: SEQ ID Nos.: 4-33.

Various characteristics of StAMPs and methods of making and purifying StAMPs, are described in U.S. Patent Publication 2017/0015716, which is herein incorporated in its entirety. In the case of Formula I, the following aspects are among those disclosed.

In cases where x=2 (i.e., i+3 linkage), $R_3$ can be, for example, a $C_7$ alkylene, alkenylene. Where it is an alkenylene, there can be one or more double bonds. In cases where x=6 (i.e., i+4 linkage), $R_3$ can be, for example, a $C_{11}$, $C_{12}$, or $C_{13}$ alkylene or alkenylene. Where it is an alkenylene there can be one or more double bonds. In cases where x=3 (i.e., i+4 linkage), $R_3$ can be, for example, a $C_8$ alkylene, alkenylene. Where it is an alkenylene, there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

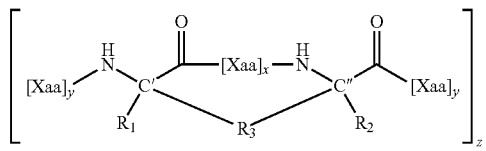

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. An $R_3$ double bond (based on the definition above, $R_3$ contains an alkane, alkene, or alkyne moiety; in general, it is an alkene) can be in the E or Z stereochemical configuration.

In some embodiments, the anti-microbial peptide (AMP) comprises an amino acid selected from the group consisting of: SEQ ID Nos.: 4-33. In some embodiments, the anti-microbial peptide (AMP) comprises an amino acid that is at least 45% identical to an amino acid selected from the group consisting of SEQ ID Nos.: 4-33, e.g., 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID Nos.: 4-33. In some embodiments, the AMP comprises an amino acid sequence that differs from the amino acid sequence of any of SEQ ID Nos.: 4-33 by 1 or more amino acids, e.g., by 1, 2, 3, 4, 5, 6, 7, or 8 or more amino acids.

In some instances, the StAMP includes an amino acid sequence which, in addition to the amino acids side chains that are replaced by a cross-link, have 1, 2, 3, 4, 5, 6, 7, 8, 9, 10, 11, or 12 amino acid changes (e.g., conservative amino acid changes) in any of SEQ ID Nos.: 4-33.

In some embodiments, the stapled and/or stitched anti-microbial peptide (StAMP) comprises an α-helix.

In some embodiments, the StAMP comprises an amino acid sequence selected form the group consisting of SEQ ID Nos.: 36-43. In some embodiments, the StAMP comprises an amino acid sequence that is at least 45% identical to an amino acid sequence selected from the group consisting of SEQ ID Nos.: 36-43 e.g., 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any of SEQ ID Nos.: 36-43. In some embodiments, the StAMP comprises an amino acid sequence that differs from the amino acid sequence of any of SEQ ID Nos.: 36-43 by 1 or more amino acids, e.g., by 1, 2, 3, 4, 5, 6, 7, or 8 or more amino acids.

In some embodiments, the $[Xaa]_w$ and/or $[Xaa]_y$ of a StAMP described herein comprises at least one hydrophobic patch (e.g., 1, 2, 3, 4, 5, 6, 7, or 8 hydrophobic patches) that has been disrupted with an amino acid substitution relative to the anti-microbial peptide (AMP). In some embodiments, the $[Xaa]_w$ of a StAMP described herein comprises at least one hydrophobic patch that has been disrupted with an amino acid substitution relative to the anti-microbial peptide (AMP). In some embodiments, the $[Xaa]_y$ of a StAMP described herein comprises at least one hydrophobic patch that has been disrupted with an amino acid substitution relative to the anti-microbial peptide (AMP). In some embodiments, both the $[Xaa]_y$ and the $[Xaa]_w$ of a StAMP described herein comprises at least one hydrophobic patch that has been disrupted with an amino acid substitution relative to the anti-microbial peptide (AMP).

In some embodiments, at least one amino acid on the hydrophilic portion of a StAMP described herein, e.g., the hydrophilic portion of the α-helix, is substituted with an amino acid that makes the hydrophilic portion of the StAMP more cationic. In some embodiments, the hydrophilic portion of the StAMP (e.g., the hydrophilic portion of the α-helix) comprises an amino acid substitution that replaces a native amino acid with an amino acid that is more cationic, e.g., an amino acid that has a cationic side chain, such as an arginine, a histidine, ornithine, or a lysine. In some embodiments, a StAMP described herein comprises at least one amino acid substitution in the hydrophilic portion of the StAMP, wherein at least one native amino acid is substituted with a at least one arginine, histidine, ornithine, and/or lysine. In some embodiment, the StAMP exhibits greater anti-microbial activity relative to a StAMP that is identical except that it does not comprise a lysine, arginine, or histidine substitution on the hydrophilic portion of its α-helix. In some embodiments, a StAMP as described herein comprises at least one amino acid substitution that alters the charge nature of at least one cationic point charge (e.g., 1, 2, 3, 4, 5, 6, 7, 8, 9, or 10 or more cationic point charges) relative to the anti-microbial peptide (AMP). In some embodiments, the StAMP comprises one amino acid substitution that alters the charge nature of one cationic point charge relative to the anti-microbial peptide (AMP). In some embodiments, a StAMP as described herein comprises at least two amino acid substitutions that alter the charge nature of at least two cationic point charges relative to the antimicrobial peptide (AMP).

In some embodiments, the StAMP comprises at least one lysine that constitutes at least one cationic point charge. In some embodiments, at least one lysine on the StAMP is substituted with another cationic amino acid, i.e., another amino acid with a cationic side chain. In some embodiments, at least one cationic point charge, e.g., at least one lysine, is substituted with at least one amino acid with a delocalized cationic charge, e.g., at least one arginine. In some embodiments, at least one cationic point charge, e.g., at least one lysine, is substituted with at least one amino acid with a cationic charge that can become protonated under certain conditions, e.g., at least one histidine (which can be protonated at a pH below 6). In some embodiments, any lysine on any portion of the StAMP can be substituted with an arginine or a histidine to alter the charge nature of the StAMP. In some embodiments, any lysine on any portion of the StAMP can be substituted with an ornithine to alter the charge nature of the StAMP.

In some embodiments, a StAMP as described herein exhibits a reduced renal toxicity when it is administered to a subject, e.g., a human or animal, to treat an antibiotic-resistant bacterial infection. In some embodiments, the StAMP with reduced renal toxicity damages fewer kidney cells when administered to a subject relative to the StAMP that is identical except that it does not comprise at least one amino acid substitution that disrupts at least one hydrophobic patch and/or alters the charge nature of at least one cationic point charge. In some embodiments, the StAMP with reduced renal toxicity lyses fewer primary renal proximal tubule epithelial cells (pRPTECs) in an in vitro renal toxicity assay relative to the StAMP that is identical except that it does not comprise at least one amino acid substitution that disrupts at least one hydrophobic patch and/or alters the charge nature of a cationic point charge.

In some embodiments, a StAMP as described herein is formulated as a pharmaceutical composition for administration to a subject.

In some aspects, the StAMP comprises at least one helical motif, such as a $3_{10}$ or an $\alpha$-helix motif. For example, A, B, and/or C in the StAMP of Formula I include one or more helices. As a general matter, helices include from 3 to 4 amino acid residues per turn. In some aspects, the helix of the StAMP includes 1 to 5 turns and, therefore, 3 to 20 amino acid residues. In specific aspects, the helix includes 1 turn, 2 turns, 3 turns, 4 turns, or 5 turns. In some aspects, the macrocycle-forming linker stabilizes a helix motif included within the StAMP. Thus, in some aspects, the length of the macrocycle-forming linker L from a first $\alpha$-carbon to a second $\alpha$-carbon is selected to increase the stability of a helix. In some aspects, the macrocycle-forming linker spans from 1 turn to 5 turns of the helix. In some aspects, the macrocycle-forming linker spans approximately 1 turn, 2 turns, 3 turns, 4 turns, or 5 turns of the helix. In some aspects, the length of the macrocycle-forming linker is approximately 5 Å to 9 Å per turn of the helix, or approximately 6 Å to 8 Å per turn of the helix. Where the macrocycle-forming linker spans approximately 1 turn of a helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of a helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of a helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of a helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of a helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of a helix, the linkage contains approximately 4 atoms to 12 atoms, approximately 6 atoms to 10 atoms, or approximately 8 atoms. Where the macrocycle-forming linker spans approximately 2 turns of the helix, the linkage contains approximately 7 atoms to 15 atoms, approximately 9 atoms to 13 atoms, or approximately 11 atoms. Where the macrocycle-forming linker spans approximately 3 turns of the helix, the linkage contains approximately 13 atoms to 21 atoms, approximately 15 atoms to 19 atoms, or approximately 17 atoms. Where the macrocycle-forming linker spans approximately 4 turns of the helix, the linkage contains approximately 19 atoms to 27 atoms, approximately 21 atoms to 25 atoms, or approximately 23 atoms. Where the macrocycle-forming linker spans approximately 5 turns of the helix, the linkage contains approximately 25 atoms to 33 atoms, approximately 27 atoms to 31 atoms, or approximately 29 atoms. Where the macrocycle-forming linker spans approximately 1 turn of the helix, the resulting macrocycle forms a ring containing approximately 17 members to 25 members, approximately 19 members to 23 members, or approximately 21 members. Where the macrocycle-forming linker spans approximately 2 turns of the helix, the resulting macrocycle forms a ring containing approximately 29 members to 37 members, approximately 31 members to 35 members, or approximately 33 members. Where the macrocycle-forming linker spans approximately 3 turns of the helix, the resulting macrocycle forms a ring containing approximately 44 members to 52 members, approximately 46 members to 50 members, or approximately 48 members. Where the macrocycle-forming linker spans approximately 4 turns of the helix, the resulting macrocycle forms a ring containing approximately 59 members to 67 members, approximately 61 members to 65 members, or approximately 63 members. Where the macrocycle-forming linker spans approximately 5 turns of the helix, the resulting macrocycle forms a ring containing approximately 74 members to 82 members, approximately 76 members to 80 members, or approximately 78 members.

The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

Methods of synthesizing the StAMPS described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the StAMPs described herein are known in the art and include, e.g., those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The StAMPs of this invention can be made by chemical synthesis methods, which are well known to the ordinarily skilled artisan. See, e.g., Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the $\alpha$-$NH_2$ protected by either t-Boc or Fmoc chemistry using side chain protected amino acids on, for example, an Applied Biosystems Peptide Synthesizer Model 430A or 431.

One manner of making of the StAMPs described herein is using solid phase peptide synthesis (SPPS). The C-terminal amino acid is attached to a cross-linked polystyrene resin or polyethylene glycol (PEG) resin or via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a StAMP of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector, optionally modified to introduce mutations of interest, and transfected into a host cell. The peptide is then expressed under suitable conditions appropriate for the selected expression system and host. The peptide is purified and characterized by standard methods.

The StAMPs can be made in a high-throughput, combinatorial fashion, e.g., using a high-throughput multiple channel combinatorial synthesizer available from Advanced Chemtech.

Methods suitable for obtaining (e.g., synthesizing), stapling, and purifying the peptides disclosed herein are also known in the art (see, e.g., Bird et. al., *Meth Enzymol.*, 446:369-386 (2008); Bird et al, *Curr Protoc Chem Biol.*, 2011; Walensky et al., *Science*, 305:1466-1470 (2004); Schafmeister et al., *J Am Chem Soc.*, 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some aspects, the StAMPs are substantially free of non-stapled peptide contaminants or are isolated. Methods for purifying StAMPS include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50%, or 60% DMSO. In a specific aspect, a 50%/50% DMSO/NMP solution is used. The solution may be incubated for a period of 1, 6, 12, or 24 hours, following which the resin may be washed, for example with dichloromethane or NMP. In one aspect, the resin is washed with NMP. Shaking and bubbling an inert gas into the solution may be performed.

Pharmaceutical Compositions

One or more of the peptides (e.g., hydrocarbon-stapled and/or stitched antimicrobial peptides) disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/FormsSubmissionRequirements/ElectronicSubmissions/DataStandardsManualmonographs).

The pharmaceutical compositions of this disclosure may be administered, e.g., orally, parenterally, by inhalation spray or nebulizer, topically, rectally, nasally, buccally, vaginally, via an implanted reservoir, by injection (e.g., intravenously, intra-arterially, subdermally, intraperitoneally, intramuscularly, and/or subcutaneously), in an ophthalmic preparation, or via transmucosal administration. When the StAMPs disclosed herein are to be administered intravenously to a subject, the hemolysis threshold is 20% or less. When the StAMPs disclosed herein are to be administered via a non-intravenous route to a subject, the hemolysis threshold can be greater than 20% and less than 100%. Suitable dosages may range from about 0.001 to about 100 mg/kg of body weight, or according to the requirements of the particular drug. The pharmaceutical compositions of this disclosure may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques. Alternatively, or in addition, the present disclosure may be administered according to any of the methods as described in the FDA DSM.

As used herein, the stapled and/or stitched anti-microbial peptides are defined to include pharmaceutically acceptable derivatives or prodrugs thereof. A "pharmaceutically acceptable derivative or prodrug" means any pharmaceutically acceptable salt, ester, salt of an ester, or other derivative of a compound or agent disclosed herein which, upon administration to a recipient, is capable of providing (directly or indirectly) a stapled and/or stitched anti-microbial peptide as described herein. Particularly favored derivatives and prodrugs are those that increase the bioavailability of the compounds of this disclosure when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of infection).

The methods herein contemplate administration of an effective amount of compound or compound composition to achieve the desired or stated effect. Typically, the pharmaceutical compositions of this disclosure can be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Dosing can be determined using various techniques. The selected dosage level can depend upon a variety of factors, including, e.g., the activity of the particular compound employed, the route of administration, the time of administration, the rate of excretion or metabolism of the particular compound being employed, the duration of the treatment, other drugs, compounds, and/or materials used in combination with the particular compound employed, the age, sex, weight, condition, general health, and/or prior medical history of the patient being treated, and like factors well known in the medical arts. The dosage values can also vary with the severity of the condition to be alleviated. For any particular subject, specific dosage regimens can be adjusted over time according to the individual need and the professional judgment of the person administering or supervising the administration of the compositions.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some aspects, a dose can be expressed in terms of an amount of the drug divided by the mass of the subject, for example, milligrams of drug per kilograms of subject body mass. In some aspects, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Dosage can be based on the amount of the compound per kg body weight of the patient. Alternatively, the dosage of the subject disclosure can be determined by reference to the plasma concentrations of the compound. For example, the maximum plasma concentration ($C_{max}$) and the area under the plasma concentration-time curve from time 0 to infinity (AUC) can be used.

In some aspects, the subject is a human subject and the amount of the compound administered is 0.01-100 mg per kilogram body weight of the human subject. For example, in various examples, the amount of the compound administered is about 0.01-50 mg/kg, about 0.01-20 mg/kg, about 0.01-10 mg/kg, about 0.1-100 mg/kg, about 0.1-50 mg/kg, about 0.1-20 mg/kg, about 0.1-10 mg/kg, about 0.5-100 mg/kg, about 0.5-50 mg/kg, about 0.5-20 mg/kg, about 0.5-10 mg/kg, about 1-100 mg/kg, about 1-50 mg/kg, about 1-20 mg/kg, about 1-10 mg/kg body weight of the human subject. In one aspect, about 0.5 mg-10 mg of the compound per kilogram body weight of the human subject is administered. In some examples the amount of the compound administered is about 0.16 mg, about 0.32 mg, about 0.64 mg, about 1.28 mg, about 3.56 mg, about 7.12 mg, about 14.24 mg, or about 20 mg per kilogram body weight of the human subject. In some examples the amount of the compound administered is about 0.16 mg, about 0.32 mg, about 0.64 mg, about 1.28 mg, about 3.56 mg, about 7.12 mg, or about 14.24 mg per kilogram body weight of the human subject. In some examples the amount of the compound administered is about 0.16 mg per kilogram body weight of the human subject. In some examples the amount of the compound administered is about 0.32 mg per kilogram body weight of the human subject. In some examples the amount of the compound administered is about 0.64 mg per kilogram body weight of the human subject. In some examples the amount of the compound administered is about 1.28 mg per kilogram body weight of the human subject. In some examples the amount of the compound administered is about 3.56 mg per kilogram body weight of the human subject. In some examples the amount of the compound administered is about 7.12 mg per kilogram body weight of the human subject. In some examples the amount of the compound administered is about 14.24 mg per kilogram body weight of the human subject.

In some aspects about 0.5- about 20 mg or about 0.5- about 10 mg of the compound per kilogram body weight of the human subject is administered two times a week. For example, about 0.5- about 1 mg, about 0.5- about 5 mg, about 0.5- about 10 mg, about 0.5- about 15 mg, about 1-about 5 mg, about 1-about 10 mg, about 1-about 15 mg, about 1-about 20 mg, about 5-about 10 mg, about 1-about 15 mg, about 5-about 20 mg, about 10-about 15 mg, about 10-about 20 mg, or about 15-about 20 mg of the compound per kilogram body weight of the human subject is administered about twice a week. In some examples, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, or about 20 mg of the compound per kilogram body weight of the human subject is administered two times a week. In some examples, the amount of the compound administered is about 1.25 mg, about 2.5 mg, about 5 mg, about 10 mg, or about 20 mg per kilogram body weight of the human subject and the compound is administered two times a week. In some examples, the amount of the compound administered is about 1.25 mg, about 2.5 mg, about 5 mg or about 10 mg per kilogram body weight of the human subject. The compound can be administered once a week, two times a week, three, four, five, six, or seven times a week. The compound can be administered once every 3 weeks.

In some aspects, the compound is administered gradually over a period of time. A desired amount of compound can, for example can be administered gradually over a period of from about 0.1 h-24 h. In some cases, a desired amount of compound is administered gradually over a period of 0.1 h, 0.5 h, 1 h, 1.5 h, 2 h, 2.5 h, 3 h, 3.5 h, 4 h, 4.5 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h. In some examples, a desired amount of compound is administered gradually over a period of 0.25-12 h, for example over a period of 0.25-1 h, 0.25-2 h, 0.25-3 h, 0.25-4 h, 0.25-6 h, 0.25-8 h, or 0.25-10 h. In some examples, a desired amount of compound is administered gradually over a period of 0.25-2 h. In some examples, a desired amount of compound is administered gradually over a period of 0.25-1 h. In some examples, a desired amount of compound is administered gradually over a period of 0.25 h, 0.3 h, 0.4 h, 0.5 h, 0.6 h, 0.7 h, 0.8 h, 0.9 h, 1.0 h, 1.1 h, 1.2 h, 1.3 h, 1.4 h, 1.5 h, 1.6 h, 1.7 h, 1.8 h, 1.9 h, or 2.0 h. In some examples, a desired amount of compound is administered gradually over a period of 1 h. In some examples, a desired amount of compound is administered gradually over a period of 2 h.

Administration of the compounds can continue as long as necessary. In some aspects, one or more compound of the disclosure is administered for more than 1 day, more than 1 week, more than 1 month, more than 2 months, more than 3 months, more than 4 months, more than 5 months, more than 6 months, more than 7 months, more than 8 months, more than 9 months, more than 10 months, more than 11 months, more than 12 months, more than 13 months, more than 14 months, more than 15 months, more than 16 months, more than 17 months, more than 18 months, more than 19 months, more than 20 months, more than 21 months, more than 22 months, more than 23 months, or more than 24 months. In some aspects, one or more compound of the disclosure is administered for less than 1 week, less than 1 month, less than 2 months, less than 3 months, less than 4 months, less than 5 months, less than 6 months, less than 7 months, less than 8 months, less than 9 months, less than 10 months, less than 11 months, less than 12 months, less than 13 months, less than 14 months, less than 15 months, less than 16 months, less than 17 months, less than 18 months, less than 19 months, less than 20 months, less than 21 months, less than 22 months, less than 23 months, or less than 24 months.

In some aspects, the compound is administered on day 1, 8, 15, and 28 of a 28-day cycle. In some aspects, the compound is administered on day 1, 8, 15, and 28 of a 28-day cycle and administration is continued for two cycles. In some aspects, the compound is administered on day 1, 8, 15, and 28 of a 28-day cycle and administration is continued for three cycles. In some aspects, the compound is administered on day 1, 8, 15, and 28 of a 28-day cycle and administration is continued for 4, 5, 6, 7, 8, 9, 10, or more cycles.

In some aspects, the compound is administered on day 1, 8, 11, and 21 of a 21-day cycle. In some aspects, the compound is administered on day 1, 8, 11, and 21 of a 21-day cycle and administration is continued for two cycles. In some aspects, the compound is administered on day 1, 8, 11, and 21 of a 21-day cycle and administration is continued for three cycles. In some aspects, the compound is administered on day 1, 8, 11, and 21 of a 21-day cycle and administration is continued for 4, 5, 6, 7, 8, 9, 10, or more cycles.

In some aspects, one or more compound of the disclosure is administered chronically on an ongoing basis. In some aspects administration of one or more compound of the disclosure is continued until documentation of disease progression, unacceptable toxicity, or patient or physician decision to discontinue administration.

In some aspects, a suitable daily dose of a compound of the disclosure can be that amount of the compound which is the lowest dose effective to produce a therapeutic effect. Such an effective dose will generally depend upon the factors described above. The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like.

A physician can prescribe the effective amount of the pharmaceutical composition required. For example, the physician could start doses of the compounds of the disclosure employed in the pharmaceutical composition at levels lower than that required in order to achieve the desired therapeutic effect and gradually increase the dosage until the desired effect is achieved.

The compounds of this disclosure may be modified by appending appropriate functionalities to enhance selective biological properties (including, e.g., hydrophobicity and/or the position/occurrence of hydrophobic patches). Such modifications are known in the art and include those which increase biological penetration into a given biological compartment (e.g., blood, lymphatic system, central nervous system), increase oral availability, increase solubility to allow administration by injection, alter metabolism and alter rate of excretion.

An antimicrobial peptide selective for microbial versus mammalian membranes (i.e., a peptide able to kill or inhibit the growth of a microbe (e.g., Gram-negative bacteria, an antibiotic-resistant Gram-negative bacteria) while also having a relatively low ability to lyse or inhibit the growth of a mammalian cell) may, e.g., possess a MIC for one or more microbes (e.g., Gram-negative bacteria, an antibiotic-resistant Gram-negative bacteria) more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than the MIC of the corresponding parent (i.e., unmodified) non-internally cross-linked peptide for the same one or more microbes (e.g., Gram-negative bacteria, an antibiotic-resistant Gram-negative bacteria). In addition, an antimicrobial peptide selective for microbial versus mammalian membranes may lyse, e.g., less than 50%, less than 40%, less than 30%, less than 25%, less than 20%, less than 15%, less than 10%, less than 5%, less than 2.5%, less than 2%, or less than 1% of red blood cells (RBCs) in a RBC hemolytic activity assay when administered at its MIC for one or more microbes (e.g., Gram-negative bacteria, an antibiotic-resistant Gram-negative bacteria). The RBC hemolytic activity of an antimicrobial peptide selective for microbial versus mammalian membranes may be less than, approximately equal to, less than 1.5-fold greater, less than 2-fold greater, less than 2.5-fold greater, less than 3-fold greater, less than 4-fold greater, less than 5-fold greater, less than 6-fold greater, less than 7-fold greater, less than 8-fold greater, less than 9-fold greater, or less than 10-fold greater than the RBC hemolytic activity of the corresponding parent (i.e., unmodified) non-internally cross-linked peptide.

Pharmaceutically acceptable salts of the compounds of this disclosure include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include alkali metal (e.g., sodium), alkaline earth metal (e.g., magnesium), ammonium, and N-(alkyl)4+ salts. This disclosure also envisions the quaternization of any basic nitrogen-containing groups of the compounds disclosed herein. Water or oil-soluble or dispersible products may be obtained by such quaternization.

Pharmaceutical compositions of this disclosure can include one or more peptides and any pharmaceutically acceptable carrier and/or vehicle. In some instances, pharmaceuticals can further include one or more additional therapeutic agents in amounts effective for achieving a modulation of disease or disease symptoms.

When the compositions of this disclosure comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this disclosure. Alternatively, those agents may be part of a single dosage form, mixed together with the compounds of this disclosure in a single composition.

The term "pharmaceutically acceptable carrier or adjuvant" refers to a carrier or adjuvant that may be administered to a patient, together with a compound of this disclosure, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this disclosure include, but are not limited to, e.g., ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The addition of polyethylene glycol (PEG) moieties can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

XO—(CH2CH2O)n—CH2CH2—Y where n is 2 to 10,000 and X is H or a terminal modification, e.g., a C1-4 alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described, e.g., in WO 99/34833, WO 99/14259, and U.S. Pat. No. 6,348,558.

In certain aspects, macromolecular polymer (e.g., PEG) is attached to an agent described herein through an intermediate linker. In certain aspects, the linker is made up of from 1 to 20 amino acids linked by peptide bonds, wherein the amino acids are selected from the 20 naturally occurring amino acids. Some of these amino acids may be glycosylated, as is well understood by those in the art. In other aspects, the 1 to 20 amino acids are selected from glycine, alanine, proline, asparagine, glutamine, and lysine. In other aspects, a linker is made up of a majority of amino acids that are sterically unhindered, such as glycine and alanine. Non-peptide linkers are also possible. For example, alkyl linkers such as —NH(CH$_2$)nC(O)—, wherein n=2-20 can be used. These alkyl linkers may further be substituted by any non-sterically hindering group such as lower alkyl (e.g., C1-C6) lower acyl, halogen (e.g., Cl, Br), CN, NH2, phenyl, etc. U.S. Pat. No. 5,446,090 describes a bifunctional PEG linker and its use in forming conjugates having a peptide at each of the PEG linker termini.

The pharmaceutical compositions can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Materials and Methods

Solid Phase Peptide Synthesis

Fmoc-based solid-phase peptide synthesis was used to synthesize the antimicrobial peptides and their stapled derivatives. To achieve the various staple lengths, α-methyl, α-alkenyl amino acids were used flanking two, three, or six residues. The $R_5$ [(R)-2-(pentenyl)Ala-OH] residue was incorporated at position i and $S_5$ [(S)-2-(4-pentenyl)Ala-OH] at position i+3, while two $S_5$ residues were used at the i and i+4 locations, and an $R_8$ [(R)-2-(7-octenyl)Ala-OH] at position i and $S_5$ at i+7 [Bird et. al., Meth Enzymol., 446:369-386 (2008); Bird et al, Curr Protoc Chem Biol., 3(3):99-117 (2011). Alternative stapling amino acid couples can also be used to generate the corresponding staples (e.g., $R_8/S_5$ or $S_8$ [(S)-2-(7-octenyl)Ala-OH]/$R_5$ for i, i+3; $R_5/R_5$ or $S_5/S_5$ for i, i+4; $S_8/R_5$ or $R_8/S_5$ or i, i+7). As an example of how to, achieve a stitch in the scaffold, 2-amino-2-(pent-4-enyl)hept-6-enoic acid ($B_s$) was incorporated in the peptide sequence with a $S_5$ residue at the position i+3 before the $B_s$ residue and a $S_8$ residue at the i+7 position after the $B_s$ residue. For the stapling reaction, Grubbs first-generation ruthenium catalyst dissolved in dichloroethane was added to the peptides while still on resin. To ensure maximal conversion, three to five rounds of stapling were performed. Once stapled, the peptides were cleaved off the resin using trifluoroacetic acid, then precipitated using a hexane:ether (1:1) mixture, and afterwards they were air dried and purified using LC-MS. We performed amino acid analysis both to precisely determine the amount of peptide purified and to ensure the correct sequence was made.

Circular Dichroism Spectroscopy

Compounds were dissolved in an aqueous solution (e.g. 5 mM potassium phosphate solution at pH 7, or distilled $H_2O$, to concentrations of 25-50 µM). Circular dichroism (CD) spectra were obtained on a spectropolarimeter (Aviv) using standard measurement parameters (e.g., temperature, 37° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide was calculated by dividing the mean residue ellipticity by the reported value for a model helical decapeptide (see, e.g., Yang et al., Meth Enzymol. 130:208 (1986)).

Bacterial Specimens

StAMPs were screened against a panel of MDR clinical samples obtained from the Antimicrobial Resistance Isolate Bank of the Centers for Disease Control and Prevention (Atlanta, Ga.).

Antimicrobial Activity Assay

The following microbroth dilution protocol was adapted to determine the minimum inhibitory concentration (MIC) of each peptide. First, Mueller-Hinton broth (MHB) was passed through an anion exchange column to remove polyanionic species and generate refined MHB. This refined broth was then used in the standard microbroth dilution protocol devised by Hancock and coworkers for 96 well plates (note: No BSA was used in the protocol because initial studies revealed that it could interfere with peptide activity). Briefly, bacterial cells were grown overnight in refined MHB at 37° C. and then diluted and allowed to grow again for several hours. Serial dilutions of peptide stocks in water (10 µl) were prepared using clear round-bottom polypropylene 96-well plates. Then 90 µl of bacteria in refined MHB was added to give a final inoculum of $5 \times 10^5$ CFU/ml. The plates were then covered with porous tape to reduce evaporation, and incubated for 20-24 hours at 37° C. The MIC is the minimum peptide concentration at which no visible growth was observed.

Hemolytic Activity Assay

For the determination of hemolytic activity, human blood samples were centrifuged to isolate red blood cells (RBCs), which are then washed and suspended in phosphate-buffered saline to yield a 1% (v/v) suspension. The suspension was then added to serial dilutions of peptide stocks in water in clear round-bottom polypropylene 96-well plates and the plates were incubated for 1 hour at 37° C. After incubation, the plates were centrifuged and the supernatant was isolated to determine the amount of hemoglobin released using a spectrophotometer (570 nm), according to the equation: % Hemolysis=(Treated Absorbance−Untreated Control Absorbance)/(1% Triton-X100 Treated Absorbance−Untreated Control Absorbance). The minimum hemolytic concentration (MHC) is the peptide concentration at which there is less than 1% hemoglobin release.

Renal Toxicity Assay (Primary Human Renal Proximal Tubule Epithelial Cells (pRPTEC))

Briefly, pRPTECs in complete growth cell medium were seeded in a 96 well plate at a density of 10,000 cells per well and incubated at 37° C. for 48 hours. Complete medium was then removed and replaced with a toxicity assay medium to which various concentrations of StAMP were added. Cells were then further incubated for 24 to 48 hours after which cell medium was collected and assayed for the presence of Lactate Dehydrogenase (LDH) using a Cytotoxicity Detection Kit (LDH) (Roche).

Example 2: Synthesis of Stapled Magainin II Analogues

Magainin II is a well characterized AMP that was used as scaffold for the design of hydrocarbon-stapled and/or stitched anti-microbial peptides as described herein. A panel of stapled magainin II peptides and stapled pleurocidin peptides (e.g., Mag(i+4)1,15 (A9K), Mag(i+4)2,15 (A9K) and Pleu(i+4)1,15(A9K), Pleu(i+4)1,15) was previously generated (see, e.g., US. Patent Publication No. 2017/0015716 incorporated in its entirety herein).

Example 3: Hemolytic Activity of Stapled Magainin II Peptides and Pleurocidin Peptides Colistin resistance has been recently identified in clinical isolates of A. baumannii and E. coli. When these isolates were sequenced, it was found that A. baumannii acquired colistin resistance through either the complete loss of the negatively-charged lipid A, a component of the lipopolysaccharides (LPS) and the main binding target for colistin, or through the modification of lipid A with phosphoethanolamine. In the case of E. coli, it was discovered that the pathogen had acquired through horizontal gene transfer a plasmid-borne mobile colistin resistance gene (mcr-1), which encodes MCR-1, a phosphoethanolamine transferase enzyme that can modify lipid A. The emergence of these resistance mechanisms has gravely endangered our final antibiotic defense line, polymyxins. Cationic helical antimicrobial peptides (CHAMPs), like polymyxins, rely on the negatively charged membrane surface of bacteria for membrane binding and lysis. However, unlike polymyxins, CHAMPs are usually highly promiscuous and do not have a particular membrane target. Thus we hypothesized that hydrocarbon-stapled antimicrobial peptides (StAMPs) could be a viable option to treat colistin-resistant gram-negative pathogens.

To evaluate whether colistin-resistance results in cross-resistance with StAMPs, we selected three lead compounds that displayed potent antimicrobial activity and low hemolytic activity: Mag(i+4)1,15 (A9K) (SEQ ID NO:1), Mag(i+4)2,15 (A9K) (SEQ ID NO:2), and Pleu(i+4)1,15 (A9K) (SEQ ID NO:3) and one compound, Pleu(i+4)1,15 (SEQ ID NO:34) with potent antimicrobial activity and high hemolytic activity (Table 2).

where "X" represents (S)-2-(4-pentenyl)Ala-OH olefinic residues. The sequence of Pleu(i+4)1,15, that was used in this study is GXGSFXKKAAHVGKHXGKAXLTHYL where "X" represents (S)-2-(4-pentenyl)Ala-OH olefinic residues.

Example 4: Antimicrobial Activity of Stapled Magainin II Peptides and Pleurocidin Peptides The first three StAMPs of Table 2 in Example 3 were then tested against 39 clinical isolates of *A. baumannii* with

TABLE 2

Hemolytic Activity of StAMPs

| Peptide ID | Sequence | % Hemolysis at 25 µg/ml |
|---|---|---|
| Mag(i+4)1,15(A9K) | GXGKFXHSKKKFGKAXVGEXBNS | 1.9 |
| Mag(i+4)2,15(A9K) | GIXKFLXSKKKFGKAXVGEXBNS | 17.9 |
| Pleu(i+4)1,15(A9K) | GXGSFXKKKAHVGKHXGKAXLTHYL | 16.3 |
| Pleu(i+4)1,15 | GXGSFXKKAAHVGKHXGKAXLTHYL | 88.2 |

The peptides in Table 2 are SEQ ID Nos.: 1-3 and 34, numbered consecutively from top to bottom. The sequence of Mag(i+4)1,15(A9K) (SEQ ID NO: 1) that was used in this study is GXGKFXHSKKKFGKAXVGEXBNS where "X" represents (S)-2-(4-pentenyl)Ala-OH olefinic residues and "B" is norleucine; the sequence of Mag(i+4)2,15(A9K) (SEQ ID NO: 2) that was used in this study is GIXKFLXSKKKFGKAXVGEXBNS where "X" represents (S)-2-(4-pentenyl)Ala-OH olefinic residues and "B" is norleucine; the sequence of Pleu(i+4)1,15(A9K) that was used in this study is GXGSFXKKKAHVGKHXGKAXLTHYL various degrees of colistin resistance (Table 3, 4). The StAMPs displayed potent activity against all the strains tested regardless of their colistin resistance pattern, proving that StAMPs' promiscuous mechanism of action allows them to circumvent simple lipid modifications. As further proof that these results are not species specific, we tested our compounds against two *E. coli* clinical isolates that harbor the MCR-1 plasmid and found similar potencies (Table 4).

TABLE 3

Minimum Inhibitory Concentration (MIC) of Mag(i+4)1,15 (A9K), Mag(i+4)2,15 (A9K) and Pleu(i+4)1,15(A9K)) peptides in *A. baumannii* clinical isolates

| CDC Bank# | Organism | Antimicrobial Activity MIC (µg/ml) | | | |
|---|---|---|---|---|---|
| | | Mag(i+4)1,15(A9K) | Mag(i+4)2,15(A9K) | Pleu(i+4)1,15(A9K) | Colistin |
| 275 | A. baumannii | 1.6 | 3.1 | 1.6 | 1 |
| 276 | A. baumannii | 1.6 | 1.6 | 1.6 | 2 |
| 277 | A. baumannii | 1.6 | 1.6 | 1.6 | 1 |
| 278 | A. baumannii | 1.6 | 3.1 | 3.1 | 1 |
| 279 | A. baumannii | 1.6 | 2.2 | 1.6 | 1 |
| 280 | A. baumannii | 1.6 | 1.6 | 3.1 | 1 |
| 281 | A. baumannii | 2.2 | 1.6 | 2.2 | 1 |
| 282 | A. baumannii | 1.6 | 1.6 | 1.6 | 0.5 |
| 283 | A. baumannii | 2.2 | 2.2 | 2.2 | 1 |
| 284 | A. baumannii | 1.6 | 2.2 | 1.6 | 1 |
| 285 | A. baumannii | 1.6 | 1.6 | 1.6 | 1 |
| 286 | A. baumannii | 1.6 | 2.2 | 3.1 | 0.5 |
| 287 | A. baumannii | 1.6 | 1.6 | 3.1 | 1 |
| 288 | A. baumannii | 3.1 | 1.6 | 1.6 | >8 |
| 289 | A. baumannii | 1.6 | 1.6 | 1.6 | 2 |
| 290 | A. baumannii | 1.6 | 2.2 | 1.6 | 1 |
| 291 | A. baumannii | 3.1 | 3.1 | 2.2 | 1 |
| 292 | A. baumannii | 1.6 | 1.6 | 2.2 | 1 |
| 293 | A. baumannii | 1.6 | 1.6 | 1.6 | 0.5 |
| 294 | A. baumannii | 1.6 | 1.6 | 1.6 | 1 |
| 295 | A. baumannii | 1.6 | 2.2 | 3.1 | 1 |
| 296 | A. baumannii | 1.6 | 1.6 | 2.2 | 0.5 |
| 297 | A. baumannii | 1.6 | 1.6 | 2.2 | 1 |
| 298 | A. baumannii | 1.6 | 1.6 | 1.6 | 0.5 |
| 299 | A. baumannii | 1.6 | 1.6 | 1.6 | 2 |
| 300 | A. baumannii | 1.6 | 1.6 | 2.2 | 1 |
| 301 | A. baumannii | 1.6 | 1.6 | 2.2 | 0.5 |

TABLE 3-continued

Minimum Inhibitory Concentration (MIC) of Mag(i+4)1,15 (A9K), Mag(i+4)2,15
(A9K) and Pleu(i+4)1,15(A9K)) peptides in *A. baumannii* clinical isolates

| CDC Bank# | Organism | Antimicrobial Activity MIC (µg/ml) | | | |
|---|---|---|---|---|---|
| | | Mag(i+4)1,15(A9K) | Mag(i+4)2,15(A9K) | Pleu(i+4)1,15(A9K) | Colistin |
| 302 | A. baumannii | 1.6 | 1.6 | 1.6 | 2 |
| 303 | A. baumannii | 3.1 | 1.6 | 1.6 | >8 |
| 304 | A. baumannii | 1.6 | 1.6 | 1.6 | 4 |
| 305 | A. baumannii | 1.6 | 1.6 | 1.6 | 1 |
| 306 | A. baumannii | 1.6 | 1.6 | 1.6 | 1 |

TABLE 4

Minimum Inhibitory Concentration (MIC) of Mag(i+4)1,15 (A9K), Mag(i+4)2,15 (A9K)
and Pleu(i+4)1,15(A9K)) peptides in *A. baumannii* and *E. coli* clinical isolates

| CDC Bank# | Organism | Antimicrobial Activity MIC (µg/ml) | | | |
|---|---|---|---|---|---|
| | | Mag(i+4)1,15(A9K) | Mag(i+4)2,15(A9K) | Pleu(i+4)1,15(A9K) | Colistin |
| 307 | A. baumannii | 1.6 | 2.2 | 2.2 | >8 |
| 308 | A. baumannii | 1.6 | 1.6 | 1.6 | 8 |
| 309 | A. baumannii | 1.6 | 1.6 | 2.2 | 8 |
| 310 | A. baumannii | 1.6 | 1.6 | 1.6 | 8 |
| 311 | A. baumannii | 1.6 | 1.6 | 1.6 | 1 |
| 312 | A. baumannii | 1.6 | 1.6 | 1.6 | 0.5 |
| 313 | A. baumannii | 1.6 | 1.6 | 1.6 | 1 |
| 346 | E. coli* | 1.6 | 2.2 | 1.6 | 2.5 |
| 349 | E. coli* | 3.1 | 3.1 | 1.6 | 1.2 |

*Contain MCR-1 plasmid

Example 5: Antimicrobial Activity of Stapled Magainin II Peptides and Pleurocidin Peptides StAMPs Mag(i+4)2,15(A9K), Pleu(i+4)1,15(A9K) and Pleu(i+4)1,15 were also then tested against 4 clinical isolates of *S. aureus* of which two were methicillin-susceptible (MSSA) and two were methicillin-resistant (MRSA) (Table 5). The StAMPs displayed potent activity against all the strains tested regardless of their susceptibility to methicillin, proving that StAMPs' spectrum of activity can be extended to gram-positive organisms regardless of their resistance pattern as well.

TABLE 5

Minimum Inhibitory Concentration (MIC) of Mag(i+4)2,15 (A9K),
Pleu(i+4)1,15 (A9K) and Pleu(i+4)1,15 peptides in Methicillin-
susceptible and Methicillin-resistant *S. aureus* clinical isolates

| Sample ID | Organism | Antimicrobial Activity MIC (µg/ml) | | |
|---|---|---|---|---|
| | | Mag(i+4)2,15 (A9K) | Pleu(i+4)1,15 (A9K) | Pleu(i+4)1,15 |
| RB003 | Methicillin-susceptible S Aureus | 1.6 | 3.1 | 3.1 |
| RB006 | Methicillin-susceptible S Aureus | 1.6 | 3.1 | 3.1 |
| RB004 | Methicillin-resistant S Aureus | 1.6 | 3.1 | 3.1 |
| RB007 | Methicillin-resistant S Aureus | 1.6 | 3.1 | 3.1 |

Example 6: Renal Toxicity of Stapled Antimicrobial Peptides (StAMPs)

Many cationic antibiotics such as colistin, polymyxin b, and gentamicin that are in current clinical use cause nephrotoxicity over the course of treatment, thereby limiting the duration of use in patients and the doses that can be administered. Likewise, antimicrobial peptides (AMPs) have shown a similar toxicity profile to colistin and polymyxin b, and may cause damage to kidney cells in the proximal convoluted tubule. However, very little research has been conducted to reduce the potential nephrotoxicity of AMPs, likely because most AMPs are being developed clinically for topical use only, so as to avoid the documented challenges and limitations of internal administration.

As described in the Examples above, stapled antimicrobial peptides (StAMPs) with high antimicrobial activity and little to no hemolytic activity can be generated using hydrocarbon stapling. However, when the toxicity of Mag(i+4)1, 15(A9K) was tested on primary human renal proximal tubule epithelial cells (pRPTECs), we discovered that it could cause membranolysis of pRPTECs at relatively low concentrations. It is plausible that the pRPTEC assay is especially sensitive, and does not reflect the toxicity of StAMPs in vivo accurately. All the same, these results prompted us to re-engineer Mag(i+4)1,15(A9K) to reduce potential kidney cell lytic properties while maintaining strong antimicrobial activity. We explored two approaches to mitigate pRPTEC lysis to reduce the potential renal toxicity of AMPs.

First, we altered the cationic point charges of a StAMP in an attempt to reduce pRPTEC lysis. One of the main determinants of renal proximal tubule toxicity of colistin, a cationic lipopeptide, is the number of cationic point charges. By masking the point charges on colistin using methanesulfate, a labile protecting group, colistin's renal toxicity profile has been drastically improved and colistin methanesulfate has become the main formulation that is used clinically. Since the cationic charges on Mag(i+4)1,15(A9K) are also point charges, we evaluated whether changing the charge nature would result in a significant reduction in renal toxicity. To that end, we synthesized Mag(i+4)1,15(A9K) analogues that each had one or more amino acid substitutions, wherein we substituted at least one lysine residue with at least one of either an arginine (a delocalized cationic charge) or a histidine (a cationic charged residue that becomes mostly protonated at a pH below 6). The Mag(i+4)1,15 (A9K) analogues with altered cationic point charges are shown in Table 6.

TABLE 6

Mag(i+4)1,15(A9K) Analogues with Altered Cationic Point Charges

| Peptide ID | Sequence* | SEQ ID NO: |
|---|---|---|
| Mag(i+4)1,15(A9K) | GXGKFXHSKKKFGKAXVGEXBNS | SEQ ID NO: 1 |
| Mag(i+4)1,15(A9K, K4H) | GXGHFXHSKKKFGKAXVGEXBNS | SEQ ID NO: 36 |
| Mag(i+4)1,15(A9K, K4H, K10H) | GXGHFXHSKHKFGKAXVGEXBNS | SEQ ID NO: 37 |

TABLE 6-continued

Mag(i+4)1,15(A9K) Analogues with Altered Cationic Point Charges

| Peptide ID | Sequence* | SEQ ID NO: |
|---|---|---|
| Mag(i+4)1,15(A9K, K4H, K10H, K11H) | GXGHFXHSKHHFGKAXVGEXBNS | SEQ ID NO: 38 |
| Mag(i+4)1,15(A9K, K4R) | GXGRFXHSKKKFGKAXVGEXBNS | SEQ ID NO: 39 |
| Mag(i+4)1,15(A9K, K4R, K10R) | GXGRFXHSKRKFGKAXVGEXBNS | SEQ ID NO: 40 |

*Where a bolded "X" represents an (S)-2-(4-pentenyl)Ala-OH olefinic residue, and a bolded and underlined residue represents an amino acid substitution introduced to reduce renal toxicity The new analogues with altered cationic charges (Table 6) displayed less potent minimum inhibitory concentration (MIC) values, as compared to Mag(i+4)1,15(A9K), when tested against various bacterial pathogens. As shown in Table 7, substituting lysines with arginines resulted in an only one dilution step decrease in MIC, while substituting lysines with histidines resulted in a stepwise decrease in MIC potency, such that potency decreased as more lysines were substituted with histidines. As shown in FIG. 1, the Mag(i+4)1,15(A9K) analogues of Table 6 displayed significantly attenuated pRPTEC lytic activity after a 24-hour incubation. Thus, changing the charge nature of Mag(i+4) 1,15(A9K) significantly attenuated its lytic activity in a pRPTEC toxicity assay. Lysine to arginine substitutions resulted in reduced pRPTEC lysis, while lysine to histidine substitutions resulted in a more significant decrease in pRPTEC lysis. Overall, these results showed that altering cationic point charges decreased pRPTEC lysis, but also resulted in a concomitant decrease in peptide antimicrobial activity. Thus, changing the charge nature achieved the desired effect of mitigating pRPTEC lysis, but does not necessarily provide a wider therapeutic window.

TABLE 7

Minimum Inhibitory Concentrations of Mag(i+4)1,15(A9K) Analogues with Altered Cationic Point Charges

| | MIC (µg/ml) | | | | |
|---|---|---|---|---|---|
| Peptide Name | E coli | B cereus | P aeruginosa | S aureus | A baumannii |
| Mag(i+4)1,15(A9K) | 1.6 | 6.2 | 3.1 | 50 | 1.6 |
| Mag(i+4)1,15(A9K, K4H) | 3.1 | 25 | 6.2 | >50 | N.D |
| Mag(i+4)1,15(A9K, K4H, K10H) | 3.1 | 50 | 50 | >50 | N.D |
| Mag(i+4)1,15(A9K, K4H, K10H, K11H) | 17.7 | >50 | 50 | >50 | N.D |
| Mag(i+4)1,15(A9K, K4R) | 3.1 | 12.5 | 6.2 | >50 | N.D |
| Mag(i+4)1,15(A9K, K4R, K10R) | 3.1 | 12.5 | 6.2 | >50 | N.D |

N.D = Not Determined

In a second approach, we altered the hydrophobicity of a StAMP in an attempt to reduce pRPTEC lysis. When we delineated the design rules for selective StAMPs, one of the main factors that determined StAMP hemolytic activity was the presence of continuous hydrophobic patches. Disrupting the continuity of hydrophobic patches had reduced unwanted hemolytic activity while resulting in little to no reduction in antimicrobial activity. Thus, we mutated the norleucine residue in Mag(i+4)1,15(A9K) to an alanine residue (Mag(i+4)1,15(A9K)(B21A)) to determine if a further reduction in hydrophobicity in one of the two patches of Mag(i+4)1,15(A9K) would result in decreased pRPTEC lysis. (see Table 8). The first hydrophobic patch of Mag(i+4)1,15(A9K) is made up of the X2, X6, and F5 residues, while the second hydrophobic patch is made up of the F12, X16, V17, X20, and B21 residues. As shown in Table 8, we also produced two other novel Mag(i+4)1,15(A9K) analogues, Mag(i+4)1,15(A9K) (B21K) and Mag(i+4)1,15 (A9K)(B21A,N22K,S23K), to test whether making StAMPs more cationic on the hydrophilic face, and thus increasing their affinity for bacterial membranes, could compensate for any decrease in antibiotic activity that could result from lowering patch hydrophobicity.

TABLE 8

Mag(i+4)1,15(A9K) Analogues with Altered Hydrophobicity

| Peptide ID | Sequence* | SEQ ID NO: |
|---|---|---|
| Mag(i+4)1,15 (A9K) | GXGKFXHSKKKFGKAXVGEXBNS | SEQ ID NO: 1 |
| Mag(i+4)1,15 (A9K, B21A) | GXGKFXHSKKKFGKAXVGEXANS | SEQ ID NO: 41 |
| Mag(i+4)1,15 (A9K, B21K) | GXGKFXHSKKKFGKAXVGEXKNS | SEQ ID NO: 42 |

TABLE 8-continued

Mag(i+4)1,15(A9K) Analogues with Altered Hydrophobicity

| Peptide ID | Sequence* | SEQ ID NO: |
|---|---|---|
| Mag(i+4)1,15 (A9K, B21A, N22K, S23K) | GXGKFXHSKKKFGKAXVGEXAKK | SEQ ID NO: 43 |

*Where a bolded "X" represents an (S)-2-(4-pentenyl)Ala-OH olefinic residue, and a bolded and underlined residue represents an amino acid substitution introduced to reduce renal toxicity As shown in FIG. 1, the Mag(i+4)1,15(A9K)(B21A) peptide, when tested, displayed significantly attenuated pRPTEC lysis relative to Mag(i+4)1,15(A9K), after a 24 hour incubation. However, as shown in Table 9, Mag(i+4)1,15(A9K)(B21A) also displayed reduced antimicrobial activity (had reduced MIC values) against various bacterial pathogens, as compared to Mag(i+4)1,15(A9K). Thus, peptide hydrophobic interactions play an important role in the lysis of pRPTECs, which are more sensitive to lysis than RBCs. Reducing the hydrophobicity of StAMP hydrophobic patches decreases pRPTEC lysis.

Figure 2:
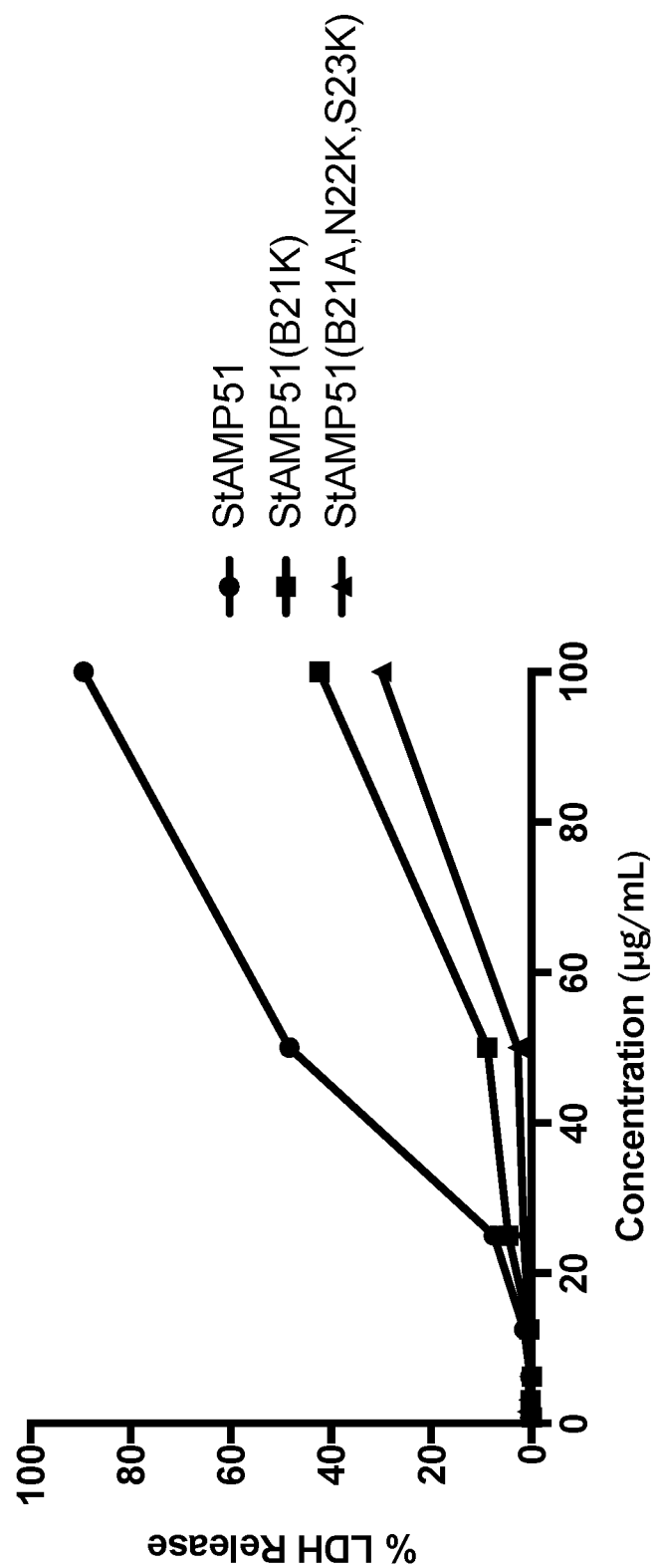
FIG. 2 depicts levels of pRPTEC lysis following a 90-minute incubation with increasing concentrations of Mag (i+4)1,15(A9K) (SEQ ID NO: 1) or an analogue of Mag(i+4)1,15(A9K) (SEQ ID Nos.: 42-43), as measured using a lactate dehydrogenase (LDH) release assay (% LDH release).

As shown in FIG. 2, the Mag(i+4)1,15(A9K)(B21K) and Mag(i+4)1,15(A9K)(B21A, N22K, S23K) peptides also displayed markedly reduced lytic activity toward pRPTECs, when compared to Mag(i+4)1,15(A9K), after a 90 minute incubation. FIG. 3 shows that these peptides also lowered long-term lytic activity when incubated with pRPTECs for 48 hours. As shown in Table 9, Mag(i+4)1,15(A9K)(B21K) displayed a similar antimicrobial potency to Mag(i+4)1,15 (A9K)(B21A) when tested against gram-negative pathogens, while Mag(i+4)1,15(A9K)(B21A,N22K,S23K) had a similar antimicrobial potency as Mag(i+4)1,15(A9K) and displayed higher selectivity toward gram-negative pathogens. These results confirm that the degree of hydrophobicity in the hydrophobic patches of StAMPs can be adjusted to reduce toxicity to pRPTECs and reduce lysis. Should any of the changes to hydrophobic patches decrease the potency of StAMP antibiotic activity, the antibiotic activity can be reestablished or enhanced by increasing the number of positively-charged residues, such as lysines, to the hydrophilic face of the helix via mutation.

TABLE 9

Minimum Inhibitory Concentrations of Mag(i+4)1,15(A9K) Analogues with Altered Hydrophobicity

| Peptide Name | MIC (µg/ml) | | | | |
|---|---|---|---|---|---|
| | E coli | B cereus | P aeruginosa | S aureus | A baumannii |
| Mag(i+4)1,15(A9K) | 1.6 | 6.2 | 3.1 | 50 | 1.6 |
| Mag(i+4)1,15(A9K, B21A) | 6.2 | 50 | 8.8 | >50 | N.D |
| Mag(i+4)1,15(A9K, B21K) | 3.1 | 35.4 | 12.5 | >50 | 1.6 |
| Mag(i+4)1,15(A9K, B21A, N22K, S23K) | 1.6 | 50 | 3.1 | >50 | 0.8 |

N.D = Not Determined

Example 7: Effectiveness of StAMPS Against Carbapenem-Resistant Bacteria

Carbapenems are an essential line of antibiotics in our armamentarium that are commonly used to treat a wide array of Gram-positive and Gram-negative pathogens. Despite being part of the beta-lactamase family of antibiotics, the carbapenem moiety present next to the beta-lactam ring of these drugs confers remarkable stability against beta-lactamases and extended spectrum beta-lactamases, making them a drug of choice when doctors are faced with suspected multi-drug resistant (MDR) pathogens. Nevertheless, the widespread use of this class of antibiotics has led to an increase in the prevalence of carbapenem-resistance amongst Gram-positive and Gram-negative pathogens alike. While there are some viable treatment options for Gram-positives, such as daptomycin and vancomycin, the treatment options for carbapenem-resistant Gram-negative pathogens are severely limited. Thus it is of high priority that new therapeutics are developed that can circumvent carbapenem resistance in Gram-negative bacteria.

To that end, the new class of antibiotics described herein—stapled antimicrobial peptides (StAMPs)—were tested against a range of Enterobacteriaceae clinical samples with variable resistance against carbapenems, exemplified here by their sensitivity to meropenem (Mero). See, FIG. 4.

Across various species including *E. coli, K. pneumoniae*, and *Salmonella*, the compounds described herein displayed antimicrobial efficacies in the range of 0.78 to 12.5 µg/mL, underscoring that sensitivity to the promiscuous StAMP mechanism of action is not affected by the various carbapenem mechanisms of resistance used by Gram-negative pathogens such as the expression of carbapenemases, like KPC-3 (expressed in strains 0001, 0002, 0112, and 0114) and truncation of porins needed for carbapenem diffusion into the periplasm (found in strains 0006 and 0113).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patent applications, patents, and other publications cited herein are incorporated by reference in their entireties.

What is claimed is:

1. A stapled peptide or pharmaceutically acceptable salt thereof comprising the amino acid sequence: GX$_1$GKFX$_2$HSKKKFGKAX$_3$VGEX$_4$AKK (SEQ ID NO:43), wherein each of X$_1$, X$_2$, X$_3$, and X$_4$ is a non-natural amino acid; wherein X$_1$ and X$_2$ are cross-linked to each other; and wherein X$_3$ and X$_4$ are cross-linked to each other.

2. The stapled peptide or pharmaceutically acceptable salt thereof of claim 1, wherein each of X$_1$, X$_2$, X$_3$, and X$_4$ is independently an α, α-disubstituted non-natural amino acid comprising an olefinic side chain.

3. The stapled peptide or pharmaceutically acceptable salt thereof of claim 1, wherein each of X$_1$, X$_2$, X$_3$, and X$_4$ is (S)-2-(4-pentenyl)Ala-OH.

4. A pharmaceutical composition comprising the stapled peptide or pharmaceutically acceptable salt thereof of claim 3, and a pharmaceutically acceptable carrier.

5. The stapled peptide or pharmaceutically acceptable salt thereof of claim 1, wherein the stapled peptide is between 23 and 30 amino acids in length, inclusive.

6. A pharmaceutical composition comprising the stapled peptide or pharmaceutically acceptable salt thereof of claim 1, and a pharmaceutically acceptable carrier.

7. A stapled peptide or pharmaceutically acceptable salt thereof consisting of the amino acid sequence: GX$_1$GKFX$_2$HSKKKFGKAX$_3$VGEX$_4$AKK (SEQ ID NO:43), wherein each of X$_1$, X$_2$, X$_3$, and X$_4$ is (S)-2-(4-pentenyl)Ala-OH; wherein X$_1$ and X$_2$ are cross-linked to each other; and wherein X$_3$ and X$_4$ are cross-linked to each other.

8. The stapled peptide or pharmaceutically acceptable salt thereof of claim 1, wherein the stapled peptide is modified by acetylation, PEGylation, amidation, and/or modification with a fatty acid chain.

9. A pharmaceutical composition comprising the stapled peptide or pharmaceutically acceptable salt thereof of claim 7, and a pharmaceutically acceptable carrier.

10. A method of treating a bacterial infection in a subject in need thereof, the method comprising: administering a therapeutically effective amount of the stapled peptide or pharmaceutically acceptable salt thereof of claim 1 to the subject.

11. The method of claim 10, wherein the bacterial infection is a Gram-positive bacterial infection.

12. The method of claim 10, wherein the bacterial infection is a Gram-negative bacterial infection.

13. The method of claim 10, wherein the bacterial infection is an *E. coli* infection, a *K. pneumonia* infection, a *Salmonella* infection, an *Enterobacter cloacae* infection, a *Shigella* infection, a *B. cereus* infection, a *P. aeruginosa* infection, a *S. aureus* infection, or an *A. baumannii* infection.

14. The method of claim 10, wherein the bacterial infection is an antibiotic-resistant bacterial infection.

15. The method of claim 14, wherein the antibiotic-resistant bacterial infection is a Gram-negative colistin-resistant bacterial infection or a Gram-positive carbapenem-resistant bacterial infection.

16. The method of claim 14, wherein the antibiotic-resistant bacterial infection is an *Actinomyces israelii* infection, an *Actinomyces gerencseriae* infection, a *Propionibacterium* propionicus infection, a *Bacillus anthracis* infection, an *Arcanobacterium haemolyticum* infection, a *Bacillus cereus* infection, a bacterial vaginosis microbiota infection, a *Clostridium botulinum* infection, a *Mycobacterium ulcerans* infection, a Group A *Streptococcus* or *Staphylococcus* infection, a *Clostridium* species infection, a *Corynebacterium diphtheria* infection, an *Enterococcus* species infection, a *Streptococcus pyogenes* infection, a *Streptococcus agalactiae* infection, a *Mycobacterium leprae* infection, a *Mycobacterium* lepromatosis infection, a *Listeria monocytogenes* infection, a *Nocardia* species infection, a *Streptococcus pneumonia* infection, a *Staphylococcus* species infection, a *Mycobacterium tuberculosis* infection, a *Yersinia pseudotuberculosis* infection, or a *Yersinia enterocolitica* infection.

17. The method of claim 14, wherein the antibiotic-resistant bacterial infection is a *Pseudomonas aeruginosa* infection, a *Neisseria gonorrhoeae* infection, a *Chlamydia trachomatis* infection, a *Yersinia pestis* infection, a *Proteus mirabilis* infection, an *Enterobacter cloacae* infection, a *Serratia marcescens* infection, a *Helicobacter pylori* infection, a *Salmonella enteritidis* infection, a *Salmonella typhi* infection, a *Shigella* infection, a *Moraxella* infection, a *Stenotrophomonas* infection, a *Bdellovibrio* infection, an acetic acid bacterial infection, a *Klebsiella pneumoniae* infection, a *Legionella pneumophila* infection, an *A. baumannii* infection, an *E. coli* infection, or an *Enterobacter* infection.

18. The method of claim 10, wherein the subject is a human.

19. The method of claim 10, wherein the subject is an animal.

20. A method of killing or inhibiting the growth of a bacterium, the method comprising contacting the bacterium with the stapled peptide or pharmaceutically acceptable salt thereof of claim 1.

21. The method of claim 20, wherein the bacterium is an antibiotic-resistant bacterium.

22. The method of claim 20, wherein the contacting is in vitro.

23. The method of claim 20, wherein the contacting is in vivo.

24. A method of treating a bacterial infection in a subject in need thereof, the method comprising: administering a therapeutically effective amount of the stapled peptide or pharmaceutically acceptable salt thereof of claim 7 to the subject.

25. A method of making a stapled peptide or pharmaceutically acceptable salt thereof, the method comprising:
   (a) providing a peptide comprising the amino acid sequence: GX$_1$GKFX$_2$HSKKKFGKAX$_3$VGEX$_4$AKK (SEQ ID NO:43), or pharmaceutically acceptable salt thereof, wherein each of $X_1$, $X_2$, $X_3$, and $X_4$ is an α,α-disubstituted non-natural amino acid comprising an olefinic side chain; and (b) performing a ring-closing metathesis reaction on the peptide, thereby making the stapled peptide or pharmaceutically acceptable salt thereof.

26. The method of claim 25, further comprising formulating the stapled peptide or pharmaceutically acceptable salt thereof as a sterile pharmaceutical composition.

27. The method of claim 24, wherein the subject is an animal.

28. The method of claim 27, wherein the subject is a human.

29. A method of killing or inhibiting the growth of a bacterium, the method comprising contacting the bacterium with the stapled peptide or pharmaceutically acceptable salt thereof of claim 7.

30. The method of claim 29, wherein the subject is a human.

31. The method of claim 29, wherein the subject is an animal.

* * * * *

UNITED STATES PATENT AND TRADEMARK OFFICE
CERTIFICATE OF CORRECTION

| | |
|---|---|
| PATENT NO. | : 11,325,955 B2 |
| APPLICATION NO. | : 16/631315 |
| DATED | : May 10, 2022 |
| INVENTOR(S) | : Loren D. Walensky and Rida Mourtada |

It is certified that error appears in the above-identified patent and that said Letters Patent is hereby corrected as shown below:

In the Claims

Column 129, Line 12:
In Claim 28, delete "claim 27," and insert -- claim 24, --.

Signed and Sealed this
Thirtieth Day of August, 2022

Katherine Kelly Vidal
*Director of the United States Patent and Trademark Office*

SEQUENCE LISTING

```
<160> NUMBER OF SEQ ID NOS: 43

<210> SEQ ID NO 1
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 1

Gly Xaa Gly Lys Phe Xaa His Ser Lys Lys Lys Phe Gly Lys Ala Xaa
1               5                   10                  15

Val Gly Glu Xaa Xaa Asn Ser
            20

<210> SEQ ID NO 2
<211> LENGTH: 23
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any non-natural amino acid
<220> FEATURE:
<221> NAME/KEY: MOD_RES
<222> LOCATION: (7)..(7)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 2

Gly Ile Xaa Lys Phe Leu Xaa Ser Lys Lys Lys Phe Gly Lys Ala Xaa
1               5                   10                  15

Val Gly Glu Xaa Xaa Asn Ser
            20

<210> SEQ ID NO 3
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: source
<223> OTHER INFORMATION: /note="See specification as filed for detailed
      description of substitutions and preferred embodiments"

<400> SEQUENCE: 3

Gly Xaa Gly Ser Phe Xaa Lys Lys Lys Ala His Val Gly Lys His Xaa
1               5                   10                  15

Gly Lys Ala Xaa Leu Thr His Tyr Leu
            20                  25

<210> SEQ ID NO 4
<211> LENGTH: 23
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 5
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 6
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 7
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (19)..(19)
<223> OTHER INFORMATION: Any non-natural amino acid

<400> SEQUENCE: 7

Gly Trp Gly Ser Phe Phe Lys Lys Ala Ala His Xaa Gly Lys His Val
1               5                   10                  15

Gly Lys Xaa Ala Leu Thr His Tyr Leu
            20                  25

<210> SEQ ID NO 8
```

```
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu

<210> SEQ ID NO 9
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (19)..(19)
<223> OTHER INFORMATION: Any non-natural amino acid

<400> SEQUENCE: 9

Gly Phe Phe Ala Leu Ile Pro Lys Ile Ile Ser Xaa Pro Leu Phe Lys
1               5                   10                  15

Thr Leu Xaa Ser Ala Val Gly Ser Ala Leu Ser Ser Ser Gly Glu Gln
            20                  25                  30

Glu

<210> SEQ ID NO 10
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gly Phe Phe Lys Lys Ala Trp Arg Lys Val Lys His Ala Gly Arg Arg
1               5                   10                  15

Val Leu Lys Lys Gly Val Gly Arg His Tyr Val Asn Asn Trp Leu Lys
            20                  25                  30

<210> SEQ ID NO 11
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
```

```
<222> LOCATION: (21)..(21)
<223> OTHER INFORMATION: Any non-natural amino acid

<400> SEQUENCE: 11

Gly Phe Phe Lys Lys Ala Trp Arg Lys Val Lys His Ala Xaa Arg Arg
1               5                   10                  15

Val Leu Lys Lys Xaa Val Gly Arg His Tyr Val Asn Asn Trp Leu Lys
            20                  25                  30

<210> SEQ ID NO 12
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Val Leu Ser Asn Val Ile Gly Tyr Leu Lys Lys Leu Gly Thr Gly
1               5                   10                  15

Ala Leu Asn Ala Val Leu Lys Gln
            20

<210> SEQ ID NO 13
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid

<400> SEQUENCE: 13

Gly Val Leu Ser Asn Val Ile Gly Tyr Leu Lys Lys Leu Xaa Thr Gly
1               5                   10                  15

Ala Leu Asn Ala Xaa Leu Lys Gln
            20

<210> SEQ ID NO 14
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Thr Arg Ser Ser Arg Ala Gly Leu Gln Phe Pro Val Gly Arg Val His
1               5                   10                  15

Arg Leu Leu Arg Lys
            20

<210> SEQ ID NO 15
<211> LENGTH: 21
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (19)..(19)
<223> OTHER INFORMATION: Any non-natural amino acid

<400> SEQUENCE: 15

Thr Arg Ser Ser Arg Ala Gly Leu Gln Phe Pro Xaa Gly Arg Val His
1               5                   10                  15

Arg Leu Xaa Arg Lys
            20

<210> SEQ ID NO 16
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 17
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid

<400> SEQUENCE: 17

Ala Leu Trp Lys Thr Met Leu Lys Lys Leu Gly Thr Met Xaa Leu His
1               5                   10                  15

Ala Gly Lys Ala Xaa Leu Gly Ala Ala Ala Asp Thr Ile Ser Gln Gly
            20                  25                  30

Thr Gln

<210> SEQ ID NO 18
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Leu Phe Lys Val Leu Gly Ser Val Ala Lys His Leu Pro His
1               5                   10                  15

Val Val Pro Val Ile Ala Glu Lys Leu
            20                  25

<210> SEQ ID NO 19
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid

<400> SEQUENCE: 19

Gly Leu Phe Lys Val Leu Gly Ser Val Ala Lys His Leu Xaa Pro His
1               5                   10                  15

Val Val Pro Val Xaa Ala Glu Lys Leu
            20                  25

<210> SEQ ID NO 20
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 21
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (13)..(13)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid

<400> SEQUENCE: 21

Gly Ile Gly Ala Val Leu Lys Val Leu Thr Thr Gly Xaa Pro Ala Leu
1               5                   10                  15

Ile Ser Trp Xaa Lys Arg Lys Arg Gln Gln
            20                  25

<210> SEQ ID NO 22

```
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 23
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: MOD_RES
<222> LOCATION: (11)..(11)
<223> OTHER INFORMATION: Any non-natural amino acid

<400> SEQUENCE: 23

Lys Trp Lys Xaa Phe Lys Lys Ile Glu Lys Xaa Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 24
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Lys Ile Lys Trp Phe Lys Thr Met Lys Ser Ile Ala Lys Phe Ile Ala
1               5                   10                  15

Lys Glu Gln Met Lys Lys His Leu Gly Gly Glu
            20                  25

<210> SEQ ID NO 25
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Any non-natural amino acid
```

```
<220> FEATURE:
<221> NAME/KEY: MOD_RES
<222> LOCATION: (15)..(15)
<223> OTHER INFORMATION: Any non-natural amino acid

<400> SEQUENCE: 25

Lys Ile Lys Trp Phe Lys Thr Xaa Lys Ser Ile Ala Lys Phe Xaa Ala
1               5                   10                  15

Lys Glu Gln Met Lys Lys His Leu Gly Gly Glu
            20                  25

<210> SEQ ID NO 26
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Phe Gly Pro Ala Phe His Ser Val Ser Asn Phe Ala Lys Lys His
1               5                   10                  15

Lys Thr Ala

<210> SEQ ID NO 27
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 27

Gly Phe Gly Pro Xaa Phe His Ser Val Ser Asn Xaa Ala Lys Lys His
1               5                   10                  15

Lys Thr Ala

<210> SEQ ID NO 28
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Val Phe Gln Phe Leu Gly Arg Ile Ile His His Val Gly Asn Phe Val
1               5                   10                  15

His Gly Phe Ser His Val Phe
            20

<210> SEQ ID NO 29
<211> LENGTH: 23
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: MOD_RES
<222> LOCATION: (12)..(12)
<223> OTHER INFORMATION: Any non-natural amino acid

<400> SEQUENCE: 29

Val Phe Gln Phe Xaa Gly Arg Ile Ile His His Xaa Gly Asn Phe Val
1               5                   10                  15

His Gly Phe Ser His Val Phe
            20

<210> SEQ ID NO 30
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Leu Lys Lys Trp Pro Trp Trp Pro Trp Arg Arg Lys
1               5                   10

<210> SEQ ID NO 31
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (9)..(9)
<223> OTHER INFORMATION: Any non-natural amino acid

<400> SEQUENCE: 31

Ile Xaa Lys Lys Trp Pro Trp Trp Xaa Trp Arg Arg Lys
1               5                   10

<210> SEQ ID NO 32
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45
```

```
<210> SEQ ID NO 33
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (11)..(11)
<223> OTHER INFORMATION: Any non-natural amino acid
<220> FEATURE:
<221> NAME/KEY: MOD_RES
<222> LOCATION: (18)..(18)
<223> OTHER INFORMATION: Any non-natural amino acid

<400> SEQUENCE: 33

Ser Ser Leu Leu Glu Lys Gly Leu Asp Gly Xaa Lys Lys Ala Val Gly
1               5                   10                  15

Gly Xaa Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45

<210> SEQ ID NO 34
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: source
<223> OTHER INFORMATION: /note="See specification as filed for detailed
      description of substitutions and preferred embodiments"

<400> SEQUENCE: 34

Gly Xaa Gly Ser Phe Xaa Lys Lys Ala Ala His Val Gly Lys His Xaa
1               5                   10                  15

Gly Lys Ala Xaa Leu Thr His Tyr Leu
            20                  25

<210> SEQ ID NO 35

<400> SEQUENCE: 35

000

<210> SEQ ID NO 36
<211> LENGTH: 23
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 36

Gly Xaa Gly His Phe Xaa His Ser Lys Lys Lys Phe Gly Lys Ala Xaa
1               5                   10                  15

Val Gly Glu Xaa Xaa Asn Ser
            20

<210> SEQ ID NO 37
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 37

Gly Xaa Gly His Phe Xaa His Ser Lys His Lys Phe Gly Lys Ala Xaa
1               5                   10                  15

Val Gly Glu Xaa Xaa Asn Ser
            20
```

```
<210> SEQ ID NO 38
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 38

Gly Xaa Gly His Phe Xaa His Ser Lys His His Phe Gly Lys Ala Xaa
1               5                   10                  15

Val Gly Glu Xaa Xaa Asn Ser
            20

<210> SEQ ID NO 39
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 39

Gly Xaa Gly Arg Phe Xaa His Ser Lys Lys Lys Phe Gly Lys Ala Xaa
```

```
1               5                   10                  15

Val Gly Glu Xaa Xaa Asn Ser
            20
```

<210> SEQ ID NO 40
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: MOD_RES
<222> LOCATION: (21)..(21)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 40

```
Gly Xaa Gly Arg Phe Xaa His Ser Lys Arg Lys Phe Gly Lys Ala Xaa
1               5                   10                  15

Val Gly Glu Xaa Xaa Asn Ser
            20
```

<210> SEQ ID NO 41
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: source
<223> OTHER INFORMATION: /note="See specification as filed for detailed
      description of substitutions and preferred embodiments"

<400> SEQUENCE: 41

```
Gly Xaa Gly Lys Phe Xaa His Ser Lys Lys Lys Phe Gly Lys Ala Xaa
1               5                   10                  15

Val Gly Glu Xaa Ala Asn Ser
            20
```

<210> SEQ ID NO 42
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: source
<223> OTHER INFORMATION: /note="See specification as filed for detailed description of substitutions and preferred embodiments"

<400> SEQUENCE: 42

```
Gly Xaa Gly Lys Phe Xaa His Ser Lys Lys Lys Phe Gly Lys Ala Xaa
1               5                   10                  15

Val Gly Glu Xaa Lys Asn Ser
            20
```

<210> SEQ ID NO 43
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: MOD_RES
<222> LOCATION: (6)..(6)
<223> OTHER INFORMATION: Any non-natural amino acid
<220> FEATURE:
<221> NAME/KEY: MOD_RES
<222> LOCATION: (16)..(16)
<223> OTHER INFORMATION: Any non-natural amino acid
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: source
<223> OTHER INFORMATION: /note="See specification as filed for detailed description of substitutions and preferred embodiments"

```
<400> SEQUENCE: 43

Gly Xaa Gly Lys Phe Xaa His Ser Lys Lys Lys Phe Gly Lys Ala Xaa
1               5                   10                  15

Val Gly Glu Xaa Ala Lys Lys
            20
```